US011505609B2

(12) United States Patent
Qin et al.

(10) Patent No.: US 11,505,609 B2
(45) Date of Patent: Nov. 22, 2022

(54) RECOMBINANT ANTIBODY HAVING UNIQUE GLYCAN PROFILE PRODUCED BY CHO HOST CELL WITH EDITED GENOME AND PREPARATION METHOD THEREOF

(71) Applicant: Bio-Thera Solutions, Ltd., Guangdong (CN)

(72) Inventors: Chao Qin, Guangzhou (CN); Yuanqing Zhou, Guangzhou (CN); Cuizhen Xiao, Guangzhou (CN)

(73) Assignee: Bio-Thera Solutions, Ltd., Guangzhou (CN)

( * ) Notice: Subject to any disclaimer, the term of this patent is extended or adjusted under 35 U.S.C. 154(b) by 15 days.

(21) Appl. No.: 16/337,371

(22) PCT Filed: Aug. 10, 2018

(86) PCT No.: PCT/CN2018/100008
§ 371 (c)(1),
(2) Date: Jan. 10, 2020

(87) PCT Pub. No.: WO2019/029713
PCT Pub. Date: Feb. 14, 2019

(65) Prior Publication Data
US 2020/0199236 A1 Jun. 25, 2020

(30) Foreign Application Priority Data
Aug. 11, 2017 (CN) .......................... 201710687889.9

(51) Int. Cl.
*C07K 16/28* (2006.01)
*C07K 16/30* (2006.01)
*A61K 39/395* (2006.01)
*C12N 9/10* (2006.01)
*C12N 15/62* (2006.01)

(52) U.S. Cl.
CPC ........ *C07K 16/2863* (2013.01); *A61K 39/395* (2013.01); *C07K 16/2887* (2013.01); *C07K 16/30* (2013.01); *C12N 9/1051* (2013.01); *C12N 15/62* (2013.01); *C07K 2317/40* (2013.01)

(58) Field of Classification Search
None
See application file for complete search history.

(56) References Cited

U.S. PATENT DOCUMENTS

| 2013/0058919 | A1 | 3/2013 | Lazar et al. | |
| 2013/0326645 | A1 | 12/2013 | Cost et al. | |
| 2014/0314748 | A1* | 10/2014 | Gokarn | C07K 16/22 424/133.1 |

FOREIGN PATENT DOCUMENTS

| CN | 102373214 | A | 3/2012 | |
| CN | 105392885 | A | 3/2016 | |
| CN | 106167525 | A | 11/2016 | |
| EP | 1688436 | A1 | 8/2006 | |
| EP | 1688436 | A1 | 9/2006 | |
| WO | 2012093833 | A2 | 7/2012 | |
| WO | WO2012093833 | A2 | 7/2012 | |
| WO | WO-2015168547 | A2 * | 11/2015 | .............. A61P 31/18 |
| WO | WO2015193740 | A2 | 12/2015 | |
| WO | 2016016842 | A1 | 2/2016 | |
| WO | WO2016016842 | A1 | 2/2016 | |

OTHER PUBLICATIONS

Gagez etal, Current Opinion Oncology; 2014; vol. 26; pp. 484-491.*
Mishra et al, Journal of Biotechnology 324S (2020) 100015.*
Cristea et al., "In vivo cleavage of transgene donors promotes nuclease-mediated targeted integration", Biotechnology and Bioengineering, vol. 110, No. 3, Mar. 1, 2013, pp. 871-880.
Supplementary European Search Report for EP Application No. 18842885.8 dated Apr. 7, 2021, 13 pages.
Extended European Search Report Application No. 18842885.8-1111/3666891; PCT/CN201810008, Date of Completion of Search Jul. 7, 2021, dated Jul. 16, 2021 (18 pages).
Sandra Cristea et al: "In vivo cleavage of transgene donors promotes nuclease-mediated targeted integration", Biotechnology and Bioengineering, vol. 110, No. 3, Mar. 1, 2013 (Mar. 1, 2013), pp. 871-880, XP055076901, DOI: 10.1002/bit.24733.
Yu et al: "Abstract 3823: Bat4306f, an anti-CD20 antibody devoid of fucose modification, demonstrates enhanced ADCC effect and potent in vivo efficacy: Cancer Research", Jul. 1, 2018 (Jul. 1, 2018), XP055821148, Retrieved from the internet: URL:https://cancerres.aacrjournals.org/con_tent/78/13Supplement/3823 [retrieved—on Jul. 5, 2021].
Yamane-Ohnuki N et al.: "Establishment of FUT8 knockout Chinese hamster ovary cells: an ideal host cell line for producing completely defucosylated antibodies with enhanced antibody-dependent cellular cytotoxicity", Biotechnology and Bioengineering, Wiley, US, vol. 87, No. 5, Aug. 6, 2004 (Aug. 16, 2004), pp. 614-622, XP002983758, ISSN: 0006-3592, DOI:10.1002/BIT.20151.

(Continued)

*Primary Examiner* — Bridget E Bunner
*Assistant Examiner* — Fozia M Hamud
(74) *Attorney, Agent, or Firm* — Sheppard Mullin Richter & Hampton LLP

(57) ABSTRACT

The present invention, in the field of bioengineering and biotechnology, relates to a method for preparing a recombinant antibody with a unique glycan profile produced by a genome-edited CHO host cell. Specifically, according to a method of the present invention, the TALEN technology is used to edit the FUT8 gene in CHO cells that have been adapted for serum-free suspension growth. The edited CHO host cells can produce recombinant antibodies with a unique glycan profile. The unique glycan profile can be characterized by non-fucosylated N-linked oligosaccharide chains of the antibodies, extremely low N-glycosylation heterogeneity and uniform carbohydrate chains. The antibody prepared by the method of the invention exhibit significantly increased ADCC and greater stability.

5 Claims, 8 Drawing Sheets

Specification includes a Sequence Listing.

(56) References Cited

OTHER PUBLICATIONS

Katsuhiro Mori et al: "Non-fucosylated therapeutic antibodies: the next generation of therapeutic antibodies", Cytotechnology, Kluwer Academic Publishers, DO, vol. 55, No. 2-3, Oct. 31, 2007 (Oct. 31, 2007), pp. 109-114, XP019550382, ISSN: 1573-0778, DOI: 10.1007/S10616-007-9103-2.
Sun "Using Crispr technology to knock out the FUT8 gene of CHO cells to produce completely fucose-free antibodies," Master's Thesis, Shanghai Jiaotong University, Pub: Jan. 4, 2017, Abstract. 1 page.
Anne-Laure Gagez et al: "Obinutuzumab: a new class of anti-CD20 monoclonal antibody" Current Opinion in Oncology, Sep. 2014 | vol. 26 | Issue 5 | pp. 484-491, Abstract. 1 page. doi: 10.1097/CCO.0000000000000107.

* cited by examiner

Electrophoretogram for functional verification of TALEN protein

Glycoscope Report: Glycoanalysis

| Sample Code | 7A4 | 7A5 | 7A6 | 7A7 |
|---|---|---|---|---|
| Customer Code | 41 | 43 | 1206 | Control |
| Table 1 | Value ± Error | Value ± Error | Value ± Error | Value ± Error |
| % Abundance in IgG-Fc Glycosylation | | | | |
| High Mannose | | | | |
| Total | 8 ± 3% | 10 ± 3% | 3 ± 1% | 3 ± 1% |
| Complex | | | | |
| Total | 92 ± 3% | 90 ± 3% | 97 ± 1% | 97 ± 1% |
| G0 | 92 ± 3% | 89 ± 3% | 86 ± 2% | 48 ± 4% |
| G1 | 0 ± 2% | 1 ± 2% | 11 ± 2% | 41 ± 3% |
| G2 | 0 ± 0% | 0 ± 0% | 0 ± 0% | 9 ± 2% |
| Antennae Termini | | | | |
| Sialic Acid | 0 ± 0% | 0 ± 0% | 0 ± 0% | 0 ± 0% |
| Gal alpha (1-3) Gal | 0 ± 0% | 0 ± 0% | 0 ± 0% | 0 ± 0% |
| Core Fucosylation | | | | |
| Total | 0 ± 5% | 10 ± 5% | 80 ± 5% | 81 ± 4% |

FIG. 5

```
⊠Concensus   AAGATTCTTGCAAAGCTGGAGCGCTTAAA-CAACAAAATGAAGACTTGAGGAGAATGGCTGAGTCTCTCCGGTAGGTTTGAAATACTCAAG
4                 630       640       650       660       670       680       690       700       710
191-1.seq    AAGATTCTTGCAAAGCTGGAGCGCTTAAA-------ATGAAGACTTGAGGAGAATGGCTGAGTCTCTCCGGTAGGTTTGAAATACTCAAG
191-2.seq    AAGATTCTTGCAAAGCTGGAGCGCTTAAAACAACAAAATGAAGACTTGAGGAGAATGGCTGAGTCTCTCCGGTAGGTTTGAAATACTCAAG
217-1.seq    AAGATTCTTGCAAAGCTGGAGCGCTTAAA-CAACAAAATGAAGACTTGAGGAGAATGGCTGAGTCTCTCCGGTAGGTTTGAAATACTCAAG
217-3.seq    AAGATTCTTGCAAAGCTGGAGCGCTTAAA-CAACAAAATGAAGACTTGAGGAGAATGGCTGAGTCTCTCGGGTAGGTTTGAAATACTCAAG
```

FIG. 6

RECOMBINANT ANTIBODY HAVING UNIQUE GLYCAN PROFILE PRODUCED BY CHO HOST CELL WITH EDITED GENOME AND PREPARATION METHOD THEREOF

CROSS REFERENCE TO RELATED APPLICATIONS

The present application is a national stage application of International Application PCT/CN2018/100008, filed Aug. 10, 2018, which claims the benefit of Chinese Patent Application No. 201710687889.9 filed Aug. 11, 2017, the contents of which are incorporated by reference in their entireties into the present disclosure.

SEQUENCE LISTING

The instant application contains a Sequence Listing which has been filed electronically in ASCII format and is hereby incorporated by reference in its entirety. Said ASCII copy, updated on Sep. 21, 2020, is named 63CP-292919-US-_SL.txt and is 87,731 bytes in size.

TECHNICAL FIELD

The present invention belongs to the field of bioengineering and biotechnology, and relates to a class of recombinant antibodies with a unique glycan profile produced by a genome-edited CHO host cells and preparation methods for the host cells and antibodies.

BACKGROUND ART

CHO cells (Chinese Hamster Ovary, CHO) are epithelial anchorage-dependent cells extensively used in bioengineering at present, which were first isolated from the ovary of an adult female hamster in 1957 by Dr. Theodore T. Puck from the University of Colorado. CHO-K1 cells are widely used in industrial production. As transformed cell lines, such cells are hypodiploid cells having the chromosome distribution frequency 2n=22. The CHO-K1 cell lines (No. CCL-61), which are preserved by ATCC, have been widely used to express the recombinant DNA protein. The original cells are anchorage-dependent cells and can also grow in suspension after multiple passages and screening. CHO cells are prone to gene mutation and gene transfection. Early studies also demonstrated that, compared with other engineering cell lines, antibodies produced by the CHO cells have the most similar glycotype to the human serum antibodies; thus the CHO cells are good host cells for mammalian gene expression.

The mechanism of therapeutic antibodies is to form a complex with the target molecule, causing neutralization of the target antigen or eliminating the antigen or pathogen through the immunological effect of the Fc fragment of the antibody. The specific binding ability of antibody drugs to target molecules as well as their activity depend on their complex multi-level structure and post-translational modification; moreover, as the most important post-translational modification of antibody, glycosylation plays an important role in the biological activity, metabolism and immunogenicity of the antibodies. The glycosylation forms of antibody drugs are mainly N-glycosylation, involving such monosaccharides as glucose, galactose, mannose, N-acetylglucosamine, N-acetylgalactosamine, fucose and sialic acid (NANA, NGNA). Based on the amount of terminal galactose, the two-branched or multi-branched double-antenna complex oligosaccharides connected to Fc fragment Asn297 of the antibody molecule can be divided into G0, G1 (1, 3), G1 (1, 6) and G2, and each type can be further divided into 16 subtypes according to the presence of fucose (F) or bisected galactose (B) (Glycobiology, Volume 25, Issue 12, December 2015, Pages 1325-1334). Therefore, there are at least 36 types of oligosaccharides of the antibody heavy chain, even without considering terminal sialylation or high mannose; meanwhile, as the two heavy chains of the antibody can be randomly combined to form up to 400 different glycotypes, the antibody shows high heterogeneity.

Different glycotypes have different effects on the pharmaceutical properties of therapeutic antibodies. High mannose (ManS) results in rapid elimination of antibodies in blood and shortens half-life (MAbs, 2012, 4 (4): 509-520). GOF promotes complement pathway and accelerates elimination rate. The content of G2F increases in pregnant women and neonatal umbilical cords. Sialic acid modification has a significant effect on the inflammation of intravenous immunoglobulin. A decrease of fucose results in a significant increase of ADCC activity (JBC (2003) Chemistry 278, 3466-3473). Therefore, it is necessary to design and optimize the carbohydrate chain of therapeutic antibodies according to their main mechanism of action and therapeutic use.

Unlike protein expression, the glycosylation of the antibodies does not have a template to follow, and its glycosylation type and proportion of oligosaccharide components are affected by the host cell type and culture conditions. Methods of modifying the oligosaccharide components of monoclonal antibodies by engineering host cells to enhance their Fc-mediated effects are scattered in different literatures and patents. For example, antibodies prepared with the CHO cells overexpressed with β(1,4)-N-acetylglucosaminyltransferase III (GnT III) have higher ADCC activity than those expressed in parent cells, and the difference in activity is about 10 to 20 times (Bio Technol Bioeng. (2001) August 20; 74 (4): 288-94). However, the overexpression of GnT III is toxic to the CHO cells and the expression quantity of GnT III tends to decrease as heterogeneous expression increases with the passage number in the culture process. The fucose content of antibodies produced by using GnT III as host cells will change, thus affecting the uniformity of antibody drugs. Examples of the cell lines producing nonfucosylated antibodies also include Lec13 CHO cells with protein fucosylation defects (Ripka et al. Arch. Biochem. Biophys. 249: 533-545 (1986)), but they are not suitable as the host cells for the production of therapeutic antibodies due to their extremely low protein production (Yutaka Kanda et al. Biotechnol Bioeng. (2006) July 5; 94(4):680-8). CHO cells (Yamane-Ohnuki et al. (2004), Biotech. Bioeng. 87:614) with α-1-6 fucosyltransferase gene FUT8 knocked out also result in a decrease in the production of antibody fucose. In FUT8 knockout cell lines as described in Yamane-Ohnuki and Kyowa Hakko patents, a method for controlling antibody fucose level and improving ADCC (antibody-dependent cell-mediated cytotoxicity) effect is disclosed. According to this method, the expression of FUT8 gene in a host cell is inhibited by a specific siRNA so as to reduce the fucose level of antibodies produced by the host cell. However, this method has the same disadvantages as the CHO cell lines overexpressing GnT III described above. First, the host cells have to be introduced with exogenous sequences; second, only up to about 70% of target genes can be inhibited by siRNA; and finally, the stability of siRNA expression may affect the quality properties of antibody drugs.

Recently, new genome editing techniques used for editing host cell target genes, inactivating the FUT8 enzyme in the cell and lowering the fucose level of antibody have been reported repeatedly in different literatures and patents. For example, Malphettes et al. (2010) reported that parent cells DG44 were knocked out by the zinc finger nuclease (ZFN) technology to obtain the homozygous FUT8 gene knockout DG44 derivative clone, and the antibody produced by this cell line was completely free of fucose. Beurdeley et al. (2012) reported that the FUT8 gene of CHO-K1 cells was edited by the TALEN technology, resulting in the loss of FUT8 enzyme activity in the host cells. Again, Sun et al. (2015) reported that editing exon 10 of FUT8 gene by the CRISPR/Cas9 technology resulted in loss of FUT8 enzyme activity in CHO-K1 cells.

SUMMARY OF THE INVENTION

In view of the problems that although the existing antibody drugs are basically limited to single N-glycosylation modification of Fc, the production stability is affected by inconsistent and easily changing glycotype components and contents, it is necessary to provide antibodies with a unique glycan profile produced by genome-edited CHO host cells, and methods for preparing the antibodies. The purpose of the present invention is achieved by the following technical means:

In a first aspect, the present invention provides a pair of polypeptides comprising the amino acid sequences as shown in SEQ ID NO. 10 and SEQ ID NO. 11, or comprising at least 90%, at least 91%, at least 92%, at least 93%, at least 94%, at least 95%, at least 96%, at least 97%, at least 98% or at least 99% sequence identity to the sequences as shown in SEQ ID NO. 10 and SEQ ID NO. 11. In some embodiments, the pair of polypeptides as shown in SEQ. NO. 10 and SEQ. NO. 11 have the amino acid sequence of the DNA binding domains upstream and downstream of TALEN respectively, and can specifically bind specific base zones of genes.

In a second aspect, the present invention provides a pair of polynucleotides encoding the pair of polypeptides as shown in SEQ. NO. 10 and SEQ. NO. 11, respectively. In some embodiments, the pair of polynucleotides comprise the nucleic acid sequences as shown in SEQ ID NO. 12 and SEQ ID NO. 13, or comprise at least 90%, at least 91%, at least 92%, at least 93%, at least 94%, at least 95%, at least 96%, at least 97%, at least 98% or at least 99% sequence identity to the sequences as shown in SEQ ID NO. 12 and SEQ ID NO. 13.

In a third aspect, the present invention provides a pair of fusion proteins formed by fusing a pair of polypeptides described above to the amino acid sequence of a DNA cleavage domain of a transcriptional activator-like effector (FokI). In some embodiments, the amino acid sequence of the DNA cleavage domain of the transcription activator-like effector (FokI) is natural or artificially modified. In some embodiments, the pair of fusion proteins comprise the amino acid sequences as shown in SEQ ID NO. 14 and SEQ ID NO. 16, or comprise at least 90%, at least 91%, at least 92%, at least 93%, at least 94%, at least 95%, at least 96%, at least 97%, at least 98% or at least 99% sequence identity to the sequences as shown in SEQ ID NO. 14 and SEQ ID NO. 16. In some embodiments, the pair of fusion proteins can specifically recognize two nucleotide sequences of CHO's FUT8 gene. In some embodiments, the two nucleotide sequences of CHO's FUT8 gene are located on the exon 1 (Exon1, SEQ ID NO. 7) of the FUT8 gene. In some embodiments, the two nucleotide sequences of the FUT8 gene comprise the nucleotide sequences as shown in SEQ ID NO. 3 and SEQ ID NO. 4 respectively. In some embodiments, a Space between the nucleotide sequences as shown in SEQ ID NO. 3 and SEQ ID NO. 4 comprise the sequence as shown in SEQ ID NO. 5.

In a fourth aspect, the present invention also provides a pair of nucleotides encoding the pair of fusion proteins respectively. In some preferred embodiments, the pair of nucleotide comprise the nucleic acid sequences as shown in SEQ ID NO. 15 and SEQ ID NO. 17, or comprise at least 90%, at least 91%, at least 92%, at least 93%, at least 94%, at least 95%, at least 96%, at least 97%, at least 98% or at least 99% sequence identity to the sequences as shown in SEQ ID NO. 15 and SEQ ID NO. 17.

In a fifth aspect, the present invention also provides a vector of at least any one polynucleotide of the pair of polynucleotides. In some embodiments, the vector is a plasmid.

In a sixth aspect, the present invention also provides host cells transfected with the vector.

In some embodiments, these cells transfected with the vector are the genome-edited CHO host cells, and their parent cells are derived from the CHO-K1 cell lines.

In some embodiments, parent cells of genome-edited CHO host cells are adapted to serum-free suspension culture; and the parent cells are named as CHO-BAT.

In some embodiments, the parent cells CHO-BAT of the genome-edited CHO host cells are a subclone of CHO-K1 selected to satisfy one or more of the following characteristics:

The cells have high transfection efficiency;

The cells have a short exponential growth time;

The cells have the ability to achieve a high cell density in the CD-CHO culture.

In some embodiments, compared with the parent cells, the genome-edited CHO host cells cause the endogenous α-1, 6-fucosyltransferase (FUT8) to lose its enzymatic activity due to the base deletion, insertion and nonsense mutation in certain zones of the FUT8 gene.

The cells do not contain exogenous DNA sequences; The cells as host cells express recombinant antibodies having unique glycan profile characteristics.

In some embodiments, the genome-edited CHO host cells are characterized in that the genome of exon 1 of the FUT8 gene of the cells is edited, causing the endogenous FUT8 of the cells to loss enzyme activity; and the cells do not contain the DNA sequence of the expression vector introduced in the process of causing base deletion and unintentional mutation of the FUT8 gene; The cells as host cells express recombinant antibodies having unique glycan profile characteristics are characterized by having non-fucosylated N-linked oligosaccharide and other glycan profile characteristics of the antibodies.

In some embodiments, the FUT8 gene of the genome-edited CHO host cells is knocked out, the cells' lectin LCA binding is negative, and the cells are named as CHO-BAT-KF.

In a seventh aspect, the present invention provides a kit comprising at least any one polypeptide of the pair of polypeptides, or at least any one polynucleotide of the pair of polynucleotides, or at least any one fusion protein of the pair of fusion proteins, or the vector, or the host cell.

In an eighth aspect, the present invention provides a use of the pair of polypeptides/polynucleotides/fusion proteins, or the vector in the FUT8 gene-edited CHO cells.

In a ninth aspect, the present invention provides a use of the pair of polypeptides/polynucleotides/fusion proteins, or the vector or the host cell in the production of antibodies, especially the antibodies with unique glycan profile, or provides the antibodies produced by the pair of polypeptides/polynucleotides/fusion proteins, or the vector or the host cell.

In a tenth aspect, the present invention provides a method for editing the FUT8 gene of CHO, comprising the following steps: transferring the pair of fusion proteins or the pair of polynucleotides or the vector into the CHO cells, incubating at 37° C. for 14 days, and obtaining the FUT8 gene knockout CHO cells through pressure screening and limited dilution. Refer to Wood et al., J Immunol. 145:3011 (1990) for exemplary methods.

In an eleventh aspect, the present invention provides a method for preparing a recombinant antibody with a unique glycan profile produced by genome-edited CHO host cells, comprising the following steps:

(1) transfecting the CHO cells (e.g. wild-type CHO cells) with the pair of fusion proteins or the pair of polynucleotides or the vector, and obtaining the FUT8 gene knockout CHO cells through pressure screening and limited dilution;

(2) electrically transfecting the FUT8 gene knockout CHO cells with the plasmid encoding the antibody gene expression cassette, and obtaining stable CHO cell lines secreting antibodies through pressure screening and limited dilution;

as a preferred embodiment, the vector is transfected into wild-type CHO cells described in step (1); more preferably, the plasmid is stably transfected into wild-type CHO cells;

as a preferred embodiment, the CHO cell is CHO-K1; more preferably, the CHO-K1 is adapted to serum-free culture.

As a preferred embodiment, the antibody is an anti-CD20 antibody; more preferably, the antibody is a humanized or full human anti-CD20 antibody; more preferably, the antibody is BAT4306F; more preferably, the antibody BAT4306F comprises two light chains as shown in SEQ ID NO. 20 and two heavy chains as shown in SEQ ID NO. 21. The inventor has adopted the method, cells, polypeptides and the like of the present invention to prepare various types of antibodies. It is found through research that different types of the prepared antibodies all show highly consistent glycotype and low heterogeneity, which means that the method, cells and the like of the present invention are suitable for the preparation of all types of antibodies. In one embodiment, the antibody binds CD20. In one embodiment, the CD20 binding antibody is a humanized antibody. In a preferred embodiment, the humanized antibody BAT4306F has a heavy chain variable zone B-HH6 amino acid sequence and a light chain variable zone B-KV1 amino acid sequence from the B-Ly1 antibody sequence in WO2005044859. BAT4306F antibody comprises a pair of light and heavy chains of the following sequences: SEQ ID NO. 20 and SEQ ID NO. 21. In one embodiment, the CD20 binding antibody is a full human antibody BAT4406F, which comprises a pair of light and heavy chains of the following sequences: SEQ ID NO. 22 and SEQ ID NO. 23. In one embodiment, the antibody is BAT1206F, and the BAT1206F antibody comprises two light chains as shown in SEQ ID NO. 18 and two heavy chains as shown in SEQ ID NO. 19. In one embodiment, the antibody is BAT0206F, and BAT0206F binds to EGFR, and comprises two light chains as shown in SEQ ID NO. 24 and two heavy chains as shown in SEQ ID NO. 25. In one embodiment, the antibody is BAT0808, and BAT0808 binds to Trop2, and comprises two light chains as shown in SEQ ID NO. 26 and two heavy chains as shown in SEQ ID NO. 27. In some embodiments, the modified glycoprotein is secreted by a host cell. In some embodiments, the modified glycoprotein is an antibody.

As an exemplary embodiment, the present invention provides a method for preparing a recombinant antibody with unique glycan profile produced by the genome-edited CHO host cell or an antibody produced by the method, comprising the following specific steps:

Transfect the pair of fusion proteins or the pair of polynucleotides or the vector into the wild-type CHO cells, adding CD CHO (Sigma)+10% FBS (fetal calf serum) containing phytohemagglutinin (LCA) into the transfected cells and perform the pressure screening; after 14 days, seed the surviving cells into a 96-well cell culture plate at 0.5 cells/well, and decrease the serum concentration to 5%; after 7 days, transfer the cells into a 24-well cell culture plate, incubate in a 37C $CO_2$ incubator for 7 days. Then, take out some cells, centrifuge at 1000 rpm for 5 min, resuspend in PBS, mix 2 μl of fluorescein labeled LCA with the cells, and incubating on ice for 30 min. Next, wash the cells with PBS once and read fluorescence on a flow cytometry (BD, C6); take the untransfected wild-type CHO cells as negative control. Transfer positive cells to a 6-well cell culture plate, and decrease the serum concentration to 1%; after 7 days, transfer cells to a small shake flask, and taking serum-free CD CHO as the medium. Then, the domestication process is completed. Use a plasmid extraction kit (Omega) to extract the CHO genome from some cells. By taking the genome as a template, carry out the polymerase chain reaction (PCR) with the primers L130for (SEQ ID NO. 1), L130rev (SEQ ID NO. 2) and taq enzyme, and catalyzes the joining of the PCR product and T-vector (Promega), transform into E. coli competent cells, and coat plates. On the next day, pick single colonies, and sequence with T7 primer. Analyze the sequences by the DNASTAR analysis software, compared with the wild-type CHO genome sequence, colony with base deletions expands in culture and is named as CHO-BAT-KF Establish a cell bank for CHO-BAT-KF when the cells being at logarithmic growth phase, and freezing the cells with CD CHO cryoprotectant containing 7.5% of DMSO, and transfer them to a liquid nitrogen tank for long-term storage. Linearize the plasmid encoding the antibody gene, measure OD260, mix 50 μg of plasmid with 10' CHO-BAT-KF in electric rotor, transfect with an electroporator (Biorad), seed the cell into a 96-well cell culture plate, and add methionine sulfoximine (MSX) after 48 h. After 14 days, coat the ELISA plate with an anti-FC multi-antibody; after blocking with 3% BSA, add supernatant to the plate and incubate at 37° C. for 2 h. Wash with PBST for 5 times, add anti-HRP labeled goat anti-human kappa/lambda light chain, 2M $H_2SO_4$, and read OD450 value on a microplate reader. The colonies with high titer are expanded, and the cell supernatant is collected by centrifugation to obtain the fucose-knocked antibody protein.

The present invention also provides a cell, which is a genome-edited CHO host cell.

The edited FUT8 gene of the genome-edited CHO host cells described above comprise the sequence as shown in SEQ ID NO. 28, or the sequence comprising at least 90%, at least 91%, at least 92%, at least 93%, at least 94%, at least 95%, at least 96%, at least 97%, at least 98%, at least 99%, at least 99.5%, or at least 99.8% sequence identity to the sequence as shown in SEQ ID NO. 28.

The present invention also provides a nucleic acid comprising a sequence as shown in SEQ ID NO. 28, or a nucleic acid comprising at least 90%, at least 91%, at least 92%, at least 93%, at least 94%, at least 95%, at least 96%, at least 97%, at least 98%, at least 99%, at least 99.5%, or at least 99.8% sequence identity to the sequence as shown in SEQ ID NO. 28.

The invention also provides a CHO host cell preserved in China Center for Type Culture Collection (CCTCC NO: C2017127; date: Aug. 10, 2017; address: Wuhan University, Wuhan, China; classified designation: CHO-BAT-KF FUT8 (−/−)).

In some embodiments, the host cell is kept in a serum-free medium. In some embodiments, the host cell is kept in a suspension culture. The invention also relates to a medium containing the host cells and a culture fermenter containing multiple host cells in the medium. In some embodiments, the medium is serum-free.

In a twelfth aspect, the present invention provides an antibody, which is a recombinant antibody with a unique glycan profile produced by the genome-edited CHO host cell. The antibody is a humanized or full human antibody having a unique glycosylation mode, a low heterogeneity of N-glycosylation and a significantly increased ADCC effect.

In some embodiments, the recombinant antibody with a unique glycan profile produced by the genome-edited CHO host cell is a humanized antibody binding CD20 on the cell membrane surface.

In some embodiments, the recombinant antibody with a unique glycan profile produced by the genome-edited CHO host cell has a unique glycosylation mode characterized in a change in the level of one or more saccharide fractions of the antibody N-linked polysaccharide has a unique glycosylation mode, wherein the saccharide fractions are selected from glucose (Glc), fucose (Fuc), galactose (Gal), mannose (Man), high mannose, glucosamine, G0 and acetylglucosamine (GlcNAc).

The characteristics of glycosylation mode satisfy one or more of the following preferred conditions:

The fucose content of the antibody is very low; (0-5%)
The galactose level of the antibody is low; (≤30%)
The mannose level of the antibody is low; (≤5%)
The high mannose level of the antibody is low; (≤5%)
The G0 level of the antibody is high. (≥60%)

In some embodiments, the antibody has a low galactose level, ≤5%.

In some embodiments, the antibody has a high G0 level, ≥80%.

In some embodiments, the recombinant antibody with a unique glycan profile produced by the genome-edited CHO host cell satisfies the preferred condition that the fucose content is 0.

In some embodiments, the recombinant antibody with a unique glycan profile produced by the genome-edited CHO host cell has extremely low heterogeneity of N-polysaccharide and uniform carbohydrate chain.

In some embodiments, the recombinant antibody with a unique glycan profile produced by the genome-edited CHO host cell has a strong ADCC effect of Fc.

In some embodiments, the antibody has a glycan profile as shown for BAT4306F in the upper FIG. 10 of the Specification.

In some embodiments, the BAT4306F comprises two light chains as shown in SEQ ID NO. 20 and two heavy chains as shown in SEQ ID NO. 21; however, it is not excluded that these sequences are mutated as long as these mutations do not affect the function of the antibody.

In a thirteenth aspect, the present invention provides a FUT8 gene knockout CHO host cell, and the first exon of the FUT8 gene in this CHO host cell contains an inactivating mutation. This mutation may be one or more amino acid substitutions or deletions, or a frameshift mutation as shown in FIG. 6.

The present invention also provides a pharmaceutical composition comprising the antibody. As a preferred embodiment, the pharmaceutical composition also contains a pharmaceutically acceptable carrier.

The present invention also provides a method for preventing/treating a disease, comprising administering an effective amount of the antibody/fragment thereof disclosed herein to a subject in need thereof. In some embodiments, the disease is selected from the group consisting of cancer, anaphylaxis, cardiovascular disease, inflammatory disease, metabolic disease, neurological disease, viral infection, and/or bacterial infection. For example, the disease may be cancer or anaphylaxis. In some embodiments, the subject is mammal, such as a human being.

Compared with the existing antibody drugs, the present invention has the following advantages:

At present, the marketed antibody drugs are basically limited to the single N-glycosylation modification of Fc, however, due to inconsistent glycotype compositions and contents and easy changes, are complicated to a certain extent, especially posing a challenge to their stable production. According to the present invention, the recombinant antibody with unique glycan profile produced by the genome-edited CHO host cell has low N-glycosylation heterogeneity and good carbohydrate chain uniformity; at the same time, its ADCC effect is enhanced, and thus it greatly improves the quality and pharmaceutical properties of antibody drugs.

Compared with the corresponding antibody produced by the unmodified CHO-K1 (ATCC # CCL-61) or suspension-adapted parent cell CHO-BAT, the binding affinity of the antibody to the FcγRIIIA receptor is increased.

The modified host cells produce antibodies that have an enhanced affinity for FcγRIIIA compared with the corresponding antibodies produced by the unmodified host cells.

BRIEF DESCRIPTION OF THE DRAWINGS

FIG. 5 shows the carbohydrate chain chip analysis, wherein the fucose content of the submitted gene-edited clones 41 and 43 is reduced to 0-10%, while the fucose content of the wild-type antibody 1206 is 80%.

FIG. 6 shows the sequencing of the target sequence of TALEN protein after PCR amplification, with the results being compared by the lasergeneMegAlign sequence analysis software. 191-1, 191-2, 217-1, 217-3 are four selected clones with regulated genomes. Genomes were extracted as DNA templates, PCR reaction was performed with primers L130for and L130rev, and CEL-1 base mismatch analysis was performed on the amplification products. The results show that cell clones 191-1 and 191-2 were heterozygous and cell clones 217-1 and 217-3 were homozygous. According to the comparison of results, the genome-edited homozygote 217-1 and 217-3 were selected and designated as CHO-2G8 and CHO-1D6. CHO-2G8 was finally selected as the host cell for subsequent experiments, and the host cell was named as CHO-BAT-KF.

Figure 1:
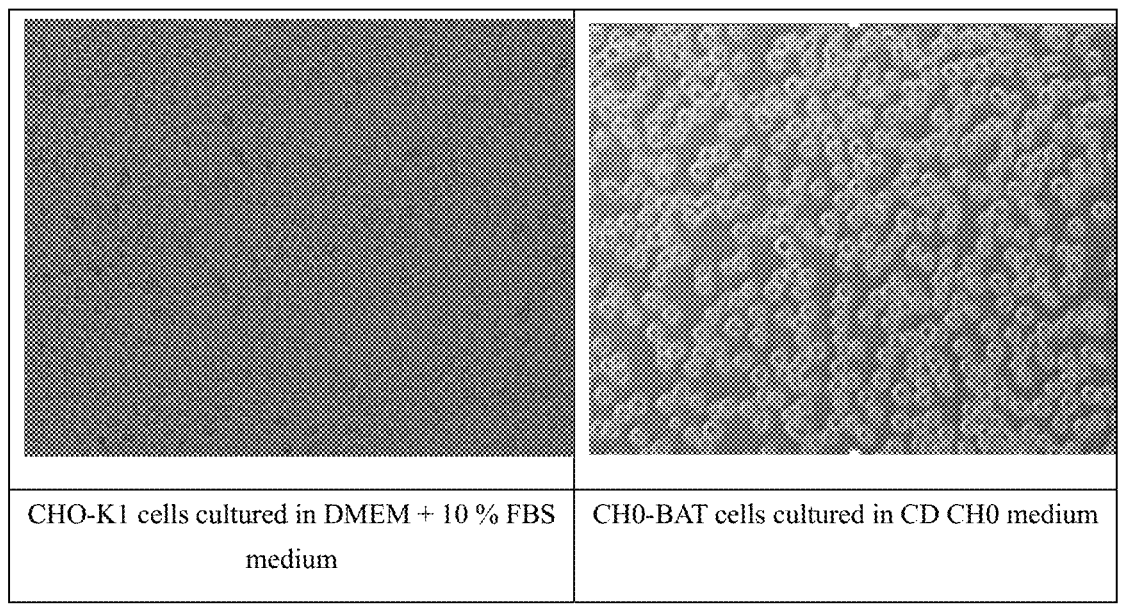
FIG. 1 shows an anchorage-dependent CHO-K1(ATCC # CCL-61) and a CHO-BAT cell line adapted to suspension growth in serum-free medium.

The genome-edited CHO host cell of the invention is preserved in China Center for Type Culture Collection (CCTCC NO: C2017127; date: Aug. 10, 2017; address: Wuhan University, Wuhan, China; classified designation: CHO-BAT-KF FUT8(−/−)).

DETAILED DESCRIPTION OF THE INVENTION

The technical scheme of the present invention is further described in combination with the detailed embodiments, which do not represent limitations to the protection scope of the present invention. Non-essential modifications and adjustments made by others according to the concept of the present invention shall still fall into the protection scope of the present invention.

It should be noted that in the present invention, "level" or "content" of the saccharide fraction of the antibody has the same meaning, indicating the mass ratio of a certain saccharide fraction in all saccharide fractions of the antibody.

According to the present invention, an "amino acid" refers to a carboxyl-α-amino acid, which may be encoded by a nucleic acid directly or in the form of precursor. A single amino acid is encoded by nucleic acid consisting of three nucleotides (so-called codons or base triple). Each amino acid is encoded by at least one codon. The encoding of the same amino acid by different codons is called "degeneracy of genetic code". The term "amino acid" used in the present application refers to the naturally occurring carboxyl-α-amino acid, which includes alanine (three-letter code: ala, one letter code: A), arginine (arg, R), asparagine (asn, N), asparagine (asn, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y) and valine (val, V).

In the present invention, the terms "polynucleotide" or "nucleic acid" or "nucleic acid sequence" are used interchangeably and refer to polymer molecules consisting of mononucleotide (also called bases) a, c, g, and t (or u in RNA), such as DNA, RNA, or modified forms thereof. The polynucleotide molecule may be a naturally occurring polynucleotide molecule, or a synthetic polynucleotide molecule, or a combination of one or more naturally occurring polynucleotide molecules and one or more synthetic polynucleotide molecules. The definition also includes naturally occurring polynucleotide molecules in which one or more nucleotides are altered (e.g., by mutagenesis), deleted, or added. The nucleic acids may be isolated or integrated into another nucleic acids such as expression cassettes, plasmids or chromosomes of the host cells. The nucleic acids are characterized by a nucleic acid sequence consisting of a mononucleotide. The operation and method for converting amino acid sequences such as polypeptides into corresponding nucleic acid sequences encoding the amino acid sequences are well known to those skilled in the art. Therefore, nucleic acids can be characterized by their nucleic acid sequences consisting of mononucleotide or by the amino acid sequences of the polypeptides encoded by them.

Also, the terms "polynucleotide" or "nucleic acid" or "nucleic acid sequence" may contain modified nucleotides in percentage of the total number of nucleotides present in the nucleic acid molecule, such as at least about 5%, 10%, 15%, 20%, 25%, 30%, 35%, 40%, 45%, 50%, 55%, 60%, 65%, 70%, 75%, 80%, 85%, 90%, 95% or 100% modified nucleotides.

The term "polypeptide" in the present invention is a polymer comprising amino acids linked by peptide bonds, which can be produced naturally or synthetically. Polypeptides with less than about 20 amino acid residues may be referred to as "peptides", however, molecules consisting of two or more peptides or molecules containing one polypeptide with more than 100 amino acid residues may be referred to as "proteins". Polypeptides may also contain non-amino acid components such as glycosyls, metal ions, or carboxylic acid esters. Non-amino acid components can be added by cells expressing this polypeptide and can vary with the type of cells. A polypeptide is defined herein according to its amino acid backbone structure or nucleic acid encoding it. The addition of glycosyl, for example, is generally not specified, but may be allowed. Also, the "polypeptide" may contain modified amino acids in percentage of the total number of amino acids present in the amino acid molecule, such as at least about 5%, 10%, 15%, 20%, 25%, 30%, 35%, 40%, 45%, 50%, 55%, 60%, 65%, 70%, 75%, 80%, 85%, 90%, 95% or 100% modified amino acids.

In the present invention, the term "host cell" refers to a microorganism or eukaryotic cell or cell line cultured in a mononuclear entity, which may be or has been used as a recipient of a recombinant vector or other transferred polynucleotide, and includes an offspring of the transfected original cell. In some embodiments, the host cells are non-lymphocytes, and the host cells produce the same unique glycan profile. In some embodiments, the host cells are, such as NSO cells, simian COS cells, Chinese hamster ovary (CHO) cells, etc. In some embodiments, the host cells are selected from Chinese hamster ovary (CHO) cells. In some embodiments, the host cells are selected from CHO-K1, CHO-S, DUXB11, CHO-1E5, CHO3F, CHO/DG44, CHO-BAT and CHO-2.6 cells. In some embodiments, the host cells generate antibodies that exhibit a unique glycan profile. The genome-edited CHO host cells of the present invention, such as CHO-BAT-KF FUT8(−/−) can be grown in a culture and devices (including fermenters) that can be used to grow the culture. They can grow into a single layer or attach to a surface; alternatively, the host cells may grow in suspension. The cells can grow in serum-free medium. The medium may be a commercially available medium such as, but not limited to, DMEM/F12. The edited CHO host cells can maintain its specific unique glycan profile in the medium for many generations. For example, the edited CHO host cells retain their specific unique glycan profile for at least about 20, 30, 40 or 50 generations. In some embodiments, the modified CHO host cells retain their unique glycan profile for at least about 60 generations. In another embodiment, the modified CHO host cells retain their unique glycan profile for at least about 100, 150, 200, 500, 1000 or more generations.

The glycosylation mode of the host cells may be N- or O-glycosylation of any protein moiety, wherein one or more glucose molecules may be added to amide nitrogen of asparagine or hydroxyl oxygen of hydroxylysine, hydroxyproline, serine or threonine, respectively. The glycosylation mode is characterized by a change in the level of at least two or more glucose molecules or saccharides, such as monosaccharides, disaccharides, polysaccharides or oligosaccharides. For example, the glucose molecules may be trisaccharides, tetrasaccharides, pentoses, hexasaccharides, heptoses, octasaccharides, nonasaccharides, or derivatives thereof, such as deoxysaccharides (e.g., deoxyhexasaccharides); N- or O-substituted derivatives such as sialic acid; or saccharides with amino groups. The glucose molecules may include, but are not limited to, galactose (Gal), glucose (Glc), mannose (Man), N-acetylneuraminic acid (NeuAc), fucose (Fuc), N-acetylgalactosamine (GalNAc), N-acetylglucosamine (GlcNAc) and xylose. The glucose molecules can be linked to other glucose molecules by $\alpha$ or $\beta$ linking.

The term "antibody" of the present invention includes all forms of antibodies, such as recombinant antibodies, humanized antibodies, chimeric antibodies, single chain antibodies, fusion antibodies, monoclonal antibodies and polyclonal antibodies. The antibodies may also be fragments. The antibodies can also bind drugs, toxins or therapeutic radioisotopes. The host cells of the present invention may also produce bispecific antibody fusion proteins, including hybrid antibodies that bind more than one antigen. Thus, antibodies include naked antibodies and binding antibodies as well as antibody fragments, and they may be single-specific or multi-specific.

As alternative embodiments, the antibodies or fragments thereof are not particularly limited to and may be selected from anti-HER2, anti-CD20, anti-EGF, anti-VEGF, anti-PDGF, anti-EpCam, anti-CD3, anti-CD4, anti-CD19, anti-CD30, anti-CD33, anti-CD40, anti-CD51, anti-CD55, anti-CD80, anti-CD95, anti-CCR2, anti-CCR3, anti-CCR4, anti-CCR5, anti-folic acids, anti-CXCR4, anti-EGFR or Trop2 antibodies, etc. As preferred embodiments, the antibodies are humanized or full human antibodies.

In a pharmaceutical composition of the present invention, a pharmaceutical preparation for storing the antibodies of the present invention is prepared in the form of a lyophilized preparation or an aqueous solution by mixing the antibodies with a desired degree of purity with optional physiologically acceptable carriers, excipients or stabilizers (Remington's Pharmaceutical Sciences 16th edition, Osol, A. Ed. (1980)). Acceptable carriers, excipients or stabilizers are non-toxic to the recipient at the dose and concentration applied, and include buffer solutions such as phosphates, citrates and other organic acids; antioxidants such as corbic acid and methionine; preservatives (such as benzyldimethyl octadecyl ammonium chloride; hexamethyl ammonium chloride; benzalkonium chloride, benzethonium chloride; phenol, butanol orbenzyl alcohol; alkyl p-hydroxybenzoates, such as methyl or propyl p-hydroxybenzoate; catechol; resorcinol; cyclohexanol; 3-propanol and m-cresol); low molecular weight (less than about 10 residues) polypeptides; proteins such as serum albumin, gelatin, or immunoglobulin; hydrophilic polymers such as polyvinylpyrrolidone; amino acids such as glycine, glutamine, asparagine, histidine, arginine or lysine; monosaccharides, disaccharides and other carbohydrates such as glucose, mannose or dextrin; chelating agents such as EDTA; saccharides such as sucrose, mannitol, trehalose or sorbitol; salt-forming counter ions such as sodium; metal complexes (e.g. Zn-protein complexes); and/or nonionic surfactants such as Tween, Pluronics™ or polyethylene glycol (PEG).

The antibodies, pharmaceutical compositions and pharmaceutical preparations of the present invention may be administered by any suitable means, including parenteral, subcutaneous, intraperitoneal, intrapulmonary and intranasal means; and, if necessary, intralesional administration may be used for local immunosuppressive treatment. The parenteral perfusion includes intramuscular, intravenous, intraarterial, intraperitoneal or subcutaneous administrations. In addition, the antibody of the present invention can be suitably administered by pulsed perfusion (in particular, dose gradient changes of the antibodies of the present invention). Depending on the administration time, preferably, the injection administration is used; more preferably, intravenous or subcutaneous injection is used. ADCC (antibody-dependent cell-mediated cytotoxicity) refers to a cell-mediated reaction in which the effector cells expressing FCR (e.g., natural killer (NK) cells, neutrophils, and macrophages) recognize the antibodies bound to target cells and then lyse the target cells. Primary cells used to mediate ADCC include NK cells, monocytes and macrophages. In general, NK cells mainly express FcγRIII, while monocytes express FcγRI, FcγRII and FcγRIII. In the present invention, the maternal CHO cell line is edited to produce a CHO cell line with a unique glycan profile. The edited CHO cell line can then produce antibodies with higher ADCC activity than antibodies produced by the maternal CHO cells.

Example 1 Screening of Parent Cells Adapted to Serum-Free Suspension Culture

CHO-K1 was cultured in DMEM/F12 medium containing 10% FBS. When the cell confluence reached 80%-90%, washed with PBS and digest with trypsin. Then, terminated by DMEM/F12 medium containing 5% FBS, counted and centrifuged. Resuspended the cells in DMEM/F12 medium containing 5% FBS and seeded the cells at a density of $1 \times 10^5$ cells/ml. When the cell confluence reached 80%-90%, washed with PBS and digest with trypsin. Then, terminated by the DMEM/F12 medium containing 2% FBS, counted and centrifuged. Resuspended the cells in the DMEM/F12 medium containing 2% FBS and seeded at a density of $1 \times 10^5$ cells/ml. When the cell confluence reached 80%-90%, digested the cells with trypsin according to the previous steps, terminated by the DMEM/F12 medium containing 1% FBS, and carried out passage for 3-4 generations. Mixed the CD CHO medium with DMEM/F12 at a ratio of 1:1 (V/V), adjusted the final concentration to 6 mM glutamine, and adjusted the serum content to 1%. The CHO-K1 cells obtained above adapted to low serum culture were seeded into a T25 flask at a density of $3 \times 10^5$ cells/mL and were incubated in a 5% $CO_2$ incubator at 37° C. When the cell confluence reached 80-90%, digested the cells with trypsin and terminate by the mixed medium of DMEM/F12 containing 1% FBS and CD CHO medium (volume ratio 1:2), counted and centrifuged, seeded into a T25 flask at a density of $3 \times 10^5$ cells/ml, and incubated in a 5% $CO_2$ incubator at 37° C. Gradually reduced the ratio of DMEM/F12 in the mixture medium to (1:8) until the cell survival rate was more than 90%, which means that the DMEM/F12 component in the cell medium could be completely eliminated, and the CHO-K1 cell which adapted in chemical composition limitative CD CHO medium containing 1% serum was established. Then CHO-K1 was cultured in chemical composition limitative CD CHO medium containing 1% FBS. When cell confluence reached 80%-90%, washed with PBS and digested with trypsin. Then, terminated by the CD CHO medium containing 0.5% FBS, counted and centrifuged. Resuspended the cells in the CD CHO medium containing 0.5% FBS and seeded in a T25 flask at a density of $1 \times 10^5$ cells/ml. When the cell viability reached 80%-90%, washed the cells with PBS and digested with trypsin. Then, terminated by the CD CHO medium containing 0.25% FBS, counted and centrifuged. Resuspended the cells in the CD CHO medium containing 0.25% FBS and seeded at a density of $1 \times 10^5$ cells/ml. Until the cells grew healthily at this stage, started the next stage of decreasing serum concentration. After limiting dilution of CHO-K1 cells adapted to serum-free CD CHO culture, seeded into thirty 96-well plates, and adjusted the cell density to 1 cell/well. After two weeks, marked the monoclonal cells through microscopic examination. Transferred the clones with large cell area to a 24-well plate. After one week, marked the clones with high growth density and with consistent cell size through microscopic examination, and then transferred to a 6-well plate for further culture. After one week, clones that were completely suspended, less agglomerated, and had a denser cell density were marked through microscopic examination, and transferred each clone to a 100-ml triangular flask with a culture volume of 10 ml, respectively. Recorded the density and viability of each cell. CHO-K1 cells domesticated and adapted to serum-free culture were renamed CHO-BAT.

Example 2 Construction of FUT8 TALEN Recombinant Plasmid

Figure 2:
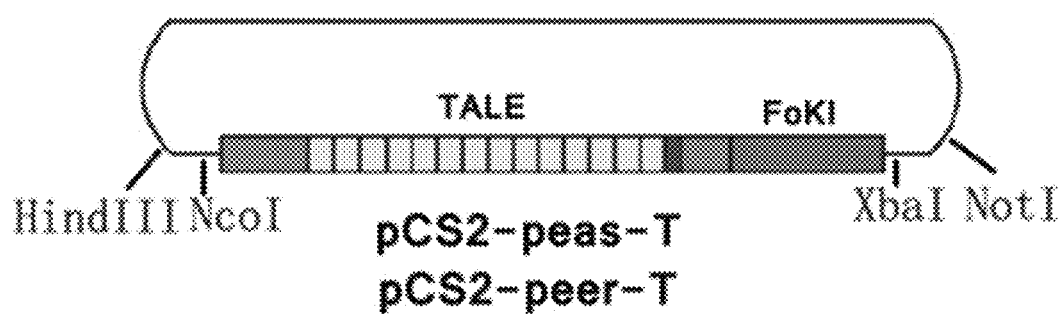
FIG. 2 shows a profile of TALEN expression plasmid pCS2-Fok1.

The complete genome sequence (NW-003613860) of CHO-K1 of Chinese hamster ovarian cancer cells was analyzed to obtain the FUT8 genome sequence (Gene ID: 100751648) and its cDNA (see Table 1, SEQ ID NO. 8) sequence. The FUT8 genome consists of 9 exons and 11 introns. As the activity center of FUT8 enzyme is composed of amino acids (underlined amino acid sequence of SEQ ID NO. 9) encoded by exon 1 (SEQ ID NO. 7), the left and right flanks of exon 1 of FUT8 gene were designed as TALEN target sequences. FUT8 TALEN protein L130P (SEQ ID NO. 10) and R184P (SEQ ID NO. 11) were designed according to the TALEN design guidelines and the gene editing mechanism. L130P and FokI endonucleases formed a fusion protein L130-FokI (SEQ ID NO. 14), which recognized the left-wing base L130PTN (SEQ ID NO. 3) in exon 1, and the corresponding nucleic acid sequence L130-FokIN of the fusion protein L130-FokI is shown in SEQ ID NO. 15 with a length of 19 bp. R184P and Fold endonucleases formed a fusion protein R184-FokI (SEQ ID NO. 16), which recognized the right-wing base R184PTN (SEQ ID NO. 4) in exon 1, and the corresponding nucleic acid sequence R184P-FokIN of the fusion protein R184P-FokI is shown in SEQ ID NO. 17 with a length of 17 bp. The plasmid vector (see FIG. 2) containing TALEN protein encoding the left-wing L130PTN and the right-wing R184PTN of the exon 1 was constructed as described in Tomas Cermak et al. (2011). The restriction endonucleases NcoI and XbaI cleavage sites were added at both ends of L130-FokIN and R184P-FokIN. Synthesized these two sequences, and cloned them into pCS2-peas-T vector using NcoI and XbaI (FIG. 2). The left-wing binding sequence and the right-wing binding sequence had a gap sequence of 19 bp in length (Space, SEQ ID NO. 5). The DNA sequencing results of the two plasmids L130N and R184N of FUT8 TALEN are shown in Table 1, SEQ ID NO. 12 and SEQNO. 13. The nucleic acid sequences such as L130N and R184N were translated into amino acids, and the amino acid sequences L130P and R184P of the corresponding sequences are shown in Table 1, SEQ ID NO. 10 and SEQ ID NO. 11.

TABLE 1

Sequence table

| | | |
|---|---|---|
| L130for | gggtagctaattgtctttcag | SEQ ID NO. 1 |
| L130rev | taaatgccactgcttctata | SEQ ID NO. 2 |
| L130PTN | tccaagattcttgcaaagct | SEQ ID NO. 3 |
| R184PTN | aatgaagacttgaggaga | SEQ ID NO. 4 |
| Space | ggagcgcttaaaacaacaa | SEQ ID NO. 5 |
| PCR product | GGGTAGCTAATTGTCTTTCAGCCTCCTGGCCAAAGATACCATGAA AGTCAACTTACGTTGTATTCTATATCTCAAACAACTCAGGGTGTT TCTTACTCTTTCCACAGCATGTAGAGCCCAGGAAGCACAGGACA AGAAAGCTGCCTCCTTGTATCACCAGGAAGATCTTTTTGTAAGAG TCATCACAGTATACCAGAGAGACTAATTTTGTCTGAAGCATCATG TGTTGAAACAACAGAAACTTATTTTCCTGTGTGGCTAACTAGAAC | SEQ ID NO. 6 |

TABLE 1-continued

Sequence table

| | | |
|---|---|---|
| | CAGAGTACAATGTTTCCAATTCTTTGAGCTCCGAGAAGACAGAA<br>GGGAGTTGAAACTCTGAAAATGCGGGCATGGACTGGTTCCTGGC<br>GTTGGATTATGCTCATTCTTTTTGCCTGGGGGACCTTATTGTTTTA<br>TATAGGTGGTCATTTGGTTCGAGATAATGACCACCCTGACCATTC<br>TAGCAGAGAACTCTCCAAGATTCTTGCAAAGCTGGAGCGCTTAA<br>AACAACAAAATGAAGACTTGAGGAGAATGGCTGAGTCTCTCCGG<br>TAGGGTTTGAAATACTCAAGGATTTGATGAAATACTGTGCTTGACC<br>TTTAGGTATAGGGTCTCAGTCTGCTGTTGAAAAATATAATTTCTA<br>CAAACCGTCTTTGTAAAATTTTAAGTATTGTAGCAGACTTTTTAA<br>AAGTCAGTGATACATCTATATAGTCAATATAGGTTTACATAGTTG<br>CAATCTTATTTTGCATATGAATCAGTATATAGAAGCAGTGGCATT<br>TA | |
| Exon1 | ATGCGGGCATGGACTGGTTCCTGGCGTTGGATTATGCTCATTCTT<br>TTTGCCTGGGGGACCTTATTGTTTTATATAGGTGGTCATTTGGTTC<br>GAGATAATGACCACCCTGACCATTCTAGCAGAGAACTCTCCAAG<br>ATTCTTGCAAAGCTGGAGCGCTTAAAACAACAAAATGAAGACTT<br>GAGGAGAATGGCTGAGTCTCTCCGG | SEQ ID<br>NO. 7 |
| FUT8 cDNA | ATGCGGGCATGGACTGGTTCCTGGCGTTGGATTATGCTCATTCTT<br>TTTGCCTGGGGGACCTTATTGTTTTATATAGGTGGTCATTTGGTTC<br>GAGATAATGACCACCCTGACCATTCTAGCAGAGAACTCTCCAAG<br>ATTCTTGCAAAGCTGGAGCGCTTAAAACAACAAAATGAAGACTT<br>GAGGAGAATGGCTGAGTCTCTCCGAATACCAGAAGGCCCTATTG<br>ATCAGGGGACAGCTACAGGAAGAGTCCGTGTTTTAGAAGAACAG<br>CTTGTTAAGGCCAAAGAACAGATTGAAAATTACAAGAAACAAGC<br>TAGGAATGATCTGGGAAAGGATCATGAAATCTTAAGGAGGAGGA<br>TTGAAAATGGAGCTAAAGAGCTCTGGTTTTTTCTACAAAGTGAAT<br>TGAAGAAATTAAAGAAATTAGAAGGAAACGAACTCCAAAGACA<br>TGCAGATGAAATTCTTTTGGATTAGGACATCATGAAAGGTCTAT<br>CATGACAGATCTATACTACCTCAGTCAAACAGATGGAGCAGGTG<br>AGTGGCGGGAAAAAGAAGCCAAAGATCTGACAGAGCTGGTCCA<br>GCGGAGAATAACATATCTGCAGAATCCCAAGGACTGCAGCAAAG<br>CCAGAAAGCTGGTATGTAATATCAACAAAGGCTGTGGCTATGGA<br>TGTCAACTCCATCATGTGGTTTACTGCTTCATGATTGCTTATGGCA<br>CCCAGCGAACACTCATCTTGGAATCTCAGAATTGGCGCTATGCTA<br>CTGGAGGATGGGAGACTGTGTTTAGACCTGTAAGTGAGACATGC<br>ACAGACAGGTCTGGCCTCTCCACTGGACACTGGTCAGGTGAAGT<br>GAAGGACAAAAATGTTCAAGTGGTCGAGCTCCCCATTGTAGACA<br>GCCTCCATCCTCGTCCTCCTTACTTACCCTTGGCTGTACCAGAAG<br>ACCTTGCAGATCGACTCCTGAGAGTCCATGGTGATCCTGCAGTGT<br>GGTGGGTATCCCAGTTTGTCAAATACTTGATCCGTCCACAACCTT<br>GGCTGGAAAGGGAAATAGAAGAAACCACCAAGAAGCTTGGCTTC<br>AAACATCCAGTTATTGGAGTCCATGTCAGACGCACTGACAAAGT<br>GGGAACAGAAGCAGCCTTCCATCCCATTGAGGAATACATGGTAC<br>ACGTTGAAGAACATTTTCAGCTTCTCGAACGCAGAATGAAAGTG<br>GATAAAAAAGAGTGTATCTGGCCACTGATGACCCTTCTTTGTTA<br>AAGGAGGCAAAGACAAAGTACTCCAATTATGAATTTATTAGTGA<br>TAACTCTATTTCTTGGTCAGCTGGACTACACAACCGATACACAGA<br>AAATTCACTTCGGGGCGTGATCCTGGATATACACTTTCTCTCCCA<br>GGCTGACTTCCTTGTGTGTACTTTTTCATCCCAGGTCTGTAGGGTT<br>GCTTATGAAATCATGCAAACACTGCATCCTGATGCCTCTGCAAA<br>TTCCATTCTTTAGATGACATCTACTATTTTGGAGGCCAAAATGCC<br>CACAACCAGATTGCAGTTTATCCTCACCAACCTCGAACTAAAGA<br>GGGAAATCCCCATGGAACCTGGAGATATCATTGGTGTGGCTGGAA<br>ACCATTGGAATGGTTACTCTAAAGGTGTCAACAGAAAACTAGGA<br>AAAACAGGCCTGTACCCTTCCTACAAAGTCCGAGAGAAGATAGA<br>AACAGTCAAATACCCTACATATCCTGAAGCTGAAAATAG | SEQ ID<br>NO. 8 |
| FUT8 protein | MRAWTGSWRWIMLILFAWGTLLFYIGGHLVRDNDHPDHSSRELSKI<br>LAKLERLKQQNEDLRRMAESLRIPEGPIDQGTATGRVRVLEEQLVK<br>AKEQIENYKKQARNDLGKDHEILRRRIENGAKELWFFLQSELKKLK<br>KLEGNELQRHADEILLDLGHHERSIMTDLYYLSQTDGAGEWREKEA<br>KDLTELVQRRITYLQNPKDCSKARKLVCNINKGCGYGCQLHHVVY<br>CFMIAYGTQRTLILESQNWRYATGGWETVFRPVSETCTDRSGLSTG<br>HWSGEVKDKNVQVVELPIVDSLHPRPPYLPLAVPEDLADRLLRVHG<br>DPAVWWVSQFVKYLIRPQPWLEREIEETTKKLGFKHPVIGVHVRRT<br>DKVGTEAAFHPIEEYMVHVEEHFQLLERRMKVDKKRVYLATDDPS<br>LLKEAKTKYSNYEFISDNSISWSAGLHNRYTENSLRGVILDIHFLSQA<br>DFLVCTFSSQVCRVAYEIMQTLHPDASANFHSLDDIYYFGGQNAHN<br>QIAVYPHQPRTKEEIPMEPGDIIGVAGNHWNGYSKGVNRKLGKTGL<br>YPSYKVREKIETVKYPTYPEAEK | SEQ ID<br>NO. 9 |
| L130P | LTPEQVVAIASHDGGKQALETVQRLLPVLCQAHGLTPAQVVAIASH<br>DGGKQALETVQRLLPVLCQAHGLTPAQVVAIASNIGGKQALETVQR<br>LLPVLCQAHGLTPDQVVAIASNIGGKQALETVQRLLPVLCQAHGLT<br>PDQVVAIASNNGGKQALETVQRLLPVLCQAHGLTPDQVVAIASNIG<br>GKQALETVQRLLPVLCQAHGLTPDQVVAIASNGGGKQALETVQRL | SEQ ID<br>NO. 10 |

TABLE 1-continued

Sequence table

| | | |
|---|---|---|
| | LPVLCQAHGLTPAQVVAIASNGGGKQALETVQRLLPVLCQAHGLTP<br>AQVVAIASHDGGKQALETVQRLLPVLCQAHGLTPAQVVAIASNGG<br>GKQALETVQRLLPVLCQAHGLTPAQVVAIASNGGGKQALETVQRL<br>LPVLCQAHGLTPAQVVAIASNNGGKQALETVQRLLPVLCQAHGLTP<br>DQVVAIASHDGGKQALETVQRLLPVLCQAHGLTPAQVVAIASNIGG<br>KQALETVQRLLPVLCQAHGLTPDQVVAIASNIGGKQALETVQRLLP<br>VLCQAHGLTPDQVVAIASNIGGKQALETVQRLLPVLCQAHGLTPDQ<br>VVAIASNNGGKQALETVQRLLPVLCQAHGLTPDQVVAIASHDGGK<br>QALETVQRLLPVLCQAHGLTPAQVVAIASNGGGRPALESIVAQLSRP<br>DPALAAL | |
| R184P | LTPEQVVAIASHDGGKQALETVQRLLPVLCQAHGLTPAQVVAIASNG<br>GGKQALETVQRLLPVLCQAHGLTPAQVVAIASHDGGKQALETVQRL<br>LPVLCQAHGLTPAQVVAIASHDGGKQALETVQRLLPVLCQAHGLTP<br>AQVVAIASNGGGKQALETVQRLLPVLCQAHGLTPAQVVAIASHDGG<br>KQALETVQRLLPVLCQAHGLTPAQVVAIASNIGGKQALETVQRLLPV<br>LCQAHGLTPDQVVAIASNIGGKQALETVQRLLPVLCQAHGLTPDQV<br>VAIASNNGGKQALETVQRLLPVLCQAHGLTPDQVVAIASNGGGKQA<br>LETVQRLLPVLCQAHGLTPAQVVAIASHDGGKQALETVQRLLPVLC<br>QAHGLTPAQVVAIASNGGGKQALETVQRLLPVLCQAHGLTPAQVVAI<br>ASNGGGKQALETVQRLLPVLCQAHGLTPAQVVAIASHDGGKQALET<br>VQRLLPVLCQAHGLTPAQVVAIASNIGGKQALETVQRLLPVLCQAH<br>GLTPDQVVAIASNGGGKQALETVQRLLPVLCQAHGLTPAQVVAIASN<br>GGGRPALESIVAQLSRPDPALAAL | SEQ ID<br>NO. 11 |
| L130N | CTGACCCCGGAGCAGGTGGTGGCCATCGCTAGTCATGACGGTGGC<br>AAACAGGCTCTTGAGACCGTCCAACGCCTTCTACCAGTTCTCTGT<br>CAAGCCCACGGACTAACCCCAGCGCAAGTTGTAGCGATTGCTAGT<br>CATGACGGTGGCAAACAGGCTCTTGAGACCGTCCAACGCCTTCTA<br>CCAGTTCTCTGTCAAGCCCACGGACTAACCCCAGCGCAAGTTGTA<br>GCGATTGCTAGTAATATTGGTGGCAAACAGGCACTTGAGACGGTT<br>CAGCGCCTCCTTCCAGTTCTTTGTCAAGCTCACGGACTCACCCCA<br>GATCAAGTTGTAGCGATTGCTAGTAATATTGGTGGCAAACAGGCA<br>CTTGAGACGGTTCAGCGCCTCCTTCCAGTTCTTTGTCAAGCTCAC<br>GGACTCACCCCAGATCAAGTTGTAGCGATTGCTAGTAACAATGGT<br>GGCAAACAGGCTCTCGAAACCGTACAACGACTCCTCCCAGTTCTC<br>TGTCAAGCCCACGGACTAACTCCTGATCAAGTTGTAGCGATTGCT<br>AGTAATATTGGTGGCAAACAGGCACTTGAGACGGTTCAGCGCCTC<br>CTTCCAGTTCTTTGTCAAGCTCACGGACTCACCCCAGATCAAGTT<br>GTAGCGATTGCTAGTAATGGGGTGGCAAACAGGCTCTTGAAACC<br>GTGCAACGACTGCTCCCAGTTCTCTGTCAAGCCCACGGCCTCACC<br>CCGGCGCAAGTTGTAGCGATTGCTAGTAATGGGGGTGGCAAACAG<br>GCTCTTGAAACCGTGCAACGACTGCTCCCAGTTCTCTGTCAAGCC<br>CACGGCCTCACCCCGGCGCAAGTTGTAGCGATTGCTAGTCATGAC<br>GGTGGCAAACAGGCTCTTGAGACCGTCCAACGCCTTCTACCAGTT<br>CTCTGTCAAGCCCACGGACTAACCCCAGCGCAAGTTGTAGCGATT<br>GCTAGTAATGGGGTGGCAAACAGGCTCTTGAAACCGTGCAACG<br>ACTGCTCCCAGTTCTCTGTCAAGCCCACGGCCTCACCCCGGCGCA<br>AGTTGTAGCGATTGCTAGTAATGGGGGTGGCAAACAGGCTCTTGA<br>AACCGTGCAACGACTGCTCCCAGTTCTCTGTCAAGCCCACGGCCT<br>CACCCCGGCGCAAGTTGTAGCGATTGCTAGTAACAATGGTGGCAA<br>ACAGGCTCTCGAAACCGTACAACGACTCCTCCCAGTTCTCTGTCA<br>AGCCCACGGACTAACTCCTGATCAAGTTGTAGCGATTGCTAGTCAT<br>GACGGTGGCAAACAGGCTCTTGAGACCGTCCAACGCCTTCTACC<br>AGTTCTCTGTCAAGCCCACGGACTAACCCCAGCGCAAGTTGTAGC<br>GATTGCTAGTAATATTGGTGGCAAACAGGCACTTGAGACGGTTCA<br>GCGCCTCCTTCCAGTTCTTTGTCAAGCTCACGGACTCACCCCAGA<br>TCAAGTTGTAGCGATTGCTAGTAATATTGGTGGCAAACAGGCACTT<br>GAGACGGTTCAGCGCCTCCTTCCAGTTCTTTGTCAAGCTCACGGA<br>CTCACCCCAGATCAAGTTGTAGCGATTGCTAGTAATATTGGTGGCA<br>AACAGGCACTTGAGACGGTTCAGCGCCTCCTTCCAGTTCTTTGTC<br>AAGCTCACGGACTCACCCCAGATCAAGTTGTAGCGATTGCTAGTA<br>ACAATGGTGGCAAACAGGCTCTCGAAACCGTACAACGACTCCTC<br>CCAGTTCTCTGTCAAGCCCACGGACTAACTCCTGATCAAGTTGTA<br>GCGATTGCTAGTCATGACGGTGGCAAACAGGCTCTTGAGACCGTC<br>CAACGCCTTCTACCAGTTCTCTGTCAAGCCCACGGACTAACCCCA<br>GCGCAAGTTGTAGCGATTGCTAGTAATGGCGGCGGTCGACCGGCG<br>CTGGAGAGCATTGTTGCCCAGTTATCTCGCCCTGATCCGGCGTTGG<br>CCGCGTTG | SEQ ID<br>NO. 12 |
| R184N | CTGACCCCGGAGCAGGTGGTGGCCATCGCTAGTCATGACGGTGGC<br>AAACAGGCTCTTGAGACCGTCCAACGCCTTCTACCAGTTCTCTGT<br>CAAGCCCACGGACTAACCCCAGCGCAAGTTGTAGCGATTGCTAGT<br>AATGGGGGTGGCAAACAGGCTCTTGAAACCGTGCAACGACTGCT<br>CCCAGTTCTCTGTCAAGCCCACGGCCTCACCCCGGCGCAAGTTGT<br>AGCGATTGCTAGTCATGACGGTGGCAAACAGGCTCTTGAGACCGT<br>CCAACGCCTTCTACCAGTTCTCTGTCAAGCCCACGGACTAACCCC<br>AGCGCAAGTTGTAGCGATTGCTAGTCATGACGGTGGCAAACAGGC | SEQ ID<br>NO. 13 |

TABLE 1-continued

Sequence table

|  |  |  |
|---|---|---|
|  | TCTTGAGACCGTCCAACGCCTTCTACCAGTTCTCTGTCAAGCCCA<br>CGGACTAACCCCAGCGCAAGTTGTAGCGATTGCTAGTAATGGGGG<br>TGGCAAACAGGCTCTTGAAACCGTGCAACGACTGCTCCCAGTTCT<br>CTGTCAAGCCCACGGCCTCACCCCGGCGCAAGTTGTAGCGATTGC<br>TAGTCATGACGGTGGCAAACAGGCTCTTGAGACCGTCCAACGCCT<br>TCTACCAGTTCTCTGTCAAGCCCACGGACTAACCCCAGCGCAAGT<br>TGTAGCGATTGCTAGTAATATTGGTGGCAAACAGGCACTTGAGAC<br>GGTTCAGCGCCTCCTTCCAGTTCTTTGTCAAGCTCACGGACTCAC<br>CCCAGATCAAGTTGTAGCGATTGCTAGTAATATTGGTGGCAAACAG<br>GCACTTGAGACGGTTCAGCGCCTCCTTCCAGTTCTTTGTCAAGCT<br>CACGGACTCACCCCAGATCAAGTTGTAGCGATTGCTAGTAACAAT<br>GGTGGCAAACAGGCTCTCGAAACCGTACAACGACTCCTCCCAGT<br>TCTCTGTCAAGCCCACGGACTAACTCCTGATCAAGTTGTAGCGATT<br>GCTAGTAATGGGGTGGCAAACAGGCTCTTGAAACCGTGCAACG<br>ACTGCTCCCAGTTCTCTGTCAAGCCCACGGCCTCACCCCGGCGCA<br>AGTTGTAGCGATTGCTAGTCATGACGGTGGCAAACAGGCTCTTGA<br>GACCGTCCAACGCCTTCTACCAGTTCTCTGTCAAGCCCACGGACT<br>AACCCCAGCGCAAGTTGTAGCGATTGCTAGTAATGGGGTGGCAA<br>ACAGGCTCTTGAAACCGTGCAACGACTGCTCCCAGTTCTCTGTCA<br>AGCCCACGGCCTCACCCCGGCGCAAGTTGTAGCGATTGCTAGTAA<br>TGGGGGTGGCAAACAGGCTCTTGAAACCGTGCAACGACTGCTCC<br>CAGTTCTCTGTCAAGCCCACGGCCTCACCCCGGCGCAAGTTGTAG<br>CGATTGCTAGTCATGACGGTGGCAAACAGGCTCTTGAGACCGTCC<br>AACGCCTTCTACCAGTTCTCTGTCAAGCCCACGGACTAACCCCAG<br>CGCAAGTTGTAGCGATTGCTAGTAATATTGGTGGCAAACAGGCAC<br>TTGAGACGGTTCAGCGCCTCCTTCCAGTTCTTTGTCAAGCTCACG<br>GACTCACCCCAGATCAAGTTGTAGCGATTGCTAGTAATGGGGGTG<br>GCAAACAGGCTCTTGAAACCGTGCAACGACTGCTCCCAGTTCTCT<br>GTCAAGCCCACGGCCTCACCCCGGCGCAAGTTGTAGCGATTGCTA<br>GTAATGGCGGCGGTCGACCGGCGCTGGAGAGCATTGTTGCCCAGT<br>TATCTCGCCCTGATCCGGCGTTGGCCGCGTTG |  |
| L130P-FokI | MAPKKKRKVYPYDVPDYAGYPYDVPDYAGSYPYDVPDYAAHGTV<br>DLRTLGYSQQQQEKIKPKVRSTVAQHHEALVGHGFTHAHIVALSQHP<br>AALGTVAVKYQDMIAALPEATHEAIVGVGKQWSGARALEALLTVAG<br>ELRGPPLQLDTGQLLKIAKRGGVTAVEAVHAWRNALTGAPLNLTPEQ<br>VVAIASHDGGKQALETVQRLLPVLCQAHGLTPAQVVAIASHDGGKQ<br>ALETVQRLLPVLCQAHGLTPAQVVAIASNIGGKQALETVQRLLPVLC<br>QAHGLTPDQVVAIASNIGGKQALETVQRLLPVLCQAHGLTPDQVVAI<br>ASNNGGKQALETVQRLLPVLCQAHGLTPDQVVAIASNGGGKQALET<br>VQRLLPVLCQAHGLTPDQVVAIASNGGGKQALETVQRLLPVLCQAH<br>GLTPAQVVAIASNGGGKQALETVQRLLPVLCQAHGLTPAQVVAIASH<br>DGGKQALETVQRLLPVLCQAHGLTPAQVVAIASNGGGKQALETVQR<br>LLPVLCQAHGLTPAQVVAIASNGGGKQALETVQRLLPVLCQAHGLT<br>PAQVVAIASNGGGKQALETVQRLLPVLCQAHGLTPDQVVAIASHDG<br>GKQALETVQRLLPVLCQAHGLTPAQVVAIASNIGGKQALETVQRLLP<br>VLCQAHGLTPDQVVAIASNIGGKQALETVQRLLPVLCQAHGLTPDQ<br>VVAIASNIGGKQALETVQRLLPVLCQAHGLTPDQVVAIASNNGGKQ<br>ALETVQRLLPVLCQAHGLTPDQVVAIASHDGGKQALETVQRLLPVL<br>CQAHGLTPAQVVAIASNGGGRPALESIVAQLSRPDPALAALTNDHLVA<br>LACLGGRPALDAVKKGLPHAPALIKRTNRRIPERTSHRVAGSQLVKSE<br>LEEKKSELRHKLKYVPHEYIELIEIARNPTQDRILEMKVMEIMMKVY<br>GYRGEHLGGSRKPDGAIYTVGSPIDYGVIVDTKAYSGGYNLPIGQAR<br>EMQRYVEENQTRNKHINPNEWWKVYPSSVTEFKFLFVSGHFKGNY<br>KAQLTRLNHITNCNGAVLSVEELLIGGEMIKAGTLTLEEVRRKFNNG<br>EINF* | SEQ ID<br>NO. 14 |
| L130P-<br>FokIN | atggctccaaagaagaagcgtaaggtatacccatacgatgttcctgactatgcgggctatccctatgacgtcc<br>cggactatgcaggatcgtatccatatgacgttccagattacgctgctcatggtaccgtggatctacgcacgct<br>cggctacagccagcagcaacaggagaagatcaaaccgaaggttcgttcgacagtggcgcagcaccacga<br>ggcactggtcggccacgggtttacacacgcacatcgttgcgctcagccaacaccggcagcgttaggg<br>accgtcgctgtcaagtatcaggacatgatcgcagcgttgccagaggcgacacacgaagcgatcgttggcgt<br>cggcaaacagtggtccggcgcacgcgctctggaggccttgctcacggtggcgggagagttgagaggtcc<br>accgttacagttggacacaggccaacttctcaagattgcaaaacgtggcggcgtgaccgcagtggaggca<br>gtgcatgcatggcgcaatgcactgacgggtgccccccctgaacctgaccccggagcaggtggtggccatcg<br>cTAGTCATGACGGTGGCAAACAGGCTCTTGAGACCGTCCAACGCC<br>TTCTACCAGTTCTCTGTCAAGCCCACGGACTAACCCCAGCGCAAG<br>TTGTAGCGATTGCTAGTCATGACGGTGGCAAACAGGCTCTTGAGA<br>CCGTCCAACGCCTTCTACCAGTTCTCTGTCAAGCCCACGGACTAA<br>CCCCAGCGCAAGTTGTAGCGATTGCTAGTAATATTGGTGGCAAAC<br>AGGCACTTGAGACGGTTCAGCGCCTCCTTCCAGTTCTTTGTCAAG<br>CTCACGGACTCACCCCAGATCAAGTTGTAGCGATTGCTAGTAATAT<br>TGGTGGCAAACAGGCACTTGAGACGGTTCAGCGCCTCCTTCCAGT<br>TCTTTGTCAAGCTCACGGACTCACCCCAGATCAAGTTGTAGCGAT<br>TGCTAGTAACAATGGTGGCAAACAGGCTCTCGAAACCGTACAACG<br>ACTCCTCCCAGTTCTCTGTCAAGCCCACGGACTAACTCCTGATCA<br>AGTTGTAGCGATTGCTAGTAATATTGGTGGCAAACAGGCACTTGA<br>GACGGTTCAGCGCCTCCTTCCAGTTCTTTGTCAAGCTCACGGACT | SEQ ID<br>NO. 15 |

TABLE 1-continued

Sequence table

```
                 CACCCCAGATCAAGTTGTAGCGATTGCTAGTAATGGGGGTGGCAA
                 ACAGGCTCTTGAAACCGTGCAACGACTGCTCCCAGTTCTCTGTCA
                 AGCCCACGGCCTCACCCCGGCGCAAGTTGTAGCGATTGCTAGTAA
                 TGGGGGTGGCAAACAGGCTCTTGAAACCGTGCAACGACTGCTCC
                 CAGTTCTCTGTCAAGCCCACGGCCTCACCCCGGCGCAAGTTGTAG
                 CGATTGCTAGTCATGACGGTGGCAAACAGGCTCTTGAGACCGTCC
                 AACGCCTTCTACCAGTTCTCTGTCAAGCCCACGGACTAACCCCAG
                 CGCAAGTTGTAGCGATTGCTAGTAATGGGGGTGGCAAACAGGCTC
                 TTGAAACCGTGCAACGACTGCTCCCAGTTCTCTGTCAAGCCCACG
                 GCCTCACCCCGGCGCAAGTTGTAGCGATTGCTAGTAATGGGGGTG
                 GCAAACAGGCTCTTGAAACCGTGCAACGACTGCTCCCAGTTCTCT
                 GTCAAGCCCACGGCCTCACCCCGGCGCAAGTTGTAGCGATTGCTA
                 GTAACAATGGTGGCAAACAGGCTCTCGAAACCGTACAACGACTC
                 CTCCCAGTTCTCTGTCAAGCCCACGGACTAACTCCTGATCAAGTT
                 GTAGCGATTGCTAGTCATGACGGTGGCAAACAGGCTCTTGAGACC
                 GTCCAACGCCTTCTACCAGTTCTCTGTCAAGCCCACGGACTAACC
                 CCAGCGCAAGTTGTAGCGATTGCTAGTAATATTGGTGGCAAACAG
                 GCACTTGAGACGGTTCAGCGCCTCCTTCCAGTTCTTTGTCAAGCT
                 CACGGACTCACCCCAGATCAAGTTGTAGCGATTGCTAGTAATATTG
                 GTGGCAAACAGGCACTTGAGACGGTTCAGCGCCTCCTTCCAGTTC
                 TTTGTCAAGCTCACGGACTCACCCCAGATCAAGTTGTAGCGATTG
                 CTAGTAATATTGGTGGCAAACAGGCACTTGAGACGGTTCAGCGCC
                 TCCTTCCAGTTCTTTGTCAAGCTCACGGACTCACCCCAGATCAAG
                 TTGTAGCGATTGCTAGTAACAATGGTGGCAAACAGGCTCTCGAAA
                 CCGTACAACGACTCCTCCCAGTTCTCTGTCAAGCCCACGGACTAA
                 CTCCTGATCAAGTTGTAGCGATTGCTAGTCATGACGGTGGCAAAC
                 AGGCTCTTGAGACCGTCCAACGCCTTCTACCAGTTCTCTGTCAAG
                 CCCACGGACTAACCCCAGCGCAAGTTGTAGCGATTGCTAGTAATG
                 GCggcggtcgaccggcgctggagagcattgttgcccagttatctcgccctgatccggcgttggccgcgtt
                 gaccaacgaccacctcgtcgccttggcctgcctcggcggacgtcctgcgctggatgcagtgaaaaaggga
                 ttgccgcacgcgccggccttgatcaaaagaaccaatcgccgtattcccgaacgcacatcccatcgcgttgcc
                 ggatcccaactagtcaaaagtgaactggaggagaagaaatctgaacttcgtcataaattgaaatatgcctc
                 atgaatatattgaattaattgaaattgccagaaatcccactcaggatagaattcttgaaatgaaggtaatggaat
                 tattatgaaagtttatgatatagaggtgagcatagggtggatcaaggaaaccggacggagcaatttatact
                 gtcggatctcctattgattacggtgtgatcgtggatactaaggcttatagcggaggttataatctgccaattggc
                 caagcacgagaaatgcaacgatatgtcgaagaaaatcaaacacgaaacaaacatatcaaccctaatgaatg
                 gtggaaagtctatccatcttctgtaacggaatttaagttttttatttgtgagtggtcactttaaaggaaactacaaag
                 ctcagcttacacgattaaatcatatcactaattgtaatggagctgttcttagtgtagaagagcttttaattggtgga
                 gaaatgattaaagccggcacattaaccttagaggaagtgagacggaaatttaataacggcgagatcaaactttt
```

R184P-FokI

```
MAPKKKRKVYPYDVPDYAGYPYDVPDYAGSYPYDVPDYAAHGTV
DLRTLGYSQQQQEKIKPKVRSTVAQHHEALVGHGFTHAHIVALSQHP
AALGTVAVKYQDMIAALPEATHEAIVGVGKQWSGARALEALLTVAG
ELRGPPLQLDTGQLLKIAKRGGVTAVEAVHAWRNALTGAPLNLTPEQ
VVAIASHDGGKQALETVQRLLPVLCQAHGLTPAQVVAIASNGGGKQ
ALETVQRLLPVLCQAHGLTPAQVVAIASHDGGKQALETVQRLLPVL
CQAHGLTPAQVVAIASHDGGKQALETVQRLLPVLCQAHGLTPAQVV
AIASNGGGKQALETVQRLLPVLCQAHGLTPAQVVAIASHDGGKQAL
ETVQRLLPVLCQAHGLTPAQVVAIASNIGGKQALETVQRLLPVLCQA
HGLTPDQVVAIASNIGGKQALETVQRLLPVLCQAHGLTPDQVAIAS
NNGGKQALETVQRLLPVLCQAHGLTPDQVVAIASNGGGKQALETV
QRLLPVLCQAHGLTPDQVVAIASHDGGKQALETVQRLLPVLCQAHG
LTPAQVVAIASNGGGKQALETVQRLLPVLCQAHGLTPAQVVAIASNG
GGKQALETVQRLLPVLCQAHGLTPAQVVAIASHDGGKQALETVQRL
LPVLCQAHGLTPAQVVAIASNIGGKQALETVQRLLPVLCQAHGLTPD
QVVAIASNGGGKQALETVQRLLPVLCQAHGLTPAQVVAIASNGGGR
PALESIVAQLSRPDPALAALTNDHLVALACLGGRPALDAVKKGLPHA
PALIKRTNRRIPERTSHRVAGSQLVKSELEEKKSELRHKLKYVPHEYIE
LIEIARNPTQDRILEMKVMEFFMKVYGYRGEHLGGSRKPDGAIYTV
GSPIDYGVIVDTKAYSGGYNLPIGQADMQSYVEENQTRNKHINPN
EWWKVYPSSVTEFKFLFVSGHFKGNYKAQLTRLNHITNCNGAVLSV
EELLIGGEMIKAGTLTLEEVRRKFNNGEINF*
```

SEQ ID NO. 16

R184P-FokIN

```
cgccattctgcctggggacgtcggagcaagcttgatttaggtgacactatagaatacaagctacttgttcttttt
gcaggatctgccaccatggctcaaaagaagaagcgtaaggtatatccatacgatgttcctgactatgcgggg
ctatcccatatgacgtcccggactatgcaggatcgtatccatatgacgttccagattacgctgctcatggtaccg
tggatctacgcacgctcggctacagccagcagcaacaggagaagatcaaaccgaaggttcgttcgacagt
ggcgcagcaccacgaggcactggtcggccacgggtttacacacgcgcacatcgttgcgctcagccaaca
cccgcagcgttagggaccgtcgctgtcaagtatcaggacatgatcgcagcgttgccagaggcgacacac
gaagcgatcgttggcgtcggcaaacagtggtccggcgcacgcgctctggaggccttgctcacggttgacgg
gagagttgagaggtccaccgttacagaggacacaggccaacttctcaagattgcaaaacgtgcggcgtg
accgcagtggaggcagtgcatgcatggcgcaatgcactgacgggtgccccctgaacctgaccccggag
caggtggtggcccatcgcTAGTCATGACGGTGGCAAACAGGCTCTTGAGACC
GTCCAACGCCTTCTACCAGTTCTCTGTCAAGCCCACGGACTAACC
CCAGCGCAAGTTGTAGCGATTGCTAGTAATGGGGGTGGCAAACAG
GCTCTTGAAACCGTGCAACGACTGCTCCCAGTTCTCTGTCAAGCC
CACGGCCTCACCCCGGCGCAAGTTGTAGCGATTGCTAGTCATGAC
GGTGGCAAACAGGCTCTTGAGACCGTCCAACGCCTTCTACCAGTT
```

SEQ ID NO. 17

TABLE 1-continued

Sequence table

CTCTGTCAAGCCCACGGACTAACCCCAGCGCAAGTTGTAGCGATT
GCTAGTCATGACGGTGGCAAACAGGCTCTTGAGACCGTCCAACG
CCTTCTACCAGTTCTCTGTCAAGCCCACGGACTAACCCCAGCGCA
AGTTGTAGCGATTGCTAGTAATGGGGGTGGCAAACAGGCTCTTGA
AACCGTGCAACGACTGCTCCCAGTTCTCTGTCAAGCCCACGGCCT
CACCCCGGCGCAAGTTGTAGCGATTGCTAGTCATGACGGTGGCAA
ACAGGCTCTTGAGACCGTCCAACGCCTTCTACCAGTTCTCTGTCA
AGCCCACGGACTAACCCCAGCGCAAGTTGTAGCGATTGCTAGTAA
TATTGGTGGCAAACAGGCACTTGAGACGGTTCAGCGCCTCCTTCC
AGTTCTTTGTCAAGCTCACGGACTCACCCCAGATCAAGTTGTAGC
GATTGCTAGTAATATTGGTGGCAAACAGGCACTTGAGACGGTTCA
GCGCCTCCTTCCAGTTCTTTGTCAAGCTCACGGACTCACCCCAGA
TCAAGTTGTAGCGATTGCTAGTAACAATGGTGGCAAACAGGCTCT
CGAAACCGTACAACGACTCCTCCCAGTTCTCTGTCAAGCCCACGG
ACTAACTCCTGATCAAGTTGTAGCGATTGCTAGTAATGGGGGTGGC
AAACAGGCTCTTGAAACCGTGCAACGACTGCTCCCAGTTCTCTGT
CAAGCCCACGGCCTCACCCCGGCGCAAGTTGTAGCGATTGCTAGT
CATGACGGTGGCAAACAGGCTCTTGAGACCGTCCAACGCCTTCTA
CCAGTTCTCTGTCAAGCCCACGGACTAACCCCAGCGCAAGTTGTA
GCGATTGCTAGTAATGGGGGTGGCAAACAGGCTCTTGAAACCGTG
CAACGACTGCTCCCAGTTCTCTGTCAAGCCCACGGCCTCACCCCG
GCGCAAGTTGTAGCGATTGCTAGTAATGGGGGTGGCAAACAGGCT
CTTGAAACCGTGCAACGACTGCTCCCAGTTCTCTGTCAAGCCCAC
GGCCTCACCCCGGCGCAAGTTGTAGCGATTGCTAGTCATGACGGT
GGCAAACAGGCTCTTGAGACCGTCCAACGCCTTCTACCAGTTCTC
TGTCAAGCCCACGGACTAACCCCAGCGCAAGTTGTAGCGATTGCT
AGTAATATTGGTGGCAAACAGGCACTTGAGACGGTTCAGCGCCTC
CTTCCAGTTCTTTGTCAAGCTCACGGACTCACCCCAGATCAAGTT
GTAGCGATTGCTAGTAATGGGGGTGGCAAACAGGCTCTTGAAACC
GTGCAACGACTGCTCCCAGTTCTCTGTCAAGCCCACGGCCTCACC
CCGGCGCAAGTTGTAGCGATTGCTAGTAATGGCggcggtcgaccggcgctg
gagagcattgttgcccagttatctcgccctgatccggcgttggccgcgttgaccaacgaccacctcgtcgcct
tggcctgcctcggcggacgtcctgcgctggatgcagtgaaaaggggattgccgcacgcgccggccttgat
caaaagaaccaatcgccgtattcccgaacgcacatcccatcgcgttgccggatcccaactagtcaaaagtga
actggaggagaagaaatctgaacttcgtcataaattgaaatatgtgcctcatgaatatattgaattaattgaaatt
gccagaaatcccactcaggatagaattcttgaaatgaaggtaatgaattttttatgaaagttatggatataga
ggtgagcatttgggtggatcaaggaaaccggacggagcaatttatactgtcggatctcctattgattacggtgt
gatcgtggatactaaagcttatagcggaggttataatctgccaattggccaagcagatgccatgcaaagctat
gtcgaagaaaatcaaacacgaaacaaacatatcaacccctaatgaatggtggaaagtctatccatcttctgtaa
cggaatttaagatttatagtgagtggtcactttaaaggaaactacaaagctcagcttacacgattaaatcatatc
actaattgtaatggagctgttcttagtgtagaagagcttttaattggtggagaaatgattaaagccggcacatta
accttagaggaagtgagacggaaatttaataacggcgagataaacttttaatctagaactatagtgagtcgtat
tacgtagatccagacatgataagatacattgatgagtttggacaaaccacaactagaatgcagtgaaaaaaat
gctttatttgtgaaatttgtgatgctattgcttttatttgtaaccattataagctgcaataaacaagttaacaacaaca
attgcattcattttatgtttcaggttcaggggggaggtgtgggaggttttttaattcgcggccgcggcgccaatgc
attgggcccggtacgtacccagctttttgttccctttagtgagggtaattgcgcgcttggcgtaatcatggtcat
agctgtttcctgtgtgaaattgttatccgctcacaattccacacaacatacgagccggaagcataaagtgtaaa
gcctggggtgcctaatgagtgagctaactcacattaattgcgttgcgctcactgcccgctttccagtcgggaa
acctgtcgtgccagctgcattaatgaatcggccaacgcgcggggagaggcggtttgcgtattgggcgctctt
ccgcttcctcgctcactgactcgctgcgctcggtcgttcggctgcggcgagcggtatcagctcactcaaagg
cggtaatacggttatccacagaatcaggggataacgcaggaaagaacatgtgagcaaaaggccagcaaaa
ggccaggaaccgtaaaaaggccgcgttgctggcgtttttccataggctccgcccccctgacgagcatcaca
aaaatcgacgctcaagtcagaggtggcgaaacccgacaggactataaagataccaggcgtttccccctgg
aagctccctcgtgcgctctcctgttccgaccctgccgcttaccggatacctgtccgcctttctcccttcgggaa
gcgtggcgctttctcatagctcacgctgtaggtatctcagttcggtgtaggtcgttcgctccaagctgggctgt
gtgcacgaaccccccgttcagcccgaccgctgcgccttatccggtaactatcgtcttgagtccaacccggta
agacacgacttatcgccactggcagcagccactggtaacaggattagcagagcgaggtatgtaggcggtg
ctacagagttcttgaagtggtggcctaactacggctacactagaaggacagtatttggtatctgcgctctgctg
aagccagttaccttcggaaaaagagttggtagctcttgatccggcaaacaaaccaccgctggtagcggtggt
ttttttgtttgcaagcagcagattacgcgcagaaaaaaaggatctcaagaagatcctttgatcttttctacgggg
tctgacgctcagtggaacgaaaactcacgttaagggattttggtcatgagattatcaaaaaggatcttcaccta
gatccttttaaattaaaaatgaagttttaaatcaatctaaagtatatatgagtaaacttggtctgacagttaccaat
gcttaatcagtgaggcacctatctcagcgatctgtctatttcgttcatccatagttgcctgactccccgtcgtgta
gataactacgatacgggagggcttaccatctggccccagtgctgcaatgataccgcgagacccacgctcac
cggctccagatttatcagcaataaaccagccagccggaagggccgagcagaagtggtcctgcaacttta
tccgcctccatccagtctattaattgttgccgggaagctagagtaagtagttcgccagttaatagtagcgcaac
gttgttgccattgctacaggcatcgtggtgtcacgctcgtcgtttggtatggcttcattcagctccggttcccaa
cgatcaaggcgagttacatgatccccatgttgtgcaaaaaagcggttagctccttcggtcctccgatcgttgt
cagaagtaagttggccgcagtgttatcactcatggttatggcagcactgcataattctcttactgtcatgccatc
cgtaagatgcttttctgtgactggtgagtactcaaccaagtcattctgagaatagtgtatgcggcgaccgagtt
gctcttgcccggcgtcaatacgggataataccgcgccacatagcagaactttaaaagtgctcatcattggaaa
acgttcttcggggcgaaaactctcaaggatcttaccgctgttgagatccagttcgatgtaacccactcgtgcac
ccaactgatcttcagcatcttttactttcaccagcgtttctgggtgagcaaaaacaggaaggcaaaatgccgc
aaaaaagggaataagggcgacacggaaatgttgaatactcatactcttcctttttcaatattattgaagcatttat
cagggttattgtctcatgagcggatacatatttgaatgtatttagaaaaataaacaaataggggttccgcgcac
atttccccgaaaagtgccacctaaattgtaagcgttaatattttgttaaaattcgcgttaaatttttgttaaatcagc
tcattttttaaccaataggccgaaatcggcaaaatcccttataaatcaaaagaatagaccgagatagggttgag
tgttgttccagtttggaacaagagtccactattaaagaacgtggactccaacgtcaaagggcgaaaaaccgt TABLE 1-continued Sequence table

```
ctatcagggcgatggcccactacgtgaaccatcaccctaatcaagttttttggggtcgaggtgccgtaaagca
ctaaatcggaaccctaaaggagccccccgatttagagcttgacggggaaagccggcgaacgtggcgaga
aggaagggaagaaagcgaaaggagcgggcgctagggcgctgcaagtgtagcggtcacgctgcgcg
taaccaccacacccgccgcgcttaatgcgccgctacagggcgcgtcccattcgccattcaggctgcgcaac
tgttgggaagggcgatcggtgcgggcctcttcgctattacgccagtcgattatatactcgagatatatttcgac
catagccaattcaatatggcgtatatggactcatgccaattcaatatggtggatctggacctgtgccaattcaat
atggcgtatatgactcgtgccaattcaatatggtggatccgacccagccaattcaatatggcggactttgg
caccatgccaattcaatatggcggacttggcactgtgccaactggggaggggtctacttggcacggtgcca
agtttgaggaggggtcttggccctgtgccaagtccgccatattgaattggcatggtgccaataatggcggcc
atattggctatatgccaggatcaatatataggcaatatccaatatggcccctatgccaatatggctattggccag
gttcaatactatgtattggccctatgcatatagtattccatatagtgggttttcctattgacgtagatagccctcc
caatgggcggtcccatataccatatatggggcttcctaataccgcccatagccactccccattgacgtcaat
ggtctctatatatggtctttcctattgacgtcatatgggcggtcctattgacgtatatggcgcctcccccattgac
gtcaattacggtaaatgcccgcctggctcaatgcccattgacgtcaataggaccacccaccattgacgtca
atgggatggtcattgcccattcatatccgttctcacgccccctattgacgtcaatgacggtaaatggcccactt
ggcagtacatcaatatctattaatagtaacttggcaagtacattactattggaaggacgccagggtacattggc
agtactcccattgacgtcaatggcggtaaatgcccgcgatggctgccaagtacatccccattgacgtcaat
ggggagggcaatgacgcaaatgggcgttccattgacgtaaatgggcggtaggcgtgcctaatgggaggt
ctatataagcaatgctcgtttagggaac
```

| BAT1206F<br>light chain | QIVLSQSPAILSASPGEKVTMTCRASSSVSYIHWFQQKPGSS<br>PKPWIYATSNLASGVPVRFSGSGSGTSYSLTISRVEAEDAAT<br>YYCQQWTSNPPTFGGGTKLEIKRTVAAPSVFIFPPSDEQLKS<br>GTASVVCLLNNFYPREAKVQWKVDNALQSGNSQESVTEQ<br>DSKDSTYSLSSTLTLSKADYEKHKVYACEVTHQGLSSPVTK<br>SFNRGEC | SEQ ID<br>NO. 18 |
| --- | --- | --- |
| BAT1206F<br>heavy chain | QVQLQQPGAELVKPGASVKMSCKASGYTFTSYNMHWVK<br>QTPGRGLEWIGAIYPGNGDTSYNQKFKGKATLTADKSSST<br>AYMQLSSLTSEDSAVYYCARSTYYGGDWYFNVWGAGTT<br>VTVSAASTKGPSVFPLAPSSKSTSGGTAALGCLVKDYFPEP<br>VTVSWNSGALTSGVHTFPAVLQSSGLYSLSSVVTVPSSSLG<br>TQTYICNVNHKPSNTKVDKKAEPKSCDKTHTCPPCPAPELL<br>GGPSVFLFPPKPKDTLMISRTPEVTCVVVDVSHEDPEVKFN<br>WYVDGVEVHNAKTKPREEQYNSTYRVVSVLTVLHQDWL<br>NGKEYKCKVSNKALPAPIEKTISKAKGQPREPQVYTLPPSR<br>DELTKNQVSLTCLVKGFYPSDIAVEWESNGQPENNYKTTPP<br>VLDSDGSFFLYSKLTVDKSRWQQGNVFSCSVMHEALHNH<br>YTQKSLSLSPGK | SEQ ID<br>NO. 19 |
| BAT4306F<br>light chain | DIVMTQTPLSLPVTPGEPASISCRSSKSLLHSNGITYLYWYLQKPGQS<br>PQLLIYQMSNLVSGVPDRFSGSGSGTDFTLKISRVEAEDVGVYYCAQ<br>NLELPYTFGGGTKVEIKR | SEQ ID<br>NO. 20 |
| BAT4306F<br>heavy chain | QVQLVQSGAEVKKPGSSVKVSCKASGYAFSYSWINWVRQAPGQGL<br>EWMGRIFPGDGDTDYNGKFKGRVTITADKSTSTAYMELSSLRSEDTA<br>VYYCARNVFDGYWLVYWGQGTLVTVSSASTKGPSVFPLAPSSKSTS<br>GGTAALGCLVKDYFPEPVTVSWNSGALTSGVHTFPAVLQSSGLYSLS<br>SVVTVPSSSLGTQTYICNVNHKPSNTKVDKKVEPKSCDKTHTCPPCP<br>APELLGGPSVFLFPPKPKDTLMISRTPEVTCVVVDVSHEDPEVKFNW<br>YVDGVEVHNAKTKPREEQYNSTYRVVSVLTVLHQDWLNGKEYKC<br>KVSNKALPAPIEKTISKAKGQPREPQVYTLPPSRDELTKNQVSLTCLV<br>KGFYPSDIAVEWESNGQPENNYKTTPPVLDSDGSPPLYSKLTVDKSR<br>WQQGNVFSCSVMHEALHNHYTQKSLSLSPGK | SEQ ID<br>NO. 21 |
| BAT4406F<br>light chain | EIVLTQSPATLSLSPGERATLSCRASQSVSSYLAWYQQKPGQAPRLLI<br>YDASNRATGIPARFSGSGSGTDFTLTISSLEPEDFAVYYCQQRSNWPIT<br>FGQGTRLEIKRTVAAPSVFIFPPSDEQLKSGTASVVCLLNNFYPREAK<br>VQWKVDNALQSGNSQESVTEQDSKDSTYSLSSTLTLSKADYEKHKV<br>YACEVTHQGLSSPVTKSFNRGEC | SEQ ID<br>NO. 22 |
| BAT4406F<br>heavy chain | EVQLVESGGGLVQPGRSLRLSCAASGFTFNDYAMHWVRQAPGKGL<br>EWVSTISWNSGSIGYADSVKGRFTISRDNAKKSLYLQMNSLRAEDTA<br>LYYCAKDIQYGNYYYGMDVWGQGTTVTVSSASTKGPSVFPLAPGS<br>SKSTSGTAALGCLVKDYFPEPVTVSWNSGALTSGVHTFPAVLQSSGL<br>YSLSSVVTVPSSSLGTQTYICNVNHKPSNTKVDKKVEPKSCDKTHTC<br>PPCPAPELLGGPSVFLFPPKPKDTLMISRTPEVTCVVVDVSHEDPEVK<br>FNWYVDGVEVHNAKTKPREEQYNSTYRVVSVLTVLHQDWLNGKE<br>YKCKVSNKALPAPIEKTISKAKGQPREPQVYTLPPSRDELTKNQVSLT<br>CLVKGFYPSDIAVEWESNGQPENNYKTTPPVLDSDGSFFLYSKLTVD<br>KSRWQQGNVFSCSVMHEALHNHYTQKSLSLSPGK | SEQ ID<br>NO. 23 |
| BAT0206F<br>light chain | DIQMTQSPSSLSASVGDRVTITCQASQDISNYLNWYQQKPGKAPKLL<br>IYDASNLETGVPSRFSGSGSGTDFTFTISSLQPEDIATYFCQHFDHLPL<br>AFGGGTKVEIKRTVAAPSVFIFPPSDEQLKSGTASVVCLLNNFYPREA<br>KVQWKVDNALQSGNSQESVTEQDSKDSTYSLSSTLTLSKADYEKHK<br>VYACEVTHQGLSSPVTKSFNRGEC | SEQ ID<br>NO. 24 |

TABLE 1-continued

Sequence table

| Name | Sequence | SEQ ID |
|---|---|---|
| BAT0206F heavy chain | QVQLQESGPGLVKPSETLSLTCTVSGGSVSSGDYYWTWIRQSPGKGL EWIGHIYYSGNTNYNPSLKSRLTISIDTSKTQFSLKLSSVTAADTAIYY CVRDRVTGAFDIWGQGTTVTVSSACTKGPSVFPLAPSSKSTSGGTAA LGCLVKDYFPEPVTVSWNSGALTSGVHTFPAVLQSSGLYSLSSVVTV PSSSLGTQTYICNVNHKPSNTKVDKKVEPKSCDKTHTCPPCPAPELL GGPSVFLFPPKPKDTLMISRTPEVTCVVVDVSHEDPEVKFNWYVDG VEVHNAKTKPREEQYNSTYRVVSVLTVLHQDWLNGKEYKCKVSNK ALPAPIEKTISKAKGQPREPQVYTLPPSRDELTKNQVSLTCLVKGFYP SDIAVEWESNGQPENNYKTTPPVLDSDGSFFLYSKLTVDKSRWQQG NVFSCSVMHEALHNHYTQKSLSLSPGK | SEQ ID NO. 25 |
| BAT0808 light chain | DIQLTQSPSSLSASVGDRVSITCKASQDVSIAVAWYQQKPGKAPKLLI YSASYRYTGVPDRFSGSGSGTDFTLTISSLQPEDFAVYYCQQHYITPL TFGAGTKVEIKRTVAAPSVFIFPPSDEQLKSGTASVVCLLNNFYPREA KVQWKVDNALQSGNSQESVTEQDSKDSTYSLSSTLTLSKADYEKHK VYACEVTHQGLSSPVTKSFNRGEC | SEQ ID NO. 26 |
| BAT0808 Heavy chain | QVQLQQSGSELKKPGASVKVSCKASGYTFTNYGMNWVKQAPGQG LKWMGWINTYTGEPTYTDDFKGRFAFSLDTSVSTAYLQISSLKADDT AVYFCARGGFGSSYWYFDVWGQGTLVTVSSCSTKGPSVFPLAPSSK STSGGTAALGCLVKDYFPEPVTVSWNSGALTSGVHTFPAVLQSSGLY SLSSVVTVPSSSLGTQTYICNVNHKPSNTKVDKKVEPKSCDKTHTCP PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVEWESNGQPENNYKTTPPVLDSDGSFFLYSKLTVDK SRWQQGNVFSCSVMHEALHNHYTQKSLSLSPGK | SEQ ID NO. 27 |
| CHO-BAT-KF Exon1 | ATGCGGGCATGGACTGGTTCCTGGCGTTGGATTATGCTCATTCTTT TTGCCTGGGGGACCTTATTGTTTTATATAGGTGGTCATTTGGTTCGA GATAATGACCACCCTGACCATTCTAGCAGAGAACTCTCCAAGATT CTTGCAAAGCTGGAGCGCTTAAACAACAAAATGAAGACTTGAGG AGAATGGCTGAGTCTCTCCGG | SEQ ID NO. 28 |

Example 3 Functional Effectiveness Analysis of FUT8 TALEN Protein

Figure 3:
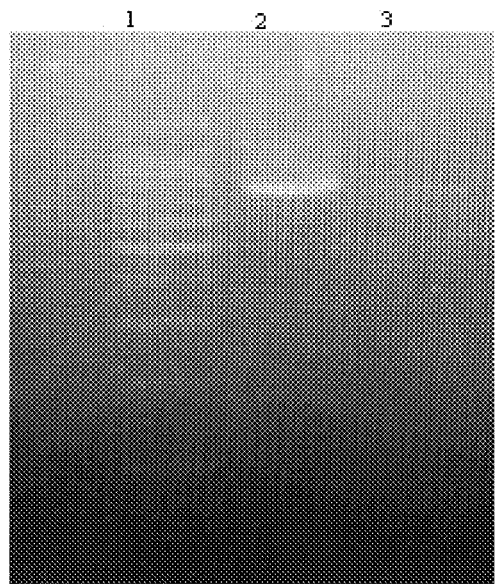
FIG. 3 shows an electrophoretogram for functional verification of TALEN protein. The electrophoresis chart of wild-type cells is located in the left side. After gene editing, expectedly, the PCR products of cell genome showed two bands of 500 BP and 750 BP, while that of the wild type only showed a single band of 750 BP. This proves that the Talen protein pair is functional. Lane 1: 100 bp marker; Lane 2: wt; Lane 3: pool.

CEL-I enzyme is a nuclease that can recognize the mismatched bases in double-stranded DNA and cut the double-stranded DNA from the mismatches. If the target sequence is edited by FUT8TALEN, the fragment containing the target sequence amplified from the maternal genome and the fragment containing the target sequence amplified from the transformed cell genome are mixed together for denaturation and annealing, the annealed double-stranded DNA will appear base mismatch. In this case, CEL-I enzyme can cut off the annealed double-stranded DNA, and two bands appear as a result of agarose electrophoresis. 5×10$^5$ CHO-BAT cells were seeded into a 6-well plate on the day before transfection, and the medium was DMEM/F12 containing 10% fetal calf serum. Plasmids L130N and R184N were transiently transfected into cells according to the methods provided in the reagent instructions. 3 days after transfection, the cells were harvested by centrifugation and the genome was extracted with the genome extraction kit. Using this as a template, PCR reaction was carried out with the primers L130for (SEQ ID NO. 1) and primer L130rev (SEQ ID NO. 2). The PCR amplification of the fragment of the parent cell containing the target sequence was the same as above. 20 μL of two PCR products were mixed together, heated to 94° C. and then naturally cooled to room temperature. Added 0.5 μl of CEL-I enzyme to 200 ng annealed DNA, and incubated at 42° C. for 30 min, and ran the PCR reaction product on agarose gel electrophoresis. The reaction product was analyzed by agarose electrophoresis, and the results are as shown in FIG. 3.

The results show that, compared with the wild type, the gene-edited PCR products displayed two bands of 500 bp and 750 bp, while the wild type only had a single band of 750 bp, which is consistent with the expected results. This proves that TALEN protein pairs are functional.

Example 4 Effect of FUT8 TALEN Protein on Antibody Fucose Content

Figure 4:
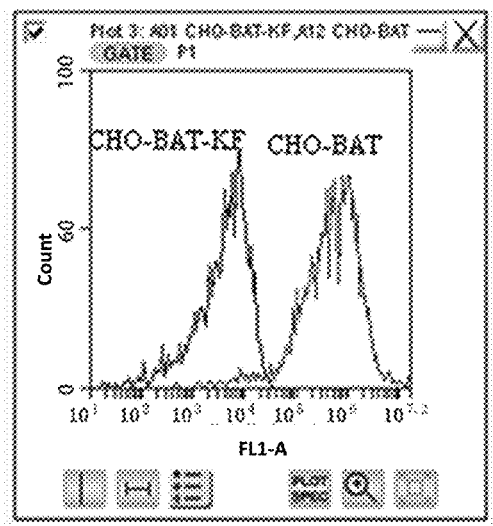
FIG. 4 shows the cells growing on 24-well plates analyzed by FACS, wherein the gene-edited cell clones labeled with FITC-labeled LCA bind the negative cells, and the wild-type cells labeled with FITC-labeled LCA bind the cells positively.

To determine whether the host genome adjusted by the designed FUT8 TALEN protein affects the carbohydrate chain of the produced antibody (whether the fucose content changes or not), L130N and R184N plasmids are transiently transformed into previously established cell lines stably expressing anti-CD20 antibodies. The methods provided in lipofectamine 2000 (Invitrogen) reagent description was taken and briefly described as follows. In a 10 cm cell culture dish, 24 μL of liposomes packed with 4 μg of plasmid DNA of L130N and R184N were added to 1×10$^6$ cells. After transfection for two days, the medium was replaced into DMEM/F12 medium containing 10% (V/V) FBS (GBICO) and 400 μg/mL LCA (Vector). After one week, most of the cells became round and suspended in the medium, while others grew normally on the wall. The supernatant was discarded, and LCA-resistant cells were digested with trypsin 0.25% (v/v), and resuspended in DMEM/F12 medium containing 10% (v/v) FBS after centrifugation. The cells were seeded in the 96-well plate at a density of 0.5 per well. After two weeks, monoclonal cells were selected and transferred to a 24-well plate. FACS was adopted to analyze the cells grown on a 24-well plate, and FITC labeled LCA bound to negative cells (FIG. 4) were propagated to produce antibodies. The oligosaccharide content of antibodies produced by the two cells was determined by Biodonor, and the results are shown in FIG. 5.

The results show that the fucose content of antibody was reduced when plasmids L130 and R184 were transiently transformed into antibody-producing cells.

Example 5 Establishment of Genome-Modified Host Cells

In order to establish a genome-modified CHO-K1 cell so that it can be the host cells used as proteins and fucose-free antibodies, the plasmids L130 and R184 were transiently transformed into CHO-K1 cell lines. The screening of monoclonal cells against LCA was described in example 3. The genome of candidate cell clones was extracted respectively, PCR reaction was carried out with the primer L130for (see Table 1, SEQ ID NO. 1) and the primer L130rev (see Table 1, SEQ ID NO. 2), and CEL-1 base mismatch analysis was carried out on PCR amplification products of fragments containing target sequences of candidate cell clones. If the candidate clone was heterozygous, then the agarose electrophoresis after CEL-1 enzyme digestion showed two bands; instead, if the candidate clone was homozygous, then the annealed fragment could not be cleaved through CEL-1 enzyme digestion, and the agarose electrophoresis showed one band. The PCR fragment was cloned directly into a T vector (pGEM-T Easy Vector) and then sequenced. The sequencing result was compared with the sequence of the parent cell in this fragment as shown in FIG. 6. Then, according to the comparison result, two genome-edited homozygotes were selected and designated as CHO-2G8, CHO-1D6.

Example 6 Evaluation of Growth Characteristics of Host Cells

Figure 7:
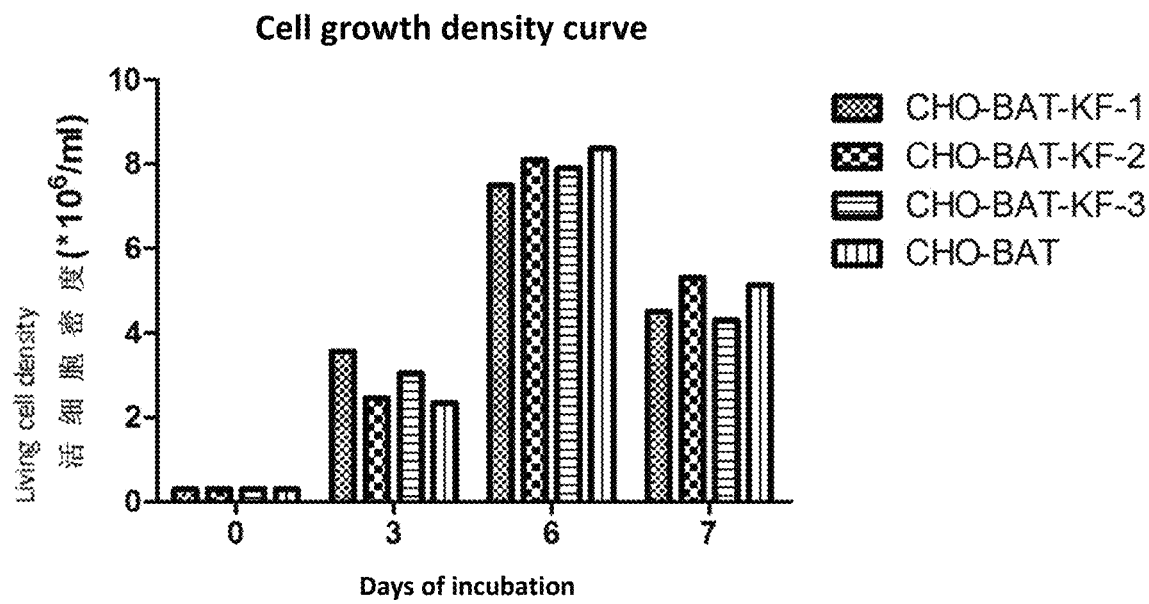
FIG. 7 shows the comparison of the growth density of CHO-BAT-KF to the parent cell CHO-BAT.
Figure 8:
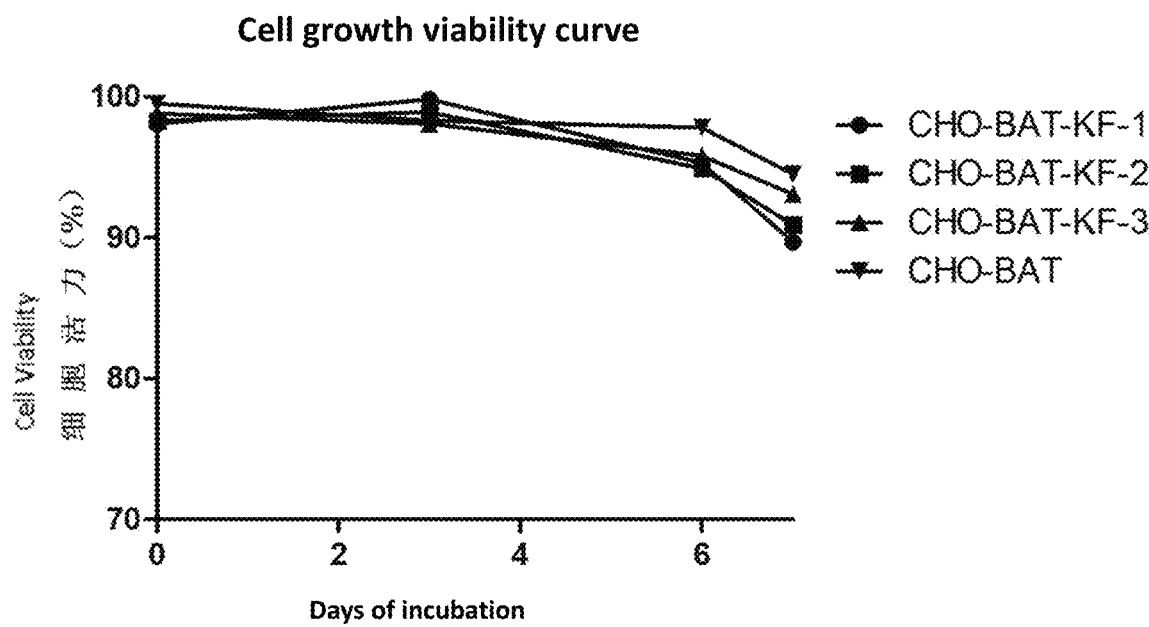
FIG. 8 shows the comparison of the growth viability of CHO-BAT-KF to the parent cell CHO-BAT.

The FUT8 gene knockout cloned CHO-2G8 was selected as the host cell and renamed as CHO-BAT-KF. Three CHO-BAT-KFs and one CHO-BAT were respectively seeded in 30 mL CD CHO AGT™ with a final concentration of 6 mM Gln in a 125 mL shake flask at the cell density of 300000/ml, and 0.5 mL of cells were taken at d0, d3, d6 and d7, respectively, to measure the cell density and cell viability and evaluate the change of cell growth characteristics after the FUT8 gene was knocked out. The cell growth density is shown in FIG. 7 and the cell growth viability is shown in FIG. 8. As can be seen from FIG. 7 and FIG. 8, no significant difference was observed in growth density and viability between FUT8 gene knock-out CHO-BAT-KF and CHO-BAT cells with FUT8 gene not knocked out.

Figure 9:
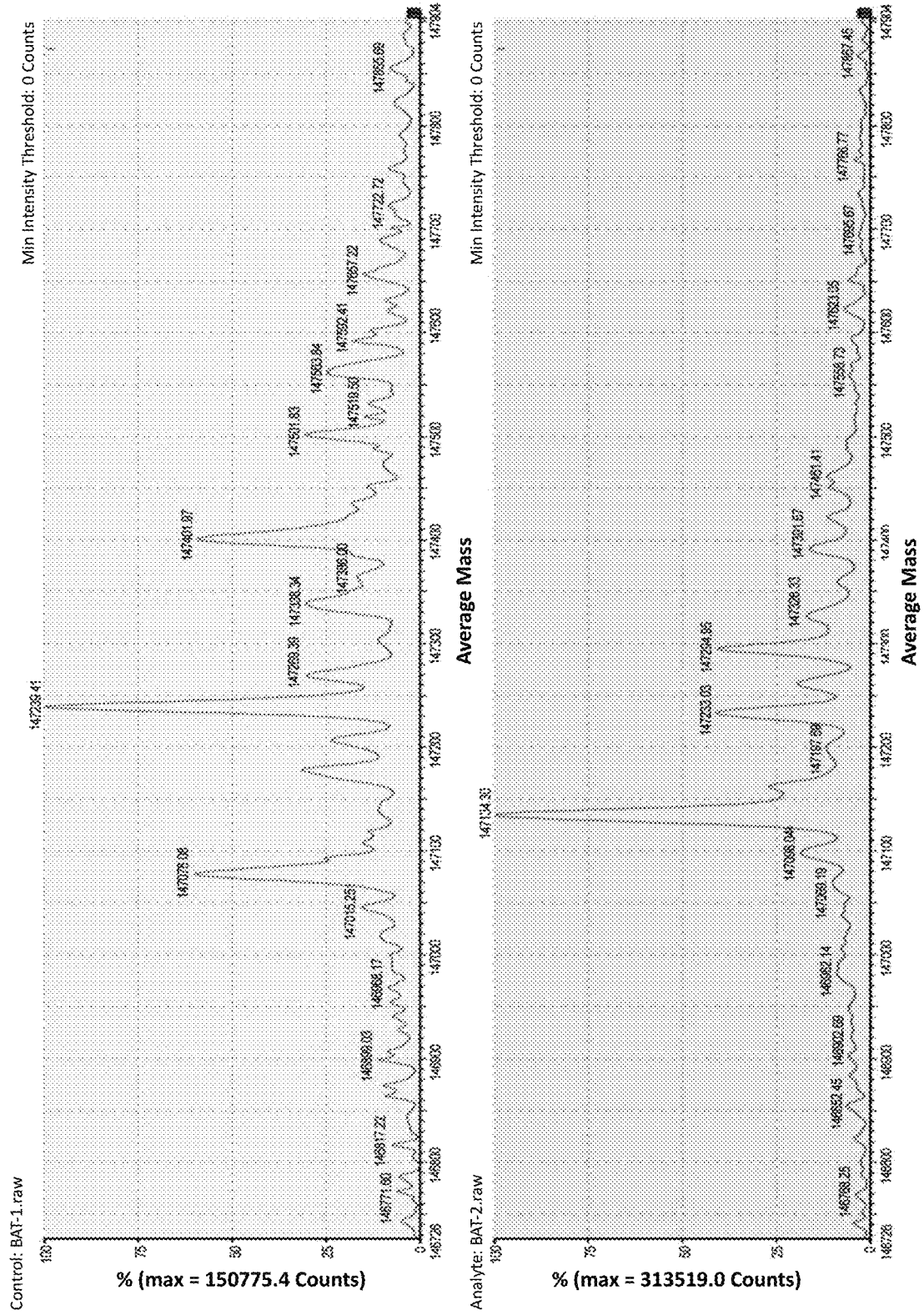
FIG. 9 shows analysis of N-polysaccharides from BAT4306F and 4306 antibody molecules performed by MALDI-TOF MS. Each N-polysaccharide from BAT4306F was one fucose less than that from 4306. The chart on the left is the antibody molecules 4306 produced by parent cells and the chart on the right is BAT4306F antibody molecules.

Example 7 Analysis of Glycosylation Profile of Antibodies Produced by Host Cells In order to determine that the carbohydrate chain of the antibody produced by the genome-modified CHO-2G8 cell line according to the present invention has aberrant N-polysaccharide modification, BAT4306F produced by CHO-2G8 cells and 4306 produced by CHO-K1 cells were purified from the medium through a protein A affinity column and quantified by UV280. Desalinated monoclonal antibody (1 mg) was incubated with PNGaseF overnight at 37° C. to release N-glycan from the antibody. The released N-glycan was separated from the antibody by 30K Amicon ultrafiltration, lyophilized and resuspended in 200 μL deionized water. MALDI-TOF MS was used to analyze N-polysaccharides from two antibody molecules as described above. Oligosaccharides from the antibody BAT4306F produced by CHO-2G8 existed in a single peak and were basically the same population, which was different from the profile of the antibody 4306 oligosaccharides produced by parent host cells (FIG. 9).

The results show that the three peaks of N-polysaccharide of 4306 were G0F, G1F and G2F, respectively. Based on the peak time and molecular weight of N-polysaccharide from BAT4306F, it was inferred that the three peaks of N-polysaccharide are G0, G1 and G2; that was, each N-polysaccharide from BAT4306F was one fucose less than the N-polysaccharide from 4306.

Figure 10:
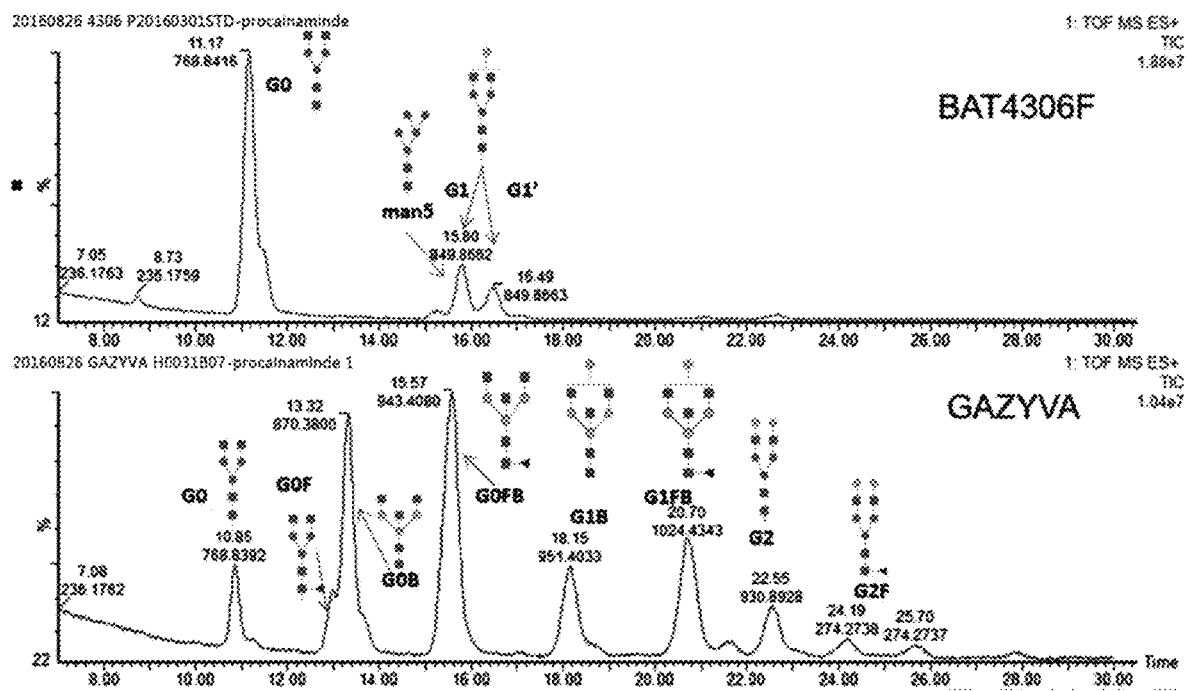
FIG. 10 shows that BAT4306F has lower fucose content, lower carbohydrate chain heterogeneity and better product uniformity than GAZYVA (Obinutuzumab).

At the same time, commercially available Gazyva was compared with the carbohydrate chains of BAT4306F to analyze the heterogeneity of their carbohydrate chains, as shown in FIG. 10. The results show that BAT4306F had lower N-polysaccharide heterogeneity and a more uniform carbohydrate chain. The glycotypes of different antibodies expressed in CHO-BAT-KF cells were analyzed as shown in Table 4.

Example 8 Analysis of ADCC Activity of Antibodies Produced by Host Cells

In order to determine whether the modification of the antibody having the N-polysaccharide of the present invention can improve its biological function (e.g., ADCC activity), the purified antibodies targeting CD20 are used to determine their ADCC activity in vitro (LDH method promega). The BAT4306F antibody produced by CHO-2G8 was purified through protein A affinity column and was quantified by UV280. The parent unmodified 4306 was expressed in wild-type CHO cells and purified in the same way. To carry out ADCC detection, the wil2-S cells were cultured in RPMI-1640 medium containing 10% FBS in good condition (4-7 days). Centrifuged cells in logarithmic growth phase at 1000 rpm for 10 min to remove supernatant. Added solution A (RPMI-1640 culture medium without phenol red and containing 10% FBS) and mixed well, centrifuged twice as above, counted, adjusted the number of cells to $3\times10^5$ cells/ml with solution A, and added it to U-96 cell culture plate at 100 μl per well. Adjusted the final concentration of antibody to 1.2, 0.24, 0.048, 0.0096, 0.00192, 0.000384, 0.0000768 and 0.00001536 (μg/mL) sequentially. Incubated at 37° C. for 30 min in a 5% $CO_2$ incubator. Collected the effector cells PBMC, added solution B (RPMI-1640 culture medium without serum and phenol red) and centrifuged twice as above, counted, adjusted the number of cells to $3\times10^5$ cells/ml with solution B, and added it to the U-96 cell culture plate at 50 μl per well. Incubated at 37° C. for 3 h in a 5% $CO_2$ incubator. When there was still 45 min from the incubation time of 3 h, added 20 μl of lysate to the well of maximum release target cell, and then incubated in a 5% $CO_2$ incubator at 37° C. for 45 min. Placed the U-96 well cell culture plate in a centrifuge and centrifuged at 250 g for 4 min. Taken 50 μl/well supernatant to another 96-well plate with flat bottom, added 50 μl/well of prepared chromogenic fluid, gently shaken and mixed, and reacted for 30 min at room temperature without light. Added 50 μl/well of the stop solution and gently shaken and mixed. Read the results at the microplate reader OD490.

Figure 11:
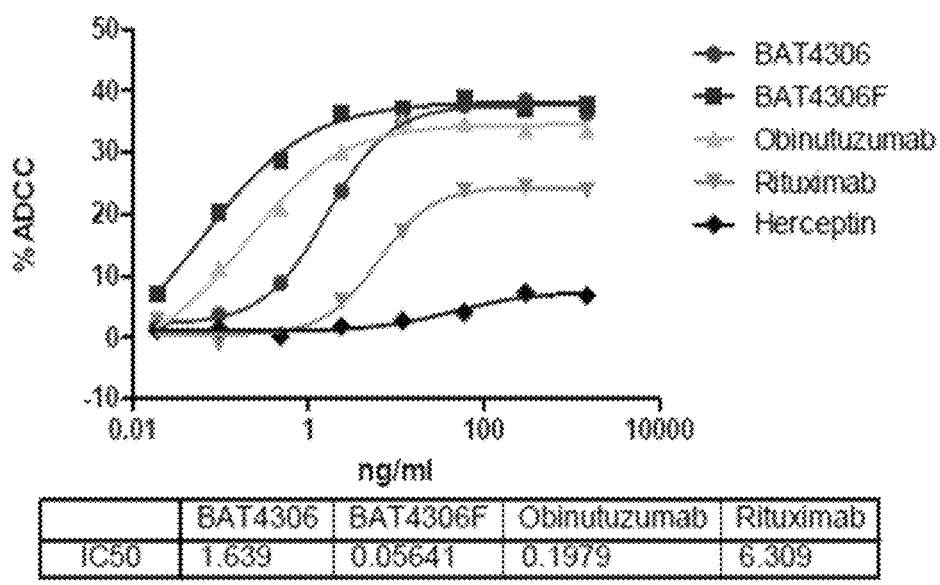
FIG. 11 shows the comparison of ADCC effects among anti-CD20 antibodies such as BAT4306 wild type, carbohydrate chain modified BAT4306F, Obinutuzumab and Rituximab using Raji as target cells and PBMC as effector cells.

The results show that, compared with non-modified 4306 produced by the parent CHO cells, BAT4306F of N-polysaccharide produced by CHO-2G8 cell cloning in serum-free medium significantly increased ADCC activity on Raji cells and wil2-S cells (FIG. 11).

Example 9 Analysis of Affinity of Antibodies Produced by Host Cells to CD20

In order to determine whether the antibody with modified N-polysaccharide produced by the cell according to the present invention has an effect on the ability to bind CD20-positive cells, BAT4306F and 4306 were verified by the FASC method by reference to Klervi Even-Desrumeaux et al. (2012), and the affinity of Rituximab to CD20 on different cell surfaces was compared, as described briefly below; collected Wil2-s cells in the logarithmic growth phase, centrifuged at 800 rpm for 5 min, and discarded supernatant. Washed once with PBS, calculated density, resuspended in PBS, and packed into 1.5 mL centrifuged tubes to make 500,000 cells per tube. Centrifuged at 1200 rpm for 5 min and discard supernatant. Prepared the antibody at concentrations of 30, 3.33, 1.11, 0.37, 0.1, 0.04, 0.014 and 0.0046 µg/mL, respectively, added 200 µl of antibody to the cells sequentially, resuspended the cells and mixed evenly. At the same time, added PBS of the same volume as the negative control. Kept away from light at 4° C. for 2 h. Centrifuged at 1200 rpm for 5 min, discarded supernatant and washed once with PBS. Added 100 µl of PBS to resuspend cells, added 2 µl of secondary antibody of FITC-sheep anti-human IgG1 Fab, and kept in dark place at 4° C. for 30 min. Centrifuged at 1200 rpm for 5 min, discarded supernatant and washed once with PBS. Detected with the C6 flow cytometer. Based on the formula $Kd=[Ab]*\{Fmax/(F-Fback)-1\}$, the results are shown in the following table.

TABLE 2

Statistical results of $IC_{50}$ and Kd values of antibody-to-cell binding experiments

| | BAT4306F | | 4306 | | Rituximab | |
|---|---|---|---|---|---|---|
| | Raji | Wil2-s | Raji | Wil2-s | Raji | Wil2-s |
| $IC_{50}$(µg/mL) | 0.481 | 0.815 | 0.631 | 0.603 | 1.998 | 2.513 |
| $IC_{50}$(nM) | 3.21 | 5.43 | 4.21 | 4.02 | 13.32 | 16.75 |
| Kd(nM) | 3.17 | 5.22 | 4.15 | 3.96 | 12.68 | 16.02 |
| Mean Kd(nM) | 4.19 | | 4.06 | | 14.35 | |

The results show that the modified antibody of N-polysaccharide did not affect the affinity of the antibody to CD20.

Figure 12:
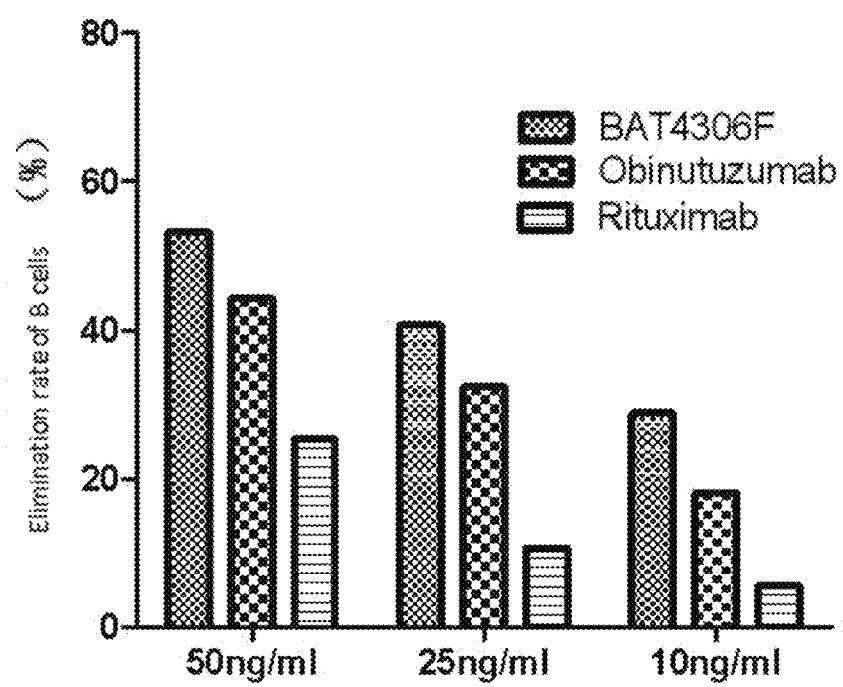
FIG. 12 shows the comparison of the ability among three carbohydrate chain modified antibodies BAT4306F, Obinutuzumab and rituximab to deplete B cells in whole blood in vitro at concentrations of 50, 25, and 10 ng/mL.

Example 10 the Ability of BAT4306F to Deplete B Cells in Whole Blood of Different NHL Patients Based on In Vitro Evaluation Although the mechanisms of anti-CD20 antibody in B lymphoma patients include ADCC, CDC and directly induced B cell apoptosis, the effect of an anti-CD20 antibody is ultimately reflected in its ability to remove B cells in patients, instead of merely improving a certain mechanism of action. In order to determine whether the antibody with N-polysaccharide modification of the present invention can improve its ability to remove B cells, the biological function of BAT4306F to deplete B cells in whole blood of different NHL patients was evaluated in vitro, as briefly described below: collected 3 ml of blood from newly diagnosed NHL patients in a heparin sodium anticoagulant tube; stored at room temperature and waited for the researcher to take away; taken 90 µL of blood samples into new FACS tubes; added 10 µL of BAT4306F antibody dilutions with different concentrations to each sample tube so that the final concentration of the antibody in each test sample tube was 10 nM, 1 nM, 0.1 nM, 0.01 nM and 0.001 nM respectively; stood in a 37° C. incubator for 3-4 h, then taken 50 µL of blood samples from each tube and added them to BD TruCount tubes, and added BD's B cell count antibody mixture (anti-CD45 (lymphocyte population), anti-CD3 (T cells) and anti-CD19 (B cells)) to the blood sample; placed in a dark place at room temperature for 15 min, added BD FACS lysate and then measured it on the instrument (BD C6). The results are shown in FIG. 12.

The results show that BAT4306F had stronger ability to remove B cells than antibody Rituximab without N-polysaccharide modified in the three concentration levels tested.

Example 11 Enhanced Affinity of BAT4306F to FcγRIIIa Molecule

In order to verify that the recombinant antibody with unique glycan profile produced by the genome-edited CHO-BAT-KF cells has enhanced affinity with FcγRIIIA, the affinity of BAT4306F, commercially available GAZYVA and Rituximab to FcγRIIIA was measured. The sensor was pre-wetted in PBS for 10 min. The biotin-labeled FcγRIIIa 158V and FcγRIIIa 158F were diluted to 2.5 µg/mL with AB solution. Loading: loaded in the biotin-labeled FcγRIIIa 158V diluent for 10 min (load to signal about 1.3 nM); 3.6.3 affinity test with FcγRIIIa 158V: diluted the test drugs BAT4306F and Obinutuzumab to 500 nM with AB solution, diluted the test drug Rituximab to 3000 nM with AB solution, and then prepared 7 concentrations with the same buffer solution at 2× gradient. AB solution, FcγRIIa V158, regeneration buffer, drug diluent and neutralization buffer were sequentially added to the corresponding columns of a 96-well plate. The SA sensor operates as follows: Baseline: detected the baseline in AB, 150 s; Association: combined in the gradient concentration of drug diluent sample and blank (AB) for 90 s; Dissociation: dissociated in AB for 120 s; Regeneration: regenerated in NaOH (pH 10.5) for 5 s; Neutralization: neutralized in AB for 5 s. The regeneration and neutralization cycles were carried out for 3 times. The collected data were analyzed by the instrument data analysis software Acquisition 8.2. Taking Baseline acquisition signal as a baseline and subtracting the reference signal (double deduction of sample blank and sensor blank), the data were subject to group analysis and fitted.

TABLE 3

Statistics of affinity BAT4306F to FcγRIIIa 158F

| | FcγRIIIa 158 V | | FcγRIIIa 158 F | |
|---|---|---|---|---|
| | KD(M) | CV % | KD(M) | CV % |
| BAT4306F | 2.57E-08 | 0.027 | 1.37E-07 | 0.878 |
| Obinutuzumab | 3.68E-08 | 10.483 | 2.26E-07 | 3.062 |
| Rituxiamb | 8.44E-07 | 3.79 | 1.19E-06 | 0.297 |

The results show that, among the three tested antibodies, the recombinant antibody with unique glycan profile produced by CHO-BAT-KF cells had the strongest affinity to FcγRIIIA.

Example 12

Figure 13:
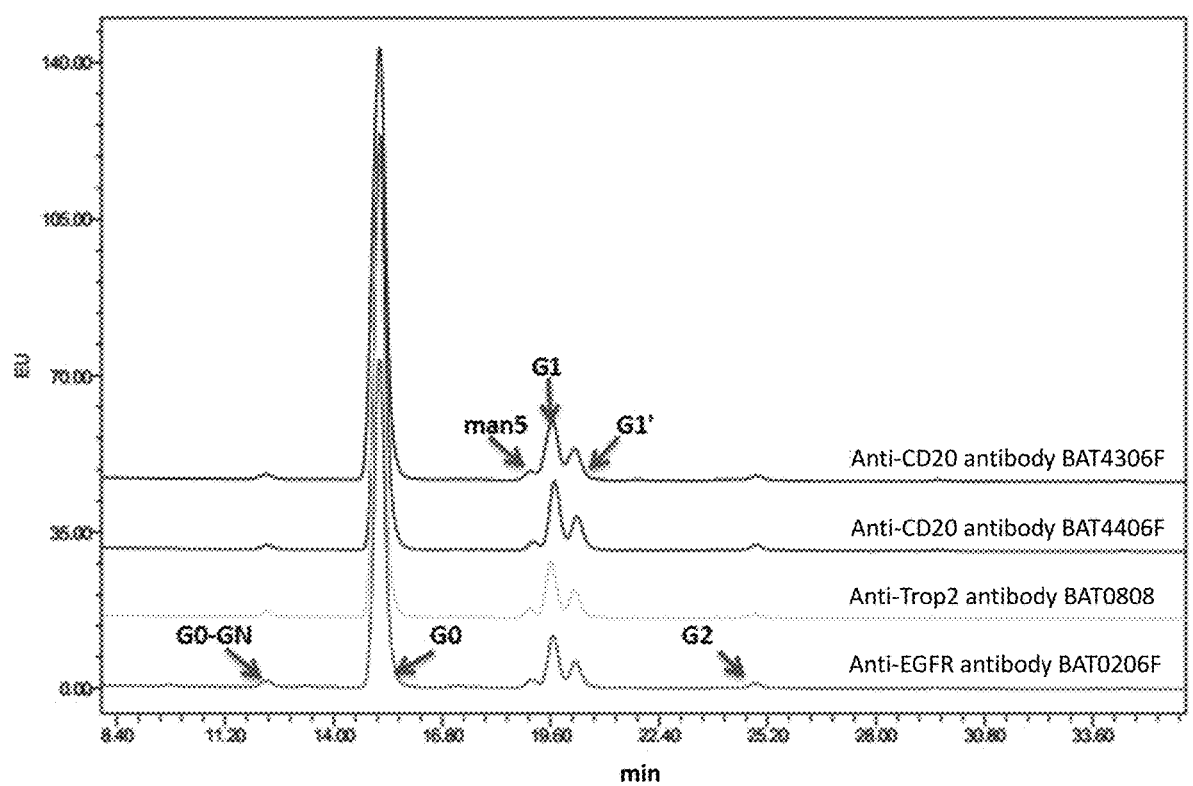
FIG. 13 shows the comparison of the glycan profile among the anti-CD20 antibodies BAT4306F and BAT4406F, the anti-EGFR antibody BAT0206F, and the anti-Trop2 antibody BAT0808 produced by CHO-BAT-KF cells.

In order to verify that the glycan profile of the antibody produced by the expression of other antibody sequences in the CHO-BAT-KF host cell is stable and consistent, several other antibodies were expressed in the CHO-BAT-KF cell, including BAT4406F antibody with two light chains as shown in SEQ ID NO. 22 and two heavy chains as shown in SEQ ID NO. 23, BAT0206F antibody with two light chains as shown in SEQ ID NO. 24 and two heavy chains as shown in SEQ ID NO. 25, and Trop2 antibody BAT0808 with two light chains as shown in SEQ ID NO. 26 and two heavy chains as shown SEQ ID NO. 27. The specific experiment was carried out by reference to the product specification (LudgerTag™ PROC (procainamide) Glycan Labeling Kit). The sample was denatured and reduced, and its carbohydrate chain was removed from the glycosylation site by glycosidase. Then, after coupling labeled with procainamide hydrochloride fluorescein, the sample was separated on a HILIC column, 100 mM ammonium formate (pH 4.5) and acetonitrile were eluted with a mobile phase A and a mobile phase B respectively with an elution gradient of 0-36 minutes from 28% A-38% A, and finally detected with a fluorescence detector. The resolution of glycotypes G1 and G1' in the system suitability solution was not less than 1.0. The results in FIG. 13 and Table 4 show that the glycotypes of the four antibodies were highly consistent and the carbohydrate chains was uniform; which indicated that the method or cell of the present invention had universal applicability, and could be not only suitable for the production of anti-CD20 antibodies, but also used for the production of antibodies at other sites, thus allowing the target antibody to present uniformity and enhanced ADCC activity.

TABLE 4

Glycotype ratio (%) of four antibodies produced by CHO-BAT-KF cells

|  | G0-GN | G0 | Man5 | G1 | G1' | G2 | Other |
|---|---|---|---|---|---|---|---|
| BAT4306F | 0.36 | 71.32 | 0.40 | 16.04 | 8.14 | 1.96 | 1.78 |
| BAT4406F | 0.42 | 72.31 | 0.45 | 15.51 | 7.88 | 1.83 | 1.60 |
| BAT0808 | 0.52 | 79.11 | 0.51 | 11.36 | 6.11 | 1.03 | 1.36 |
| BAT0206F | 0.45 | 76.15 | 0.50 | 12.90 | 6.90 | 1.36 | 1.74 |

The invention claimed is:

1. An antibody, characterized in that the antibody is BAT4306F antibody, wherein the BAT4306F antibody is an anti-CD20 antibody that comprises two light chains each comprising the amino acid sequence of SEQ ID NO: 20 and two heavy chains each comprising the amino acid sequence of SEQ ID NO: 21, and wherein the BAT4306F antibody has a G0 content that is greater than or equal to 60% and has no fucose.

2. A pharmaceutical composition, comprising the antibody according to claim 1 and a pharmaceutically acceptable carrier.

3. A method for treating Non-Hodgkin Lymphoma, (NHL), comprising administration of an effective amount of the antibody according to claim 1 to a subject in need thereof.

4. The antibody of claim 1, wherein the antibody has a mannose content that is less than or equal to 5%.

5. The antibody of claim 1, wherein the antibody has a high mannose content that is less than or equal to 5%.

* * * * *

SEQUENCE LISTING

```
<160> NUMBER OF SEQ ID NOS: 33

<210> SEQ ID NO 1
<211> LENGTH: 21
<212> TYPE: DNA
<213> ORGANISM: Artificial Sequence
<220> FEATURE:
<223> OTHER INFORMATION: Synthetic

<400> SEQUENCE: 1
gggtagctaa ttgtctttca g                                              21

<210> SEQ ID NO 2
<211> LENGTH: 20
<212> TYPE: DNA
<213> ORGANISM: Artificial Sequence
<220> FEATURE:
<223> OTHER INFORMATION: Synthetic

<400> SEQUENCE: 2
taaatgccac tgcttctata                                                20

<210> SEQ ID NO 3
<211> LENGTH: 20
<212> TYPE: DNA
<213> ORGANISM: Artificial Sequence
<220> FEATURE:
<223> OTHER INFORMATION: Synthetic

<400> SEQUENCE: 3
tccaagattc ttgcaaagct                                                20

<210> SEQ ID NO 4
<211> LENGTH: 18
<212> TYPE: DNA
<213> ORGANISM: Artificial Sequence
<220> FEATURE:
```

<223> OTHER INFORMATION: Synthetic

<400> SEQUENCE: 4
aatgaagact tgaggaga                                              18

<210> SEQ ID NO 5
<211> LENGTH: 19
<212> TYPE: DNA
<213> ORGANISM: Artificial Sequence
<220> FEATURE:
<223> OTHER INFORMATION: Synthetic

<400> SEQUENCE: 5
ggagcgctta aaacaacaa                                             19

<210> SEQ ID NO 6
<211> LENGTH: 763
<212> TYPE: DNA
<213> ORGANISM: Artificial Sequence
<220> FEATURE:
<223> OTHER INFORMATION: Synthetic

<400> SEQUENCE: 6
gggtagctaa ttgtctttca gcctcctggc caaagatacc atgaaagtca acttacgttg    60
tattctatat ctcaaacaac tcagggtgtt tcttactctt tccacagcat gtagagccca   120
ggaagcacag gacaagaaag ctgcctcctt gtatcaccag gaagatcttt ttgtaagagt   180
catcacagta taccagagag actaattttg tctgaagcat catgtgttga acaacagaa    240 acttattttc ctgtgtggct aactagaacc agagtacaat gtttccaatt ctttgagctc   300
cgagaagaca gaagggagtt gaaactctga aaatgcgggc atggactggt tcctggcgtt   360
ggattatgct cattctttt gcctggggga ccttattgtt ttatataggt ggtcatttgg    420
ttcgagataa tgaccaccct gaccattcta gcagagaact ctccaagatt cttgcaaagc   480
tggagcgctt aaaacaacaa aatgaagact tgaggagaat ggctgagtct ctccggtagg   540
tttgaaatac tcaaggattt gatgaaatac tgtgcttgac ctttaggtat agggtctcag   600
tctgctgttg aaaaatataa tttctacaaa ccgtctttgt aaaattttaa gtattgtagc   660
agacttttta aaagtcagtg atacatctat atagtcaata taggtttaca tagttgcaat   720
cttattttgc atatgaatca gtatatagaa gcagtggcat tta                    763

<210> SEQ ID NO 7
<211> LENGTH: 204
<212> TYPE: DNA
<213> ORGANISM: Artificial Sequence
<220> FEATURE:
<223> OTHER INFORMATION: Synthetic

<400> SEQUENCE: 7
atgcgggcat ggactggttc ctggcgttgg attatgctca ttcttttgc ctggggacc     60 ttattgtttt ataggtgg tcatttggtt cgagataatg accaccctga ccattctagc    120
agagaactct ccaagattct tgcaaagctg gagcgcttaa acaacaaaa tgaagacttg   180 aggagaatgg ctgagtctct ccgg                                        204

<210> SEQ ID NO 8
<211> LENGTH: 1728
<212> TYPE: DNA
<213> ORGANISM: Artificial Sequence
<220> FEATURE:
<223> OTHER INFORMATION: Synthetic

<400> SEQUENCE: 8

```
atgcgggcat ggactggttc ctggcgttgg attatgctca ttcttttgc ctgggggacc     60
ttattgtttt ataggtgg tcatttggtt cgagataatg accaccctga ccattctagc    120
agagaactct ccaagattct tgcaaagctg agcgcttaa acaacaaaa tgaagacttg    180
aggagaatgg ctgagtctct ccgaatacca gaaggccta ttgatcaggg gacagctaca    240
ggaagagtcc gtgttttaga gaacagctt gttaaggcca agaacagat tgaaaattac    300
aagaaacaag ctaggaatga tctgggaaag gatcatgaaa tcttaaggag gaggattgaa    360
aatggagcta agagctctg gttttttcta caaagtgaat tgaagaaatt aaagaaatta    420
gaaggaaacg aactccaaag acatgcagat gaaattcttt tggatttagg acatcatgaa    480
aggtctatca tgacagatct atactacctc agtcaaacag atggagcagg tgagtggcgg    540
gaaaaagaag ccaaagatct gacagagctg gtccagcgga gaataacata tctgcagaat    600
cccaaggact gcagcaaagc cagaaagctg gtatgtaata tcaacaaagg ctgtggctat    660
ggatgtcaac tccatcatgt ggtttactgc ttcatgattg cttatggcac ccagcgaaca    720
ctcatcttgg aatctcagaa ttggcgctat gctactggag gatgggagac tgtgtttaga    780
cctgtaagtg agacatgcac agacaggtct ggcctctcca ctggacactg gtcaggtgaa    840
gtgaaggaca aaaatgttca gtggtcgag ctccccattg tagacagcct ccatcctcgt    900
cctccttact taccccttggc tgtaccagaa gaccttgcag atcgactcct gagagtccat    960
ggtgatcctg cagtgtggtg ggtatcccag tttgtcaaat acttgatccg tccacaacct   1020
tggctggaaa gggaaataga agaaaccacc aagaagcttg gcttcaaaca tccagttatt   1080
ggagtccatg tcagacgcac tgacaaagtg ggaacagaag cagccttcca tcccattgag   1140
gaatacatgg tacacgttga agaacatttt cagcttctcg aacgcagaat gaaagtggat   1200
aaaaaaagag tgtatctggc cactgatgac ccttctttgt taaggaggc aaagacaaag   1260
tactccaatt atgaatttat tagtgataac tctatttctt ggtcagctgg actacacaac   1320
cgatacacag aaaattcact tcggggcgtg atcctggata tacactttct ctcccaggct   1380
gacttccttg tgtgtacttt ttcatcccag gtctgtaggg ttgcttatga aatcatgcaa   1440
acactgcatc ctgatgcctc tgcaaacttc cattctttag atgacatcta ctattttgga   1500
ggccaaaatg cccacaacca gattgcagtt tatcctcacc aacctcgaac taagagggaa   1560
atccccatgg aacctggaga tatcattggt gtggctggaa accattggaa tggttactct   1620
aaaggtgtca acagaaaact aggaaaaaca ggcctgtacc cttcctacaa agtccgagag   1680
aagatagaaa cagtcaaata ccctacatat cctgaagctg aaaaatag              1728
```

<210> SEQ ID NO 9
<211> LENGTH: 575
<212> TYPE: PRT
<213> ORGANISM: Artificial Sequence
<220> FEATURE:
<223> OTHER INFORMATION: Synthetic

<400> SEQUENCE: 9

```
Met Arg Ala Trp Thr Gly Ser Trp Arg Trp Ile Met Leu Ile Leu Phe
1               5                   10                  15

Ala Trp Gly Thr Leu Leu Phe Tyr Ile Gly Gly His Leu Val Arg Asp
            20                  25                  30

Asn Asp His Pro Asp His Ser Ser Arg Glu Leu Ser Lys Ile Leu Ala
        35                  40                  45
```

-continued

```
Lys Leu Glu Arg Leu Lys Gln Gln Asn Glu Asp Leu Arg Arg Met Ala
 50                  55                  60
Glu Ser Leu Arg Ile Pro Glu Gly Pro Ile Asp Gln Gly Thr Ala Thr
 65                  70                  75                  80
Gly Arg Val Arg Val Leu Glu Glu Gln Leu Val Lys Ala Lys Glu Gln
                     85                  90                  95
Ile Glu Asn Tyr Lys Lys Gln Ala Arg Asn Asp Leu Gly Lys Asp His
                100                 105                 110
Glu Ile Leu Arg Arg Ile Glu Asn Gly Ala Lys Glu Leu Trp Phe
                115                 120                 125
Phe Leu Gln Ser Glu Leu Lys Lys Leu Lys Lys Leu Glu Gly Asn Glu
130                 135                 140
Leu Gln Arg His Ala Asp Glu Ile Leu Asp Leu Gly His His Glu
145                 150                 155                 160
Arg Ser Ile Met Thr Asp Leu Tyr Tyr Leu Ser Gln Thr Asp Gly Ala
                165                 170                 175
Gly Glu Trp Arg Glu Lys Glu Ala Lys Asp Leu Thr Glu Leu Val Gln
                180                 185                 190
Arg Arg Ile Thr Tyr Leu Gln Asn Pro Lys Asp Cys Ser Lys Ala Arg
                195                 200                 205
Lys Leu Val Cys Asn Ile Asn Lys Gly Cys Gly Tyr Gly Cys Gln Leu
210                 215                 220
His His Val Val Tyr Cys Phe Met Ile Ala Tyr Gly Thr Gln Arg Thr
225                 230                 235                 240
Leu Ile Leu Glu Ser Gln Asn Trp Arg Tyr Ala Thr Gly Gly Trp Glu
                245                 250                 255
Thr Val Phe Arg Pro Val Ser Glu Thr Cys Thr Asp Arg Ser Gly Leu
                260                 265                 270
Ser Thr Gly His Trp Ser Gly Glu Val Lys Asp Lys Asn Val Gln Val
                275                 280                 285
Val Glu Leu Pro Ile Val Asp Ser Leu His Pro Arg Pro Pro Tyr Leu
290                 295                 300
Pro Leu Ala Val Pro Glu Asp Leu Ala Asp Arg Leu Leu Arg Val His
305                 310                 315                 320
Gly Asp Pro Ala Val Trp Trp Val Ser Gln Phe Val Lys Tyr Leu Ile
                325                 330                 335
Arg Pro Gln Pro Trp Leu Glu Arg Glu Ile Glu Thr Thr Lys Lys
                340                 345                 350
Leu Gly Phe Lys His Pro Val Ile Gly Val His Val Arg Arg Thr Asp
                355                 360                 365
Lys Val Gly Thr Glu Ala Ala Phe His Pro Ile Glu Glu Tyr Met Val
370                 375                 380
His Val Glu Glu His Phe Gln Leu Leu Glu Arg Arg Met Lys Val Asp
385                 390                 395                 400
Lys Lys Arg Val Tyr Leu Ala Thr Asp Asp Pro Ser Leu Leu Lys Glu
                405                 410                 415
Ala Lys Thr Lys Tyr Ser Asn Tyr Glu Phe Ile Ser Asp Asn Ser Ile
                420                 425                 430
Ser Trp Ser Ala Gly Leu His Asn Arg Tyr Thr Glu Asn Ser Leu Arg
                435                 440                 445
Gly Val Ile Leu Asp Ile His Phe Leu Ser Gln Ala Asp Phe Leu Val
450                 455                 460
```

```
Cys Thr Phe Ser Ser Gln Val Cys Arg Val Ala Tyr Glu Ile Met Gln
465                 470                 475                 480

Thr Leu His Pro Asp Ala Ser Ala Asn Phe His Ser Leu Asp Asp Ile
            485                 490                 495

Tyr Tyr Phe Gly Gly Gln Asn Ala His Asn Gln Ile Ala Val Tyr Pro
                500                 505                 510

His Gln Pro Arg Thr Lys Glu Glu Ile Pro Met Glu Pro Gly Asp Ile
        515                 520                 525

Ile Gly Val Ala Gly Asn His Trp Asn Gly Tyr Ser Lys Gly Val Asn
    530                 535                 540

Arg Lys Leu Gly Lys Thr Gly Leu Tyr Pro Ser Tyr Lys Val Arg Glu
545                 550                 555                 560

Lys Ile Glu Thr Val Lys Tyr Pro Thr Tyr Pro Glu Ala Glu Lys
                565                 570                 575

<210> SEQ ID NO 10
<211> LENGTH: 648
<212> TYPE: PRT
<213> ORGANISM: Artificial Sequence
<220> FEATURE:
<223> OTHER INFORMATION: Synthetic

<400> SEQUENCE: 10

Leu Thr Pro Glu Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Ala Gln Val Ala Ile Ala Ser His Asp Gly
        35                  40                  45

Gly Lys Gln Ala Leu Glu Thr Val Gln Arg Leu Leu Pro Val Leu Cys
    50                  55                  60

Gln Ala His Gly Leu Thr Pro Ala Gln Val Val Ala Ile Ala Ser Asn
65                  70                  75                  80

Ile Gly Gly Lys Gln Ala Leu Glu Thr Val Gln Arg Leu Leu Pro Val
                85                  90                  95

Leu Cys Gln Ala His Gly Leu Thr Pro Asp Gln Val Val Ala Ile Ala
            100                 105                 110

Ser Asn Ile Gly Gly Lys Gln Ala Leu Glu Thr Val Gln Arg Leu Leu
        115                 120                 125

Pro Val Leu Cys Gln Ala His Gly Leu Thr Pro Asp Gln Val Val Ala
    130                 135                 140

Ile Ala Ser Asn Asn Gly Gly Lys Gln Ala Leu Glu Thr Val Gln Arg
145                 150                 155                 160

Leu Leu Pro Val Leu Cys Gln Ala His Gly Leu Thr Pro Asp Gln Val
                165                 170                 175

Val Ala Ile Ala Ser Asn Ile Gly Gly Lys Gln Ala Leu Glu Thr Val
            180                 185                 190

Gln Arg Leu Leu Pro Val Leu Cys Gln Ala His Gly Leu Thr Pro Asp
        195                 200                 205

Gln Val Val Ala Ile Ala Ser Asn Gly Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Ala Gln Val Val Ala Ile Ala Ser Asn Gly Gly Gly Lys Gln Ala
                245                 250                 255
```

Leu Glu Thr Val Gln Arg Leu Leu Pro Val Leu Cys Gln Ala His Gly
                260                 265                 270

Leu Thr Pro Ala Gln Val Val Ala Ile Ala Ser His Asp Gly Gly Lys
            275                 280                 285

Gln Ala Leu Glu Thr Val Gln Arg Leu Leu Pro Val Leu Cys Gln Ala
        290                 295                 300

His Gly Leu Thr Pro Ala Gln Val Val Ala Ile Ala Ser Asn Gly Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Ala Gln Val Val Ala Ile Ala Ser Asn
            340                 345                 350

Gly Gly Gly Lys Gln Ala Leu Glu Thr Val Gln Arg Leu Leu Pro Val
        355                 360                 365

Leu Cys Gln Ala His Gly Leu Thr Pro Ala Gln Val Val Ala Ile Ala
370                 375                 380

Ser Asn Asn Gly Gly Lys Gln Ala Leu Glu Thr Val Gln Arg Leu Leu
385                 390                 395                 400

Pro Val Leu Cys Gln Ala His Gly Leu Thr Pro Asp Gln Val Val Ala
                405                 410                 415

Ile Ala Ser His Asp Gly Gly Lys Gln Ala Leu Glu Thr Val Gln Arg
            420                 425                 430

Leu Leu Pro Val Leu Cys Gln Ala His Gly Leu Thr Pro Ala Gln Val
        435                 440                 445

Val Ala Ile Ala Ser Asn Ile Gly Gly Lys Gln Ala Leu Glu Thr Val
450                 455                 460

Gln Arg Leu Leu Pro Val Leu Cys Gln Ala His Gly Leu Thr Pro Asp
465                 470                 475                 480

Gln Val Val Ala Ile Ala Ser Asn Ile Gly Gly Lys Gln Ala Leu Glu
                485                 490                 495

Thr Val Gln Arg Leu Leu Pro Val Leu Cys Gln Ala His Gly Leu Thr
            500                 505                 510

Pro Asp Gln Val Val Ala Ile Ala Ser Asn Ile Gly Gly Lys Gln Ala
        515                 520                 525

Leu Glu Thr Val Gln Arg Leu Leu Pro Val Leu Cys Gln Ala His Gly
    530                 535                 540

Leu Thr Pro Asp Gln Val Val Ala Ile Ala Ser Asn Asn Gly Gly Lys
545                 550                 555                 560

Gln Ala Leu Glu Thr Val Gln Arg Leu Leu Pro Val Leu Cys Gln Ala
                565                 570                 575

His Gly Leu Thr Pro Asp Gln Val Val Ala Ile Ala Ser His Asp Gly
            580                 585                 590

Gly Lys Gln Ala Leu Glu Thr Val Gln Arg Leu Leu Pro Val Leu Cys
        595                 600                 605

Gln Ala His Gly Leu Thr Pro Ala Gln Val Val Ala Ile Ala Ser Asn
    610                 615                 620

Gly Gly Gly Arg Pro Ala Leu Glu Ser Ile Val Ala Gln Leu Ser Arg
625                 630                 635                 640

Pro Asp Pro Ala Leu Ala Ala Leu
                645

<210> SEQ ID NO 11
<211> LENGTH: 580
<212> TYPE: PRT

<213> ORGANISM: Artificial Sequence
<220> FEATURE:
<223> OTHER INFORMATION: Synthetic

<400> SEQUENCE: 11

```
Leu Thr Pro Glu Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Ala Gln Val Val Ala Ile Ala Ser Asn Gly Gly
        35                  40                  45

Gly Lys Gln Ala Leu Glu Thr Val Gln Arg Leu Leu Pro Val Leu Cys
    50                  55                  60

Gln Ala His Gly Leu Thr Pro Ala Gln Val Val Ala Ile Ala Ser His
65                  70                  75                  80

Asp Gly Gly Lys Gln Ala Leu Glu Thr Val Gln Arg Leu Leu Pro Val
                85                  90                  95

Leu Cys Gln Ala His Gly Leu Thr Pro Ala Gln Val Val Ala Ile Ala
            100                 105                 110

Ser His Asp Gly Gly Lys Gln Ala Leu Glu Thr Val Gln Arg Leu Leu
        115                 120                 125

Pro Val Leu Cys Gln Ala His Gly Leu Thr Pro Ala Gln Val Val Ala
    130                 135                 140

Ile Ala Ser Asn Gly Gly Lys Gln Ala Leu Glu Thr Val Gln Arg
145                 150                 155                 160

Leu Leu Pro Val Leu Cys Gln Ala His Gly Leu Thr Pro Ala Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Ala
        195                 200                 205

Gln Val Val Ala Ile Ala Ser Asn Ile Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Asp Gln Val Val Ala Ile Ala Ser Asn Ile Gly Gly Lys Gln Ala
                245                 250                 255

Leu Glu Thr Val Gln Arg Leu Leu Pro Val Leu Cys Gln Ala His Gly
            260                 265                 270

Leu Thr Pro Asp Gln Val Val Ala Ile Ala Ser Asn Asn Gly Gly Lys
        275                 280                 285

Gln Ala Leu Glu Thr Val Gln Arg Leu Leu Pro Val Leu Cys Gln Ala
    290                 295                 300

His Gly Leu Thr Pro Asp Gln Val Val Ala Ile Ala Ser Asn Gly Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Ala Gln Val Val Ala Ile Ala Ser His
            340                 345                 350

Asp Gly Gly Lys Gln Ala Leu Glu Thr Val Gln Arg Leu Leu Pro Val
        355                 360                 365

Leu Cys Gln Ala His Gly Leu Thr Pro Ala Gln Val Val Ala Ile Ala
    370                 375                 380

Ser Asn Gly Gly Gly Lys Gln Ala Leu Glu Thr Val Gln Arg Leu Leu
```

```
                385                 390                 395                 400
Pro Val Leu Cys Gln Ala His Gly Leu Thr Pro Ala Gln Val Val Ala
                    405                 410                 415

Ile Ala Ser Asn Gly Gly Gly Lys Gln Ala Leu Glu Thr Val Gln Arg
                420                 425                 430

Leu Leu Pro Val Leu Cys Gln Ala His Gly Leu Thr Pro Ala Gln Val
            435                 440                 445

Val Ala Ile Ala Ser His Asp Gly Gly Lys Gln Ala Leu Glu Thr Val
        450                 455                 460

Gln Arg Leu Leu Pro Val Leu Cys Gln Ala His Gly Leu Thr Pro Ala
465                 470                 475                 480

Gln Val Val Ala Ile Ala Ser Asn Ile Gly Gly Lys Gln Ala Leu Glu
                    485                 490                 495

Thr Val Gln Arg Leu Leu Pro Val Leu Cys Gln Ala His Gly Leu Thr
                500                 505                 510

Pro Asp Gln Val Val Ala Ile Ala Ser Asn Gly Gly Gly Lys Gln Ala
            515                 520                 525

Leu Glu Thr Val Gln Arg Leu Leu Pro Val Leu Cys Gln Ala His Gly
        530                 535                 540

Leu Thr Pro Ala Gln Val Val Ala Ile Ala Ser Asn Gly Gly Gly Arg
545                 550                 555                 560

Pro Ala Leu Glu Ser Ile Val Ala Gln Leu Ser Arg Pro Asp Pro Ala
                    565                 570                 575

Leu Ala Ala Leu
            580

<210> SEQ ID NO 12
<211> LENGTH: 1944
<212> TYPE: DNA
<213> ORGANISM: Artificial Sequence
<220> FEATURE:
<223> OTHER INFORMATION: Synthetic

<400> SEQUENCE: 12
```

| | | | | | |
|---|---|---|---|---|---|
| ctgaccccgg | agcaggtggt | ggccatcgct | agtcatgacg | gtggcaaaca | ggctcttgag | 60 |
| accgtccaac | gccttctacc | agttctctgt | caagcccacg | gactaacccc | agcgcaagtt | 120 |
| gtagcgattg | ctagtcatga | cggtggcaaa | caggctcttg | agaccgtcca | acgccttcta | 180 |
| ccagttctct | gtcaagccca | cggactaacc | ccagcgcaag | ttgtagcgat | tgctagtaat | 240 |
| attggtggca | acaggcact | tgagacggtt | cagcgcctcc | ttccagttct | ttgtcaagct | 300 |
| cacggactca | ccccagatca | agttgtagcg | attgctagta | atattggtgg | caaacaggca | 360 |
| cttgagacgg | ttcagcgcct | ccttccagtt | ctttgtcaag | ctcacggact | cacccccagat | 420 |
| caagttgtag | cgattgctag | taacaatggt | ggcaaacagg | ctctcgaaac | cgtacaacga | 480 |
| ctcctcccag | ttctctgtca | agcccacgga | ctaactcctg | atcaagttgt | agcgattgct | 540 |
| agtaatattg | gtggcaaaca | ggcacttgag | acgttcagc | gcctccttcc | agttctttgt | 600 |
| caagctcacg | gactcacccc | agatcaagtt | gtagcgattg | ctagtaatgg | gggtggcaaa | 660 |
| caggctcttg | aaaccgtgca | acgactgctc | cagttctct | gtcaagccca | cggcctcacc | 720 |
| ccggcgcaag | ttgtagcgat | tgctagtaat | ggggggtggca | acaggctct | tgaaaccgtg | 780 |
| caacgactgc | tcccagttct | ctgtcaagcc | cacggcctca | ccccggcgca | agttgtagcg | 840 |
| attgctagtc | atgacggtgg | caaacaggct | cttgagaccg | tccaacgcct | tctaccagtt | 900 |
| ctctgtcaag | cccacggact | aaccccagcg | caagttgtag | cgattgctag | taatgggggt | 960 |

```
ggcaaacagg ctcttgaaac cgtgcaacga ctgctcccag ttctctgtca agcccacggc    1020
ctcaccccgg cgcaagttgt agcgattgct agtaatgggg gtggcaaaca ggctcttgaa    1080
accgtgcaac gactgctccc agttctctgt caagcccacg gcctcacccc ggcgcaagtt    1140
gtagcgattg ctagtaacaa tggtggcaaa caggctctcg aaaccgtaca acgactcctc    1200
ccagttctct gtcaagccca cggactaact cctgatcaag ttgtagcgat tgctagtcat    1260
gacggtggca acaggctct tgagaccgtc aacgccttc taccagttct ctgtcaagcc    1320
cacggactaa ccccagcgca agttgtagcg attgctagta atattggtgg caaacaggca    1380
cttgagacgt tcagcgcct ccttccagtt ctttgtcaag ctcacggact caccccagat    1440
caagttgtag cgattgctag taatattggt ggcaaacagg cacttgagac ggttcagcgc    1500
ctccttccag ttctttgtca agctcacgga ctcaccccag atcaagttgt agcgattgct    1560
agtaatattg gtggcaaaca ggcacttgag acggttcagc gcctccttcc agttctttgt    1620
caagctcacg gactcacccc agatcaagtt gtagcgattg ctagtaacaa tggtggcaaa    1680
caggctctcg aaaccgtaca acgactcctc ccagttctct gtcaagccca cggactaact    1740
cctgatcaag ttgtagcgat tgctagtcat gacggtggca acaggctct tgagaccgtc    1800 caacgccttc taccagttct ctgtcaagcc cacggactaa ccccagcgca agttgtagcg    1860
attgctagta atgcggcgg tcgaccggcg ctggagagca ttgttgccca gttatctcgc    1920
cctgatccgg cgttggccgc gttg                                           1944

<210> SEQ ID NO 13
<211> LENGTH: 1740
<212> TYPE: DNA
<213> ORGANISM: Artificial Sequence
<220> FEATURE:
<223> OTHER INFORMATION: Synthetic

<400> SEQUENCE: 13
ctgaccccgg agcaggtggt ggccatcgct agtcatgacg gtggcaaaca ggctcttgag      60
accgtccaac gccttctacc agttctctgt caagcccacg gactaacccc agcgcaagtt     120
gtagcgattg ctagtaatgg gggtggcaaa caggctcttg aaaccgtgca acgactgctc     180
ccagttctct gtcaagccca cggcctcacc ccggcgcaag ttgtagcgat tgctagtcat     240
gacggtggca acaggctct tgagaccgtc aacgccttc taccagttct ctgtcaagcc     300
cacggactaa ccccagcgca agttgtagcg attgctagtc atgacggtgg caaacaggct     360
cttgagaccg tccaacgcct tctaccagtt ctctgtcaag cccacggact aaccccagcg     420
caagttgtag cgattgctag taatgggggt ggcaaacagg ctcttgaaac cgtgcaacga     480
ctgctcccag ttctctgtca agcccacggc ctcaccccgg cgcaagttgt agcgattgct     540
agtcatgacg gtggcaaaca ggctcttgag accgtccaac gccttctacc agttctctgt     600
caagcccacg gactaacccc agcgcaagtt gtagcgattg ctagtaatat tggtggcaaa     660
caggcacttg agacggttca gcgcctcctt ccagttcttt gtcaagctca cggactcacc     720
ccagatcaag ttgtagcgat tgctagtaat attggtggca acaggcact gagacggtt     780 cagcgcctcc ttccagttct ttgtcaagct cacggactca ccccagatca agttgtagcg     840
attgctagta acaatggtgg caaacaggct ctcgaaaccg tacaacgact cctcccagtt     900
ctctgtcaag cccacggact aactcctgat caagttgtag cgattgctag taatgggggt     960
ggcaaacagg ctcttgaaac cgtgcaacga ctgctcccag ttctctgtca agcccacggc    1020
```

-continued

```
ctcaccccgg cgcaagttgt agcgattgct agtcatgacg gtggcaaaca ggctcttgag    1080
accgtccaac gccttctacc agttctctgt caagcccacg gactaacccc agcgcaagtt    1140
gtagcgattg ctagtaatgg gggtggcaaa caggctcttg aaaccgtgca acgactgctc    1200
ccagttctct gtcaagccca cggcctcacc ccggcgcaag ttgtagcgat tgctagtaat    1260
gggggtggca acaggctctg aaaccgtg caacgactgc tcccagttct ctgtcaagcc    1320
cacggcctca ccccggcgca agttgtagcg attgctagtc atgacggtgg caaacaggct    1380
cttgagaccg tccaacgcct ctaccagtt ctctgtcaag cccacggact aaccccagcg    1440
caagttgtag cgattgctag taatattggt ggcaaacagg cacttgagac ggttcagcgc    1500
ctccttccag ttctttgtca agctcacgga ctcaccccag atcaagttgt agcgattgct    1560
agtaatgggg gtggcaaaca ggctcttgaa accgtgcaac gactgctccc agttctctgt    1620
caagcccacg gcctcacccc ggcgcaagtt gtagcgattg ctagtaatgg cggcggtcga    1680
ccggcgctgg agagcattgt tgcccagtta tctcgccctg atccggcgtt ggccgcgttg    1740
```

<210> SEQ ID NO 14
<211> LENGTH: 1072
<212> TYPE: PRT
<213> ORGANISM: Artificial Sequence
<220> FEATURE:
<223> OTHER INFORMATION: Synthetic

<400> SEQUENCE: 14

```
Met Ala Pro Lys Lys Arg Lys Val Tyr Pro Tyr Asp Val Pro Asp
1               5                   10                  15

Tyr Ala Gly Tyr Pro Tyr Asp Val Pro Asp Tyr Ala Gly Ser Tyr Pro
                20                  25                  30

Tyr Asp Val Pro Asp Tyr Ala Ala His Gly Thr Val Asp Leu Arg Thr
            35                  40                  45

Leu Gly Tyr Ser Gln Gln Gln Gln Glu Lys Ile Lys Pro Lys Val Arg
        50                  55                  60

Ser Thr Val Ala Gln His His Glu Ala Leu Val Gly His Gly Phe Thr
65                  70                  75                  80

His Ala His Ile Val Ala Leu Ser Gln His Pro Ala Ala Leu Gly Thr
                85                  90                  95

Val Ala Val Lys Tyr Gln Asp Met Ile Ala Ala Leu Pro Glu Ala Thr
                100                 105                 110

His Glu Ala Ile Val Gly Val Gly Lys Gln Trp Ser Gly Ala Arg Ala
            115                 120                 125

Leu Glu Ala Leu Leu Thr Val Ala Gly Glu Leu Arg Gly Pro Pro Leu
        130                 135                 140

Gln Leu Asp Thr Gly Gln Leu Leu Lys Ile Ala Lys Arg Gly Gly Val
145                 150                 155                 160

Thr Ala Val Glu Ala Val His Ala Trp Arg Asn Ala Leu Thr Gly Ala
                165                 170                 175

Pro Leu Asn Leu Thr Pro Glu Gln Val Val Ala Ile Ala Ser His Asp
                180                 185                 190

Gly Gly Lys Gln Ala Leu Glu Thr Val Gln Arg Leu Leu Pro Val Leu
            195                 200                 205

Cys Gln Ala His Gly Leu Thr Pro Ala Gln Val Val Ala Ile Ala Ser
        210                 215                 220

His Asp Gly Gly Lys Gln Ala Leu Glu Thr Val Gln Arg Leu Leu Pro
225                 230                 235                 240
```

```
Val Leu Cys Gln Ala His Gly Leu Thr Pro Ala Gln Val Val Ala Ile
                245                 250                 255

Ala Ser Asn Ile Gly Gly Lys Gln Ala Leu Glu Thr Val Gln Arg Leu
            260                 265                 270

Leu Pro Val Leu Cys Gln Ala His Gly Leu Thr Pro Asp Gln Val Val
        275                 280                 285

Ala Ile Ala Ser Asn Ile Gly Gly Lys Gln Ala Leu Glu Thr Val Gln
    290                 295                 300

Arg Leu Leu Pro Val Leu Cys Gln Ala His Gly Leu Thr Pro Asp Gln
305                 310                 315                 320

Val Val Ala Ile Ala Ser Asn Asn Gly Gly Lys Gln Ala Leu Glu Thr
                325                 330                 335

Val Gln Arg Leu Leu Pro Val Leu Cys Gln Ala His Gly Leu Thr Pro
            340                 345                 350

Asp Gln Val Val Ala Ile Ala Ser Asn Ile Gly Gly Lys Gln Ala Leu
        355                 360                 365

Glu Thr Val Gln Arg Leu Leu Pro Val Leu Cys Gln Ala His Gly Leu
    370                 375                 380

Thr Pro Asp Gln Val Val Ala Ile Ala Ser Asn Gly Gly Gly Lys Gln
385                 390                 395                 400

Ala Leu Glu Thr Val Gln Arg Leu Leu Pro Val Leu Cys Gln Ala His
                405                 410                 415

Gly Leu Thr Pro Ala Gln Val Val Ala Ile Ala Ser Asn Gly Gly Gly
            420                 425                 430

Lys Gln Ala Leu Glu Thr Val Gln Arg Leu Leu Pro Val Leu Cys Gln
        435                 440                 445

Ala His Gly Leu Thr Pro Ala Gln Val Val Ala Ile Ala Ser His Asp
    450                 455                 460

Gly Gly Lys Gln Ala Leu Glu Thr Val Gln Arg Leu Leu Pro Val Leu
465                 470                 475                 480

Cys Gln Ala His Gly Leu Thr Pro Ala Gln Val Val Ala Ile Ala Ser
                485                 490                 495

Asn Gly Gly Gly Lys Gln Ala Leu Glu Thr Val Gln Arg Leu Leu Pro
            500                 505                 510

Val Leu Cys Gln Ala His Gly Leu Thr Pro Ala Gln Val Val Ala Ile
        515                 520                 525

Ala Ser Asn Gly Gly Gly Lys Gln Ala Leu Glu Thr Val Gln Arg Leu
    530                 535                 540

Leu Pro Val Leu Cys Gln Ala His Gly Leu Thr Pro Ala Gln Val Val
545                 550                 555                 560

Ala Ile Ala Ser Asn Asn Gly Gly Lys Gln Ala Leu Glu Thr Val Gln
                565                 570                 575

Arg Leu Leu Pro Val Leu Cys Gln Ala His Gly Leu Thr Pro Asp Gln
            580                 585                 590

Val Val Ala Ile Ala Ser His Asp Gly Gly Lys Gln Ala Leu Glu Thr
        595                 600                 605

Val Gln Arg Leu Leu Pro Val Leu Cys Gln Ala His Gly Leu Thr Pro
    610                 615                 620

Ala Gln Val Val Ala Ile Ala Ser Asn Ile Gly Gly Lys Gln Ala Leu
625                 630                 635                 640

Glu Thr Val Gln Arg Leu Leu Pro Val Leu Cys Gln Ala His Gly Leu
                645                 650                 655

Thr Pro Asp Gln Val Val Ala Ile Ala Ser Asn Ile Gly Gly Lys Gln
```

```
                660                 665                 670
Ala Leu Glu Thr Val Gln Arg Leu Leu Pro Val Leu Cys Gln Ala His
            675                 680                 685
Gly Leu Thr Pro Asp Gln Val Val Ala Ile Ala Ser Asn Ile Gly Gly
            690                 695                 700
Lys Gln Ala Leu Glu Thr Val Gln Arg Leu Leu Pro Val Leu Cys Gln
705                 710                 715                 720
Ala His Gly Leu Thr Pro Asp Gln Val Val Ala Ile Ala Ser Asn Asn
                725                 730                 735
Gly Gly Lys Gln Ala Leu Glu Thr Val Gln Arg Leu Leu Pro Val Leu
            740                 745                 750
Cys Gln Ala His Gly Leu Thr Pro Asp Gln Val Val Ala Ile Ala Ser
            755                 760                 765
His Asp Gly Gly Lys Gln Ala Leu Glu Thr Val Gln Arg Leu Leu Pro
        770                 775                 780
Val Leu Cys Gln Ala His Gly Leu Thr Pro Ala Gln Val Val Ala Ile
785                 790                 795                 800
Ala Ser Asn Gly Gly Gly Arg Pro Ala Leu Glu Ser Ile Val Ala Gln
                805                 810                 815
Leu Ser Arg Pro Asp Pro Ala Leu Ala Ala Leu Thr Asn Asp His Leu
            820                 825                 830
Val Ala Leu Ala Cys Leu Gly Gly Arg Pro Ala Leu Asp Ala Val Lys
            835                 840                 845
Lys Gly Leu Pro His Ala Pro Ala Leu Ile Lys Arg Thr Asn Arg Arg
850                 855                 860
Ile Pro Glu Arg Thr Ser His Arg Val Ala Gly Ser Gln Leu Val Lys
865                 870                 875                 880
Ser Glu Leu Glu Glu Lys Lys Ser Glu Leu Arg His Lys Leu Lys Tyr
                885                 890                 895
Val Pro His Glu Tyr Ile Glu Leu Ile Glu Ile Ala Arg Asn Pro Thr
            900                 905                 910
Gln Asp Arg Ile Leu Glu Met Lys Val Met Glu Phe Phe Met Lys Val
            915                 920                 925
Tyr Gly Tyr Arg Gly Glu His Leu Gly Gly Ser Arg Lys Pro Asp Gly
            930                 935                 940
Ala Ile Tyr Thr Val Gly Ser Pro Ile Asp Tyr Gly Val Ile Val Asp
945                 950                 955                 960
Thr Lys Ala Tyr Ser Gly Gly Tyr Asn Leu Pro Ile Gly Gln Ala Arg
                965                 970                 975
Glu Met Gln Arg Tyr Val Glu Glu Asn Gln Thr Arg Asn Lys His Ile
            980                 985                 990
Asn Pro Asn Glu Trp Trp Lys Val Tyr Pro Ser Ser Val Thr Glu Phe
            995                 1000                1005
Lys Phe Leu Phe Val Ser Gly His Phe Lys Gly Asn Tyr Lys Ala
    1010                1015                1020
Gln Leu Thr Arg Leu Asn His Ile Thr Asn Cys Asn Gly Ala Val
    1025                1030                1035
Leu Ser Val Glu Glu Leu Leu Ile Gly Gly Glu Met Ile Lys Ala
    1040                1045                1050
Gly Thr Leu Thr Leu Glu Glu Val Arg Arg Lys Phe Asn Asn Gly
    1055                1060                1065
Glu Ile Asn Phe
    1070
```

<210> SEQ ID NO 15
<211> LENGTH: 3216
<212> TYPE: DNA
<213> ORGANISM: Artificial Sequence
<220> FEATURE:
<223> OTHER INFORMATION: Synthetic

<400> SEQUENCE: 15

```
atggctccaa agaagaagcg taaggtatac ccatacgatg ttcctgacta tgcgggctat      60
ccctatgacg tcccggacta tgcaggatcg tatccatatg acgttccaga ttacgctgct     120
catggtaccg tggatctacg cacgctcggc tacagccagc agcaacagga gaagatcaaa     180
ccgaaggttc gttcgacagt ggcgcagcac acgaggcac tggtcggcca cgggtttaca      240
cacgcgcaca tcgttgcgct cagccaacac ccggcagcgt tagggaccgt cgctgtcaag     300
tatcaggaca tgatcgcagc gttgccagag gcgacacacg aagcgatcgt tggcgtcggc     360
aaacagtggt ccggcgcacg cgctctggag gccttgctca cggtggcggg agagttgaga     420
ggtccaccgt tacagttgga cacaggccaa cttctcaaga ttgcaaaacg tggcggcgtg     480
accgcagtgg aggcagtgca tgcatggcgc aatgcactga cgggtgcccc cctgaacctg     540
accccggagc aggtggtggc catcgctagt catgacggtg caaacaggc tcttgagacc       600
gtccaacgcc ttctaccagt tctctgtcaa gcccacggac taaccccagc gcaagttgta     660
gcgattgcta gtcatgacgg tggcaaacag gctcttgaga ccgtccaacg ccttctacca     720
gttctctgtc aagcccacgg actaaccca gcgcaagttg tagcgattgc tagtaatatt     780
ggtggcaaac aggcacttga cggttcag cgcctccttc cagttctttg tcaagctcac        840
ggactcaccc cagatcaagt gtagcgatt gctagtaata ttggtggcaa acaggcactt     900
gagacggttc agcgcctcct ccagttctt tgtcaagctc acggactcac cccagatcaa      960
gttgtagcga ttgctagtaa caatggtggc aaacaggctc tcgaaaccgt acaacgactc    1020
ctcccagttc tctgtcaagc ccacggacta actcctgatc aagttgtagc gattgctagt    1080
aatattggtg gcaaacaggc acttgagacg gttcagcgcc tccttccagt tctttgtcaa    1140
gctcacggac tcaccccaga tcaagttgta gcgattgcta gtaatggggg tggcaaacag    1200
gctcttgaaa ccgtgcaacg actgctccca gttctctgtc aagcccacgg cctcaccccg    1260
gcgcaagttg tagcgattgc tagtaatggg ggtggcaaac aggctcttga aaccgtgcaa    1320
cgactgctcc cagttctctg tcaagcccac ggcctcaccc cggcgcaagt tgtagcgatt    1380
gctagtcatg acggtggcaa acaggctctt gagaccgtcc aacgccttct accagttctc    1440
tgtcaagccc acggactaac cccagcgcaa gttgtagcga ttgctagtaa tgggggtggc    1500
aaacaggctc ttgaaaccgt gcaacgactg ctcccagttc tctgtcaagc ccacggcctc    1560
accccggcgc aagttgtagc gattgctagt aatgggggtg gcaaacaggc tcttgaaacc    1620
gtgcaacgac tgctcccagt tctctgtcaa gcccacggcc tcaccccggc gcaagttgta    1680
gcgattgcta gtaacaatgg tggcaaacag gctctcgaaa ccgtacaacg actcctccca    1740
gttctctgtc aagcccacgg actaactcct gatcaagttg tagcgattgc tagtcatgac    1800
ggtggcaaac aggctcttga gaccgtccaa cgccttctac cagttctctg tcaagcccac    1860
ggactaaccc cagcgcaagt gtagcgatt gctagtaata ttggtggcaa acaggcactt     1920
gagacggttc agcgcctcct ccagttctt tgtcaagctc acggactcac cccagatcaa     1980
gttgtagcga ttgctagtaa tattggtggc aaacaggcac ttgagacggt tcagcgcctc    2040
```

-continued

```
cttccagttc tttgtcaagc tcacggactc accccagatc aagttgtagc gattgctagt    2100
aatattggtg gcaaacaggc acttgagacg gttcagcgcc tccttccagt tctttgtcaa    2160
gctcacggac tcaccccaga tcaagttgta gcgattgcta gtaacaatgg tggcaaacag    2220
gctctcgaaa ccgtacaacg actcctccca gttctctgtc aagcccacgg actaactcct    2280
gatcaagttg tagcgattgc tagtcatgac ggtggcaaac aggctcttga ccgtccaa     2340 cgccttctac cagttctctg tcaagcccac ggactaaccc cagcgcaagt tgtagcgatt    2400
gctagtaatg gcggcggtcg accggcgctg gagagcattg ttgcccagtt atctcgccct    2460
gatccggcgt tggccgcgtt gaccaacgac cacctcgtcg ccttggcctg cctcggcgga    2520
cgtcctgcgc tggatgcagt gaaaaaggga ttgccgcacg cgccggcctt gatcaaaaga    2580
accaatcgcc gtattcccga acgcacatcc catcgcgttg ccggatccca actagtcaaa    2640
agtgaactgg aggagaagaa atctgaactt cgtcataaat tgaaatatgt gcctcatgaa    2700
tatattgaat taattgaaat tgccagaaat cccactcagg atagaattct tgaaatgaag    2760
gtaatggaat tttttatgaa agtttatgga tatagaggtg agcatttggg tggatcaagg    2820
aaaccggacg gagcaattta tactgtcgga tctcctattg attacggtgt gatcgtggat    2880
actaaggctt atagcggagg ttataatctg ccaattggcc aagcacgaga aatgcaacga    2940
tatgtcgaag aaaatcaaac acgaaacaaa catatcaacc ctaatgaatg gtggaaagtc    3000
tatccatctt ctgtaacgga atttaagttt ttatttgtga gtggtcactt taaaggaaac    3060
tacaaagctc agcttacacg attaaatcat atcactaatt gtaatggagc tgttcttagt    3120
gtagaagagc ttttaattgg tggagaaatg attaaagccg gcacattaac cttagaggaa    3180
gtgagacgga aatttaataa cggcgagata aacttt                              3216
```

<210> SEQ ID NO 16
<211> LENGTH: 1004
<212> TYPE: PRT
<213> ORGANISM: Artificial Sequence
<220> FEATURE:
<223> OTHER INFORMATION: Synthetic

<400> SEQUENCE: 16

```
Met Ala Pro Lys Lys Arg Lys Val Tyr Pro Tyr Asp Val Pro Asp
1               5                   10                  15

Tyr Ala Gly Tyr Pro Tyr Asp Val Pro Asp Tyr Ala Gly Ser Tyr Pro
            20                  25                  30

Tyr Asp Val Pro Asp Tyr Ala Ala His Gly Thr Val Asp Leu Arg Thr
        35                  40                  45

Leu Gly Tyr Ser Gln Gln Gln Gln Glu Lys Ile Lys Pro Lys Val Arg
    50                  55                  60

Ser Thr Val Ala Gln His His Glu Ala Leu Val Gly His Gly Phe Thr
65                  70                  75                  80

His Ala His Ile Val Ala Leu Ser Gln His Pro Ala Ala Leu Gly Thr
                85                  90                  95

Val Ala Val Lys Tyr Gln Asp Met Ile Ala Ala Leu Pro Glu Ala Thr
            100                 105                 110

His Glu Ala Ile Val Gly Val Gly Lys Gln Trp Ser Gly Ala Arg Ala
        115                 120                 125

Leu Glu Ala Leu Leu Thr Val Ala Gly Glu Leu Arg Gly Pro Pro Leu
    130                 135                 140

Gln Leu Asp Thr Gly Gln Leu Leu Lys Ile Ala Lys Arg Gly Gly Val
145                 150                 155                 160
```

```
Thr Ala Val Glu Ala Val His Ala Trp Arg Asn Ala Leu Thr Gly Ala
            165                 170                 175

Pro Leu Asn Leu Thr Pro Glu Gln Val Ala Ile Ala Ser His Asp
            180                 185                 190

Gly Gly Lys Gln Ala Leu Glu Thr Val Gln Arg Leu Leu Pro Val Leu
            195                 200                 205

Cys Gln Ala His Gly Leu Thr Pro Ala Gln Val Val Ala Ile Ala Ser
            210                 215                 220

Asn Gly Gly Gly Lys Gln Ala Leu Glu Thr Val Gln Arg Leu Leu Pro
225                 230                 235                 240

Val Leu Cys Gln Ala His Gly Leu Thr Pro Ala Gln Val Val Ala Ile
            245                 250                 255

Ala Ser His Asp Gly Gly Lys Gln Ala Leu Glu Thr Val Gln Arg Leu
            260                 265                 270

Leu Pro Val Leu Cys Gln Ala His Gly Leu Thr Pro Ala Gln Val Val
            275                 280                 285

Ala Ile Ala Ser His Asp Gly Gly Lys Gln Ala Leu Glu Thr Val Gln
            290                 295                 300

Arg Leu Leu Pro Val Leu Cys Gln Ala His Gly Leu Thr Pro Ala Gln
305                 310                 315                 320

Val Val Ala Ile Ala Ser Asn Gly Gly Gly Lys Gln Ala Leu Glu Thr
            325                 330                 335

Val Gln Arg Leu Leu Pro Val Leu Cys Gln Ala His Gly Leu Thr Pro
            340                 345                 350

Ala Gln Val Val Ala Ile Ala Ser His Asp Gly Gly Lys Gln Ala Leu
            355                 360                 365

Glu Thr Val Gln Arg Leu Leu Pro Val Leu Cys Gln Ala His Gly Leu
            370                 375                 380

Thr Pro Ala Gln Val Val Ala Ile Ala Ser Asn Ile Gly Gly Lys Gln
385                 390                 395                 400

Ala Leu Glu Thr Val Gln Arg Leu Leu Pro Val Leu Cys Gln Ala His
            405                 410                 415

Gly Leu Thr Pro Asp Gln Val Val Ala Ile Ala Ser Asn Ile Gly Gly
            420                 425                 430

Lys Gln Ala Leu Glu Thr Val Gln Arg Leu Leu Pro Val Leu Cys Gln
            435                 440                 445

Ala His Gly Leu Thr Pro Asp Gln Val Val Ala Ile Ala Ser Asn Asn
            450                 455                 460

Gly Gly Lys Gln Ala Leu Glu Thr Val Gln Arg Leu Leu Pro Val Leu
465                 470                 475                 480

Cys Gln Ala His Gly Leu Thr Pro Asp Gln Val Val Ala Ile Ala Ser
            485                 490                 495

Asn Gly Gly Gly Lys Gln Ala Leu Glu Thr Val Gln Arg Leu Leu Pro
            500                 505                 510

Val Leu Cys Gln Ala His Gly Leu Thr Pro Ala Gln Val Val Ala Ile
            515                 520                 525

Ala Ser His Asp Gly Gly Lys Gln Ala Leu Glu Thr Val Gln Arg Leu
            530                 535                 540

Leu Pro Val Leu Cys Gln Ala His Gly Leu Thr Pro Ala Gln Val Val
545                 550                 555                 560

Ala Ile Ala Ser Asn Gly Gly Gly Lys Gln Ala Leu Glu Thr Val Gln
            565                 570                 575
```

```
Arg Leu Leu Pro Val Leu Cys Gln Ala His Gly Leu Thr Pro Ala Gln
            580                 585                 590

Val Val Ala Ile Ala Ser Asn Gly Gly Gly Lys Gln Ala Leu Glu Thr
        595                 600                 605

Val Gln Arg Leu Leu Pro Val Leu Cys Gln Ala His Gly Leu Thr Pro
    610                 615                 620

Ala Gln Val Val Ala Ile Ala Ser His Asp Gly Gly Lys Gln Ala Leu
625                 630                 635                 640

Glu Thr Val Gln Arg Leu Leu Pro Val Leu Cys Gln Ala His Gly Leu
            645                 650                 655

Thr Pro Ala Gln Val Val Ala Ile Ala Ser Asn Ile Gly Gly Lys Gln
        660                 665                 670

Ala Leu Glu Thr Val Gln Arg Leu Leu Pro Val Leu Cys Gln Ala His
    675                 680                 685

Gly Leu Thr Pro Asp Gln Val Val Ala Ile Ala Ser Asn Gly Gly Gly
690                 695                 700

Lys Gln Ala Leu Glu Thr Val Gln Arg Leu Leu Pro Val Leu Cys Gln
705                 710                 715                 720

Ala His Gly Leu Thr Pro Ala Gln Val Val Ala Ile Ala Ser Asn Gly
            725                 730                 735

Gly Gly Arg Pro Ala Leu Glu Ser Ile Val Ala Gln Leu Ser Arg Pro
        740                 745                 750

Asp Pro Ala Leu Ala Ala Leu Thr Asn Asp His Leu Val Ala Leu Ala
    755                 760                 765

Cys Leu Gly Gly Arg Pro Ala Leu Asp Ala Val Lys Lys Gly Leu Pro
770                 775                 780

His Ala Pro Ala Leu Ile Lys Arg Thr Asn Arg Arg Ile Pro Glu Arg
785                 790                 795                 800

Thr Ser His Arg Val Ala Gly Ser Gln Leu Val Lys Ser Glu Leu Glu
            805                 810                 815

Glu Lys Lys Ser Glu Leu Arg His Lys Leu Lys Tyr Val Pro His Glu
        820                 825                 830

Tyr Ile Glu Leu Ile Glu Ile Ala Arg Asn Pro Thr Gln Asp Arg Ile
    835                 840                 845

Leu Glu Met Lys Val Met Glu Phe Phe Met Lys Val Tyr Gly Tyr Arg
850                 855                 860

Gly Glu His Leu Gly Gly Ser Arg Lys Pro Asp Gly Ala Ile Tyr Thr
865                 870                 875                 880

Val Gly Ser Pro Ile Asp Tyr Gly Val Ile Val Asp Thr Lys Ala Tyr
            885                 890                 895

Ser Gly Gly Tyr Asn Leu Pro Ile Gly Gln Ala Asp Ala Met Gln Ser
        900                 905                 910

Tyr Val Glu Glu Asn Gln Thr Arg Asn Lys His Ile Asn Pro Asn Glu
    915                 920                 925

Trp Trp Lys Val Tyr Pro Ser Ser Val Thr Glu Phe Lys Phe Leu Phe
930                 935                 940

Val Ser Gly His Phe Lys Gly Asn Tyr Lys Ala Gln Leu Thr Arg Leu
945                 950                 955                 960

Asn His Ile Thr Asn Cys Asn Gly Ala Val Leu Ser Val Glu Glu Leu
            965                 970                 975

Leu Ile Gly Gly Glu Met Ile Lys Ala Gly Thr Leu Thr Leu Glu Glu
        980                 985                 990

Val Arg Arg Lys Phe Asn Asn Gly  Glu Ile Asn Phe
```

995            1000

<210> SEQ ID NO 17
<211> LENGTH: 7114
<212> TYPE: DNA
<213> ORGANISM: Artificial Sequence
<220> FEATURE:
<223> OTHER INFORMATION: Synthetic

<400> SEQUENCE: 17

| | | | | | |
|---|---|---|---|---|---|
| cgccattctg | cctggggacg | tcggagcaag | cttgatttag | gtgacactat | agaatacaag | 60 |
| ctacttgttc | tttttgcagg | atctgccacc | atggctccaa | gaagaagcg | taaggtatac | 120 |
| ccatacgatg | ttcctgacta | tgcgggctat | ccctatgacg | tcccggacta | tgcaggatcg | 180 |
| tatccatatg | acgttccaga | ttacgctgct | catggtaccg | tggatctacg | cacgctcggc | 240 |
| tacagccagc | agcaacagga | gaagatcaaa | ccgaaggttc | gttcgacagt | ggcgcagcac | 300 |
| cacgaggcac | tggtcggcca | cgggtttaca | cacgcgcaca | tcgttgcgct | cagccaacac | 360 |
| ccggcagcgt | tagggaccgt | cgctgtcaag | tatcaggaca | tgatcgcagc | gttgccagag | 420 |
| gcgacacacg | aagcgatcgt | tggcgtcggc | aaacagtggt | ccggcgcacg | cgctctggag | 480 |
| gccttgctca | cggtggcggg | agagttgaga | ggtccaccgt | tacagttgga | cacaggccaa | 540 |
| cttctcaaga | ttgcaaaacg | tggcggcgtg | accgcagtgg | aggcagtgca | tgcatggcgc | 600 |
| aatgcactga | cgggtgcccc | cctgaacctg | accccggagc | aggtggtggc | catcgctagt | 660 |
| catgacggtg | gcaaacaggc | tcttgagacc | gtccaacgcc | ttctaccagt | tctctgtcaa | 720 |
| gcccacggac | taaccccagc | gcaagttgta | gcgattgcta | gtaatggggg | tggcaaacag | 780 |
| gctcttgaaa | ccgtgcaacg | actgctccca | gttctctgtc | aagcccacgg | cctcaccccg | 840 |
| gcgcaagttg | tagcgattgc | tagtcatgac | ggtggcaaac | aggctcttga | gaccgtccaa | 900 |
| cgccttctac | cagttctctg | tcaagcccac | ggactaaccc | cagcgcaagt | tgtagcgatt | 960 |
| gctagtcatg | acggtggcaa | acaggctctt | gagaccgtcc | aacgccttct | accagttctc | 1020 |
| tgtcaagccc | acggactaac | cccagcgcaa | gttgtagcga | ttgctagtaa | tggggtggc | 1080 |
| aaacaggctc | ttgaaaccgt | gcaacgactg | ctcccagttc | tctgtcaagc | ccacggcctc | 1140 |
| accccggcgc | aagttgtagc | gattgctagt | catgacggtg | gcaaacaggc | tcttgagacc | 1200 |
| gtccaacgcc | ttctaccagt | tctctgtcaa | gcccacggac | taaccccagc | gcaagttgta | 1260 |
| gcgattgcta | gtaatattgg | tggcaaacag | gcacttgaga | cggttcagcg | cctccttcca | 1320 |
| gttctttgtc | aagctcacgg | actcacccca | gatcaagttg | tagcgattgc | tagtaatatt | 1380 |
| ggtggcaaac | aggcacttga | gacggttcag | cgcctccttc | cagttctttg | tcaagctcac | 1440 |
| ggactcaccc | cagatcaagt | tgtagcgatt | gctagtaaca | atggtggcaa | acaggctctc | 1500 |
| gaaaccgtac | aacgactcct | cccagttctc | tgtcaagccc | acggactaac | tcctgatcaa | 1560 |
| gttgtagcga | ttgctagtaa | tggggtggc | aaacaggctc | ttgaaaccgt | gcaacgactg | 1620 |
| ctcccagttc | tctgtcaagc | ccacggcctc | accccggcgc | aagttgtagc | gattgctagt | 1680 |
| catgacggtg | gcaaacaggc | tcttgagacc | gtccaacgcc | ttctaccagt | tctctgtcaa | 1740 |
| gcccacggac | taaccccagc | gcaagttgta | gcgattgcta | gtaatggggg | tggcaaacag | 1800 |
| gctcttgaaa | ccgtgcaacg | actgctccca | gttctctgtc | aagcccacgg | cctcaccccg | 1860 |
| gcgcaagttg | tagcgattgc | tagtaatggg | ggtggcaaac | aggctcttga | aaccgtgcaa | 1920 |
| cgactgctcc | cagttctctg | tcaagcccac | ggcctcaccc | cggcgcaagt | tgtagcgatt | 1980 |
| gctagtcatg | acggtggcaa | acaggctctt | gagaccgtcc | aacgccttct | accagttctc | 2040 |

```
tgtcaagccc acggactaac cccagcgcaa gttgtagcga ttgctagtaa tattggtggc  2100
aaacaggcac ttgagacggt tcagcgcctc cttccagttc tttgtcaagc tcacggactc  2160
accccagatc aagttgtagc gattgctagt aatggggtg gcaaacaggc tcttgaaacc  2220
gtgcaacgac tgctcccagt tctctgtcaa gcccacggcc tcaccccggc gcaagttgta  2280
gcgattgcta gtaatggcgg cggtcgaccg gcgctggaga gcattgttgc ccagttatct  2340
cgccctgatc cggcgttggc cgcgttgacc aacgaccacc tcgtcgcctt ggcctgcctc  2400
ggcggacgtc ctgcgctgga tgcagtgaaa aagggattgc cgcacgcgcc ggccttgatc  2460
aaaagaacca atcgccgtat tcccgaacgc acatcccatc gcgttgccgg atcccaacta  2520
gtcaaaagtg aactggagga gaagaaatct gaacttcgtc ataaattgaa atatgtgcct  2580
catgaatata ttgaattaat tgaaattgcc agaaatccca ctcaggatag aattcttgaa  2640
atgaaggtaa tggaattttt tatgaaagtt tatggatata gaggtgagca tttgggtgga  2700
tcaaggaaac cggacggagc aatttatact gtcggatctc ctattgatta cggtgtgatc  2760
gtggatacta agcttatag cggaggttat aatctgccaa ttggccaagc agatgccatg  2820
caaagctatg tcgaagaaaa tcaaacacga acaaacata tcaaccctaa tgaatggtgg  2880
aaagtctatc catcttctgt aacggaattt aagttttat ttgtgagtgg tcactttaaa  2940
ggaaactaca aagctcagct tacacgatta atcatatca ctaattgtaa tggagctgtt  3000
cttagtgtag aagagctttt aattggtgga gaaatgatta agccggcac attaaccta  3060 gaggaagtga gacggaaatt taataacggc gagataaact tttaatctag aactatagtg  3120
agtcgtatta cgtagatcca gacatgataa gatacattga tgagtttgga caaaccacaa  3180
ctagaatgca gtgaaaaaaa tgctttattt gtgaaatttg tgatgctatt gctttatttg  3240
taaccattat aagctgcaat aaacaagtta acaacaacaa ttgcattcat tttatgtttc  3300
aggttcaggg ggaggtgtgg gaggtttttt aattcgcggc cgcggcgcca atgcattggg  3360
cccggtacgt acccagcttt tgttcccttt agtgagggt aattgcgcgc ttggcgtaat  3420
catggtcata gctgtttcct gtgtgaaatt gttatccgct cacaattcca cacaacatac  3480
gagccggaag cataaagtgt aaagcctggg gtgcctaatg agtgagctaa ctcacattaa  3540
ttgcgttgcg ctcactgccc gctttccagt cgggaaacct gtcgtgccag ctgcattaat  3600
gaatcggcca acgcgcgggg agaggcggtt tgcgtattgg gcgctcttcc gcttcctcgc  3660
tcactgactc gctgcgctcg gtcgttcggc tgcggcgagc ggtatcagct cactcaaagg  3720
cggtaatacg gttatccaca gaatcagggg ataacgcagg aaagaacatg tgagcaaaag  3780
gccagcaaaa ggccaggaac cgtaaaaagg ccgcgttgct ggcgtttttc cataggctcc  3840
gcccccctga cgagcatcac aaaaatcgac gctcaagtca gaggtggcga acccgacag  3900 gactataaag ataccaggcg tttccccctg gaagctccct cgtgcgctct cctgttccga  3960
ccctgccgct taccggatac ctgtccgcct ttctcccttc gggaagcgtg gcgctttctc  4020
atagctcacg ctgtaggtat ctcagttcgg tgtaggtcgt tcgctccaag ctgggctgtg  4080
tgcacgaacc ccccgttcag cccgaccgct gcgccttatc cggtaactat cgtcttgagt  4140
ccaacccggt aagacacgac ttatcgccac tggcagcagc cactggtaac aggattagca  4200
gagcgaggta tgtaggcggt gctacagagt tcttgaagtg gtggcctaac tacggctaca  4260
ctagaaggac agtatttggt atctgcgctc tgctgaagcc agttaccttc ggaaaaagag  4320
ttggtagctc ttgatccggc aaacaaacca ccgctggtag cggtggtttt tttgtttgca  4380
```

-continued

```
agcagcagat tacgcgcaga aaaaaaggat ctcaagaaga tcctttgatc ttttctacgg    4440
ggtctgacgc tcagtggaac gaaaactcac gttaagggat tttggtcatg agattatcaa    4500
aaaggatctt cacctagatc cttttaaatt aaaaatgaag ttttaaatca atctaaagta    4560
tatatgagta aacttggtct gacagttacc aatgcttaat cagtgaggca cctatctcag    4620
cgatctgtct atttcgttca tccatagttg cctgactccc cgtcgtgtag ataactacga    4680
tacgggaggg cttaccatct ggccccagtg ctgcaatgat accgcgagac ccacgctcac    4740
cggctccaga tttatcagca ataaaccagc cagccggaag ggccgagcgc agaagtggtc    4800
ctgcaacttt atccgcctcc atccagtcta ttaattgttg ccgggaagct agagtaagta    4860
gttcgccagt taatagtttg cgcaacgttg ttgccattgc tacaggcatc gtggtgtcac    4920
gctcgtcgtt tggtatggct tcattcagct ccggttccca acgatcaagg cgagttacat    4980 gatccccat gttgtgcaaa aaagcggtta gctccttcgg tcctccgatc gttgtcagaa    5040
gtaagttggc cgcagtgtta tcactcatgg ttatggcagc actgcataat tctcttactg    5100
tcatgccatc cgtaagatgc ttttctgtga ctggtgagta ctcaaccaag tcattctgag    5160
aatagtgtat gcggcgaccg agttgctctt gcccggcgtc aatacgggat aataccgcgc    5220
cacatagcag aactttaaaa gtgctcatca ttggaaaacg ttcttcgggg cgaaaactct    5280
caaggatctt accgctgttg agatccagtt cgatgtaacc cactcgtgca cccaactgat    5340
cttcagcatc ttttactttc accagcgttt ctgggtgagc aaaaacagga aggcaaaatg    5400
ccgcaaaaaa gggaataagg gcgacacgga aatgttgaat actcatactc ttcctttttc    5460
aatattattg aagcatttat cagggttatt gtctcatgag cggatacata tttgaatgta    5520
tttagaaaaa taaacaaata ggggttccgc gcacatttcc ccgaaaagtg ccacctaaat    5580
tgtaagcgtt aatattttgt taaaattcgc gttaaatttt tgttaaatca gctcattttt    5640
taaccaatag gccgaaatcg gcaaaatccc ttataaatca aaagaataga ccgagatagg    5700
gttgagtgtt gttccagttt ggaacaagag tccactatta agaacgtgg actccaacgt     5760 caaagggcga aaaccgtct atcagggcga tggcccacta cgtgaaccat cacccctaatc    5820 aagttttttg gggtcgaggt gccgtaaagc actaaatcgg aaccctaaag ggagcccccg    5880
atttagagct tgacggggaa agccggcgaa cgtggcgaga aggaaggga agaaagcgaa    5940 aggagcgggc gctagggcgc tggcaagtgt agcggtcacg ctgcgcgtaa ccaccacacc    6000
cgccgcgctt aatgcgccgc tacagggcgc gtcccattcg ccattcaggc tgcgcaactg    6060
ttgggaaggg cgatcggtgc gggcctcttc gctattacgc cagtcgatta tatactcgag    6120
atatatttcg accatagcca attcaatatg gcgtatatgg actcatgcca attcaatatg    6180
gtggatctgg acctgtgcca attcaatatg gcgtatatgg actcgtgcca attcaatatg    6240
gtggatctgg accccagcca attcaatatg gcggacttgg caccatgcca attcaatatg    6300
gcggacttgg cactgtgcca actggggagg ggtctacttg gcacggtgcc aagtttgagg    6360
aggggtcttg gccctgtgcc aagtccgcca tattgaattg gcatggtgcc aataatggcg    6420
gccatattgg ctatatgcca ggatcaatat ataggcaata ccaatatgg ccctatgcca    6480 atatggctat tggccaggtt caatactatg tattggccct atgccatata gtattccata    6540
tatgggtttt cctattgacg tagatagccc ctcccaatgg gcggtcccat ataccatata    6600 tgggcttcc taataccgcc catagccact ccccattga cgtcaatggt ctctatatat     6660 ggtcttcct attgacgtca tatgggcggt cctattgacg tatatggcgc ctcccccatt    6720
gacgtcaatt acggtaaatg gcccgcctgg ctcaatgccc attgacgtca ataggaccac    6780
```

```
ccaccattga cgtcaatggg atggctcatt gcccattcat atccgttctc acgcccccta    6840
ttgacgtcaa tgacggtaaa tggcccactt ggcagtacat caatatctat taatagtaac    6900
ttggcaagta cattactatt ggaaggacgc cagggtacat tggcagtact cccattgacg    6960
tcaatggcgg taaatggccc gcgatggctg ccaagtacat ccccattgac gtcaatgggg    7020
aggggcaatg acgcaaatgg gcgttccatt gacgtaaatg gcggtaggc gtgcctaatg    7080 ggaggtctat ataagcaatg ctcgtttagg gaac                                7114
```

<210> SEQ ID NO 18
<211> LENGTH: 213
<212> TYPE: PRT
<213> ORGANISM: Artificial Sequence
<220> FEATURE:
<223> OTHER INFORMATION: Synthetic

<400> SEQUENCE: 18

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
                20                  25                  30

His Trp Phe Gln Gln Lys Pro Gly Ser Ser Pro Lys Pro Trp Ile Tyr
            35                  40                  45

Ala Thr Ser Asn Leu Ala Ser Gly Val Pro Val Arg Phe Ser Gly Ser
        50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 19
<211> LENGTH: 451
<212> TYPE: PRT
<213> ORGANISM: Artificial Sequence
<220> FEATURE:
<223> OTHER INFORMATION: Synthetic

<400> SEQUENCE: 19

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr

-continued

```
                20                  25                  30
Asn Met His Trp Val Lys Gln Thr Pro Gly Arg Gly Leu Glu Trp Ile
         35                  40                  45
Gly Ala Ile Tyr Pro Gly Asn Gly Asp Thr Ser Tyr Asn Gln Lys Phe
     50                  55                  60
Lys Gly Lys Ala Thr Leu Thr Ala Asp Lys Ser Ser Thr Ala Tyr
 65                  70                  75                  80
Met Gln Leu Ser Ser Leu Thr Ser Glu Asp Ser Ala Val Tyr Tyr Cys
                 85                  90                  95
Ala Arg Ser Thr Tyr Tyr Gly Gly Asp Trp Tyr Phe Asn Val Trp Gly
             100                 105                 110
Ala Gly Thr Thr Val Thr Val Ser Ala Ala Ser Thr Lys Gly Pro Ser
             115                 120                 125
Val Phe Pro Leu Ala Pro Ser Ser Lys Ser Thr Ser Gly Gly Thr Ala
             130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                 165                 170                 175
Val Leu Gln Ser Ser Gly Leu Tyr Ser Leu Ser Ser Val Val Thr Val
             180                 185                 190
Pro Ser Ser Ser Leu Gly Thr Gln Thr Tyr Ile Cys Asn Val Asn His
             195                 200                 205
Lys Pro Ser Asn Thr Lys Val Asp Lys Lys Ala Glu Pro Lys Ser Cys
         210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                 245                 250                 255
Ile Ser Arg Thr Pro Glu Val Thr Cys Val Val Val Asp Val Ser His
             260                 265                 270
Glu Asp Pro Glu Val Lys Phe Asn Trp Tyr Val Asp Gly Val Glu Val
         275                 280                 285
His Asn Ala Lys Thr Lys Pro Arg Glu Glu Gln Tyr Asn Ser Thr Tyr
     290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                 325                 330                 335
Glu Lys Thr Ile Ser Lys Ala Lys Gly Gln Pro Arg Glu Pro Gln Val
             340                 345                 350
Tyr Thr Leu Pro Pro Ser Arg Asp Glu Leu Thr Lys Asn Gln Val Ser
             355                 360                 365
Leu Thr Cys Leu Val Lys Gly Phe Tyr Pro Ser Asp Ile Ala Val Glu
         370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                 405                 410                 415
Asp Lys Ser Arg Trp Gln Gln Gly Asn Val Phe Ser Cys Ser Val Met
             420                 425                 430
His Glu Ala Leu His Asn His Tyr Thr Gln Lys Ser Leu Ser Leu Ser
             435                 440                 445
```

Pro Gly Lys
    450

<210> SEQ ID NO 20
<211> LENGTH: 113
<212> TYPE: PRT
<213> ORGANISM: Artificial Sequence
<220> FEATURE:
<223> OTHER INFORMATION: Synthetic

<400> SEQUENCE: 20

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
            100                 105                 110

Arg

<210> SEQ ID NO 21
<211> LENGTH: 449
<212> TYPE: PRT
<213> ORGANISM: Artificial Sequence
<220> FEATURE:
<223> OTHER INFORMATION: Synthetic

<400> SEQUENCE: 21

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

```
Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 22
<211> LENGTH: 214
<212> TYPE: PRT
<213> ORGANISM: Artificial Sequence
<220> FEATURE:
<223> OTHER INFORMATION: Synthetic

<400> SEQUENCE: 22

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80
```

Glu Asp Phe Ala Val Tyr Tyr Cys Gln Gln Arg Ser Asn Trp Pro Ile
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 23
<211> LENGTH: 452
<212> TYPE: PRT
<213> ORGANISM: Artificial Sequence
<220> FEATURE:
<223> OTHER INFORMATION: Synthetic

<400> SEQUENCE: 23

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asn Asp Tyr
            20                  25                  30

Ala Met His Trp Val Arg Gln Ala Pro Gly Lys Gly Leu Glu Trp Val
        35                  40                  45

Ser Thr Ile Ser Trp Asn Ser Gly Ser Ile Gly Tyr Ala Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ile Gln Tyr Gly Asn Tyr Tyr Tyr Gly Met Asp Val Trp
            100                 105                 110

Gly Gln Gly Thr Thr Val Thr Val Ser Ser Ala Ser Thr Lys Gly Pro
            115                 120                 125

Ser Val Phe Pro Leu Ala Pro Gly Ser Ser Lys Ser Thr Ser Gly Thr
            130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Lys Val Glu Pro Lys Ser
            210                 215                 220

```
Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
        450

<210> SEQ ID NO 24
<211> LENGTH: 214
<212> TYPE: PRT
<213> ORGANISM: Artificial Sequence
<220> FEATURE:
<223> OTHER INFORMATION: Synthetic

<400> SEQUENCE: 24

Asp Ile Gln Met Thr Gln Ser Pro Ser Ser Leu Ser Ala Ser Val Gly
1               5                  10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln His Phe Asp His Leu Pro Leu
            85                  90                  95

Ala Phe Gly Gly Gly Thr Lys Val Glu Ile Lys Arg Thr Val Ala Ala
        100                 105                 110

Pro Ser Val Phe Ile Phe Pro Pro Ser Asp Glu Gln Leu Lys Ser Gly
    115                 120                 125
```

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 25
<211> LENGTH: 449
<212> TYPE: PRT
<213> ORGANISM: Artificial Sequence
<220> FEATURE:
<223> OTHER INFORMATION: Synthetic

<400> SEQUENCE: 25

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Asp Tyr Tyr Trp Thr Trp Ile Arg Gln Ser Pro Gly Lys Gly Leu Glu
        35                  40                  45

Trp Ile Gly His Ile Tyr Tyr Ser Gly Asn Thr Asn Tyr Asn Pro Ser
50                  55                  60

Leu Lys Ser Arg Leu Thr Ile Ser Ile Asp Thr Ser Lys Thr Gln Phe
65                  70                  75                  80

Ser Leu Lys Leu Ser Ser Val Thr Ala Ala Asp Thr Ala Ile Tyr Tyr
                85                  90                  95

Cys Val Arg Asp Arg Val Thr Gly Ala Phe Asp Ile Trp Gly Gln Gly
            100                 105                 110

Thr Thr Val Thr Val Ser Ser Ala Cys Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270
```

```
Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 26
<211> LENGTH: 214
<212> TYPE: PRT
<213> ORGANISM: Artificial Sequence
<220> FEATURE:
<223> OTHER INFORMATION: Synthetic

<400> SEQUENCE: 26

Asp Ile Gln Leu Thr Gln Ser Pro Ser Ser Leu Ser Ala Ser Val Gly
1               5                   10                  15

Asp Arg Val Ser Ile Thr Cys Lys Ala Ser Gln Asp Val Ser Ile Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln His Tyr Ile Thr Pro Leu
                85                  90                  95

Thr Phe Gly Ala Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
```

```
                180                 185                 190
Ala Cys Glu Val Thr His Gln Gly Leu Ser Ser Pro Val Thr Lys Ser
            195                 200                 205

Phe Asn Arg Gly Glu Cys
    210

<210> SEQ ID NO 27
<211> LENGTH: 451
<212> TYPE: PRT
<213> ORGANISM: Artificial Sequence
<220> FEATURE:
<223> OTHER INFORMATION: Synthetic

<400> SEQUENCE: 27

Gln Val Gln Leu Gln Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
                20                  25                  30

Gly Met Asn Trp Val Lys Gln Ala Pro Gly Gln Gly Leu Lys Trp Met
            35                  40                  45

Gly Trp Ile Asn Thr Tyr Thr Gly Glu Pro Thr Tyr Thr Asp Asp Phe
    50                  55                  60

Lys Gly Arg Phe Ala Phe Ser Leu Asp Thr Ser Val Ser Thr Ala Tyr
65                  70                  75                  80

Leu Gln Ile Ser Ser Leu Lys Ala Asp Asp Thr Ala Val Tyr Phe Cys
                85                  90                  95

Ala Arg Gly Gly Phe Gly Ser Ser Tyr Trp Tyr Phe Asp Val Trp Gly
            100                 105                 110

Gln Gly Thr Leu Val Thr Val Ser Ser Cys Ser Thr Lys Gly Pro Ser
    115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
    195                 200                 205

Lys Pro Ser Asn Thr Lys Val Asp Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
    275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
```

```
                    325                 330                 335
Glu Lys Thr Ile Ser Lys Ala Lys Gly Gln Pro Arg Glu Pro Gln Val
        340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 28
<211> LENGTH: 203
<212> TYPE: DNA
<213> ORGANISM: Artificial Sequence
<220> FEATURE:
<223> OTHER INFORMATION: Synthetic

<400> SEQUENCE: 28
atgcgggcat ggactggttc ctggcgttgg attatgctca ttcttttgc ctggggggacc      60 ttattgtttt ataggtgg tcatttggtt cgagataatg accaccctga ccattctagc      120
agagaactct ccaagattct tgcaaagctg gagcgcttaa acaacaaaat gaagacttga      180
ggagaatggc tgagtctctc cgg                                              203

<210> SEQ ID NO 29
<211> LENGTH: 90
<212> TYPE: DNA
<213> ORGANISM: Artificial Sequence
<220> FEATURE:
<223> OTHER INFORMATION: Synthetic

<400> SEQUENCE: 29
aagattcttg caaagctgga gcgcttaaac aacaaaatga gacttgagg agaatggctg       60 agtctctccg gtaggtttga aatactcaag                                       90

<210> SEQ ID NO 30
<211> LENGTH: 83
<212> TYPE: DNA
<213> ORGANISM: Artificial Sequence
<220> FEATURE:
<223> OTHER INFORMATION: Synthetic

<400> SEQUENCE: 30
aagattcttg caaagctgga gcgcttaaaa tgaagacttg aggagaatgg ctgagtctct      60
ccggtaggtt tgaaatactc aag                                              83

<210> SEQ ID NO 31
<211> LENGTH: 91
<212> TYPE: DNA
<213> ORGANISM: Artificial Sequence
<220> FEATURE:
<223> OTHER INFORMATION: Synthetic
```

```
<400> SEQUENCE: 31
aagattcttg caaagctgga gcgcttaaaa caacaaaatg aagacttgag gagaatggct    60
gagtctctcc ggtaggtttg aaatactcaa g                                  91

<210> SEQ ID NO 32
<211> LENGTH: 90
<212> TYPE: DNA
<213> ORGANISM: Artificial Sequence
<220> FEATURE:
<223> OTHER INFORMATION: Synthetic

<400> SEQUENCE: 32
aagattcttg caaagctgga gcgcttaaac aacaaaatga agacttgagg agaatggctg    60
agtctctccg gtaggtttga aatactcaag                                    90

<210> SEQ ID NO 33
<211> LENGTH: 90
<212> TYPE: DNA
<213> ORGANISM: Artificial Sequence
<220> FEATURE:
<223> OTHER INFORMATION: Synthetic

<400> SEQUENCE: 33
aagattcttg caaagctgga gcgcttaaac aacaaaatga agacttgagg agaatggctg    60
agtctctcgg gtaggtttga aatactcaag                                    90
```